(12) United States Patent
Martin et al.

(10) Patent No.: US 8,097,238 B2
(45) Date of Patent: Jan. 17, 2012

(54) CELL TARGETING CONJUGATES

(75) Inventors: Roger Francis Martin, Ivanhoe (AU);
Jonathan Michael White, Wheelers Hill (AU); Pavel Nikolaevich Lobachevsky, Bulleen (AU); Thomas Chris Karagiannis, Thornbury (AU)

(73) Assignee: Peter MacCallum Cancer Institute, East Melbourne (AU)

( * ) Notice: Subject to any disclaimer, the term of this patent is extended or adjusted under 35 U.S.C. 154(b) by 1179 days.

(21) Appl. No.: 10/590,784

(22) PCT Filed: Feb. 25, 2005

(86) PCT No.: PCT/AU2005/000266
§ 371 (c)(1),
(2), (4) Date: Feb. 21, 2007

(87) PCT Pub. No.: WO2005/082894
PCT Pub. Date: Sep. 9, 2005

(65) Prior Publication Data
US 2007/0140970 A1    Jun. 21, 2007

(30) Foreign Application Priority Data
Feb. 27, 2004  (AU) ................................ 2004901013

(51) Int. Cl.
*A61K 51/00* (2006.01)
*A61M 36/14* (2006.01)

(52) U.S. Cl. ..................... 424/1.73; 424/1.11; 424/1.65; 424/1.85

(58) Field of Classification Search .................. 424/1.11, 424/1.49, 1.65, 1.69, 1.73, 1.81, 1.85, 1.89, 424/9.1, 9.2, 9.3, 9.4, 9.5, 9.6, 9.7, 9.8; 534/7, 534/10–16; 536/22.1, 23.1, 24.1, 25.3, 25.6, 536/26.1, 27.1
See application file for complete search history.

(56) References Cited

U.S. PATENT DOCUMENTS
5,759,514 A *  6/1998  Mattes .......................... 424/1.65
6,194,414 B1 *  2/2001  Martin et al. ............. 514/252.13

FOREIGN PATENT DOCUMENTS
WO      WO 97/004776 A1     2/1997

OTHER PUBLICATIONS

Kelly et al., DNA Binding Compounds. V Synthesis and Characterization of Boron-Containing Bibenzimidazoles Related to the DNA Minor Groove Binder, Hoechst 33258 (1994), Aust. J. Chem., pp. 247-262.
Harapanhalli et al., [1251/1271] IodoHoechst 33342: Synthesis, DNA Binding, and Biodistribution (1996), J. Med. Chem., vol. 39, No. 24, pp. 4804-4809.
Supplementary European Search Report dated Sep. 29, 2009.
STN File CA, Abstract 134:291615, T.G. Minehan, et al., "Molecular recognition of DNA by Hoechst benzimidazoles: exploring beyond the pyrrole-imidazole-hydroxypyrrole polyamide-pairing code", Helvetica Chimica Acta, 2000, pp. 2197-2213, vol. 83, No. 9.
STN File CA, Abstract 126:235131, S. Frau, et al., :Nuclease activity and binding characteristics of a catatonic 'manganese porphyrin-bis (benzimidazole) dye (Hoechst 33258)' conjugate, Bioconjugate Chemistry, 1997, pp. 222-231, Vol. 8, No. 2.
STN File CA, Abstract 124:444084, S, Frau, et al., "Synthesis and characterization of a cationic 'manganese porphyrin-bisbenzimidazole dye (Hoest 33258)' conjugate as a potential sequence-selective DNA cleaver", New Journal of Chemistry, 1995, pp. 873-876, vol. 19, No. 8-9.
STN File CA, Abstract 115:250504, S.D. Ivanov, et al., "Spectral properties of bisbenzimidasoles interacting with nucleic acids", Bioorganicheskaya Khimiya, 1991, pp. 1041-1047, vol. 17, No. 8.
International Search Report dated Apr. 15, 2005.

* cited by examiner

*Primary Examiner* — D L Jones
(74) *Attorney, Agent, or Firm* — Sughrue Mion, PLLC

(57) ABSTRACT

The present invention relates to cell targeting conjugates and in particular, but not exclusively, to methods of their use in selectively eliminating and in selectively imaging target cells. The invention also relates to processes for production of the conjugates and to intermediate compounds that may be used in production of a specific class of cell targeting conjugates. In one embodiment there is provided a cell targeting conjugate comprising the following components that are covalently conjugated via a linker that is degradable within the target cells:
  i) a DNA minor groove binding ligand incorporating an effective Auger electron-emitting and/or gamma-emitting and/or positron-emitting atom or photoactive moiety;
  ii) a target cell specific protein or peptide that is capable of internalization by target cells.

4 Claims, 18 Drawing Sheets

CELL TARGETING CONJUGATES

FIELD OF THE INVENTION

The present invention relates to cell targeting conjugates and in particular, but not exclusively, to methods of their use in selectively eliminating and in selectively imaging target cells. The invention also relates to processes for production of the conjugates and to intermediate compounds that may be used in production of a specific class of cell targeting conjugates.

BACKGROUND OF THE INVENTION

The strategy of using anti-tumour antibodies labelled with radioactive isotopes to target and eliminate tumour cells, known as radioimmunotherapy, is an old concept in cancer therapy, with a history marked by periods of both optimism and disappointment. The advent of hybridomas boosted the discovery of a large number of candidate mouse anti-tumour antibodies with potential use in radioimmunotherapy, but this optimism was tempered by the problem of the human anti-mouse monoclonal antibody response (HAMMA), which in some instances has been countered by the engineering of humanised mouse monoclonal antibodies. Genetic engineering has also provided the means to generate and select antibody variants to optimise affinity of the antibody for the target antigen. From this background, radioimmunotherapy is now an established mode of cancer therapy for lymphoma. In fact two labelled anti-CD20 antibodies, Zevalin ($^{90}$Yt) and Bexxar ($^{131}$I) have been used in successful clinical trials and both have been approved by the US FDA for the treatment of lymphoma.

Recombinant technology has facilitated the production of antibody fragments to overcome problems of delivery of the relatively large antibody molecules to cancer cells, particularly in solid tumours. Such heterogeneity of labelled antibody uptake, as well as heterogeneity of expression of the tumour antigen being targeted, has had an impact on the choice of radioactive isotope used in radioimmunotherapy. Thus, with the use of β-emitting isotopes, the range of which provides potential for "cross-fire", tumour cells that escape binding by the labelled antibody are still subject to cell kill by the radiation flux from labelled neighbours. However, all these strategies have had limited success in realising a widespread role for radioimmunotherapy to treat solid tumours. Nevertheless the efforts continue, in particular exploring the potential of radioimmunotherapy to treat small tumour deposits, or minimal residual disease, for which antibody delivery is less of a problem.

Whereas the radioimmunotherapy strategy involves the use of tumour-seeking antibodies incorporating a radioactive isotope, another approach is to combine the tumour-targeting feature of particular antibodies with a non-radioactive toxic moiety. The first examples of such immunoconjugates used bacterial toxins as the cytotoxic moiety. However, for various reasons these approaches have not proved successful in the clinic (Kreitman, 2001). By contrast, drug-immunoconjugates seem much more promising. In general, the nature of the cytotoxic moiety requires that the antibody-receptor complex is internalised, in contrast to radioimmunotherapy where the range of action of the radioactive isotope is generally such that internalisation is not necessary.

The potency of the cytotoxic moiety of the immunoconjugate strategy is an important feature because of the limited number of receptors per cell. This consideration was the basis for the early interest in bacterial toxins, which are extremely potent, requiring only a few molecules per cell for cell kill. Calicheamicin, a member of a very potent enediyene class of cytotoxic drugs, has been conjugated to an anti-CD33 antibody. This conjugate, denoted Gemtuzumab Ozogamicin was recently approved by US FDA for treatment of acute myeloid lymphoma (AML). A number of similar products are now in development.

More recently U.S. Pat. No. 5,759,514 to Mattes has disclosed therapeutic anti-tumour conjugates of a DNA intercalating small molecule linked to an Auger electron-emitting radioisotope and a cell-targeting protein or polypeptide. This document, however, provides only limited information in relation to production of the conjugates and provides no demonstration that the conjugates are taken up by, and can give rise to selective elimination of, the target cells.

In view of the above discussion it is clear that further therapeutic approaches are required, which offer the capability of selectively targeting and eliminating specific cell populations, and tumour cell populations in particular. It is with this in mind that the present invention has been conceived. Furthermore, the present inventors have not only demonstrated that this invention provides a means of selectively eliminating target cells by virtue of Auger electron induced DNA strand breakage, but they have shown that the invention offers a means of imaging to assess the efficacy of delivery of the Auger-emitting isotope to the tumour, by gamma- and/or positron-emission. The information from such imaging could be used for dosimetry calculations for subsequent treatments. The inventors have also demonstrated the targeting of an alternative cytotoxic modality, namely by initiating photo-cleavage events in close proximity to target cell DNA, a strategy which has potential in ex-vivo purging of target cells and in selective target cell imaging.

SUMMARY OF THE INVENTION

According to a preferred embodiment of the present invention there is provided a cell targeting conjugate comprising the following components that are covalently conjugated via a linker that is degradable within the target cells:
  i) a DNA minor groove binding ligand incorporating an effective Auger electron-emitting and/or gamma-emitting and/or positron-emitting atom or photoactive moiety;
  ii) a target cell specific protein or peptide that is capable of internalisation by target cells.

According to another embodiment of the invention there is provided a method of selectively eliminating target cells comprising administering to an environment in which the target cells are located an effective amount of a cell targeting conjugate, comprising the following components that are covalently conjugated via a linker that is degradable within the target cells:
  i) a DNA minor groove binding ligand incorporating a cytotoxically effective Auger electron emitting atom;
  ii) a target cell specific protein or peptide that is capable of internalisation by the target cells.

According to a further embodiment of the present invention there is provided a method of selectively eliminating target cells comprising administering to an environment in which the target cells are located an effective amount of a cell targeting conjugate, comprising the following components that are covalently conjugated via a linker that is degradable within the target cells:
  i) a DNA minor groove binding ligand incorporating a photoactive moiety which when photoactivated generates a species that induces cytotoxic DNA damage;

ii) a target cell specific protein or peptide that is capable of internalisation by the target cells;

and exposing the target cells to a source of UV light suitable to initiate formation of the species that induces cytotoxic DNA damage.

According to a still further embodiment of the present invention there is provided a method of selectively imaging target cells comprising administering to an environment in which the target cells are located an effective amount of a cell targeting conjugate, comprising the following components that are covalently conjugated via a linker that is degradable within the target cells:

i) a DNA minor groove binding ligand incorporating a gamma-emitting and/or positron-emitting atom;
ii) a target cell specific protein or peptide that is capable of internalisation by the target cells;

and detecting and imaging gamma and/or positron emissions from the target cells.

In a preferred embodiment of the invention the linker comprises a hydrazone, and/or disulphide and/or amide bond.

In a preferred embodiment of the invention the DNA minor groove binding ligand is selected from lexitropsins, bibenzimidazoles, tribenzimidazoles, benzoxazoles, benzthiazoles, purines, DAPI, diarylamidines, SN series ligands, pentamidine analogues, CC1065, naturally occurring antibiotics; and analogues thereof.

In another preferred embodiment of the invention the target cell specific protein or peptide is selected from anti-A33, C595, 4D5, trastuzumab (Herceptin), egf/R3, humanized h-R3, C225 (Erbitux), BrE-3, murine A7, C50, humanized MN-14, anti-A33, MSN-1, bivatuzumab, U36, KIS1, HuM195, anti-CD45, anti-CD19, TXU(anti-CD7)-pokeweed antiviral protein, M195, anti-CD23, apolizumab (Hu1D10), Campath-1H, N901, Ep2, somatostatin analogues (e.g. octreotide), tositumomab (Bexxar), ibritumomab tiuxetan (Zevalin), HB22.7, anti-CD40, OC125, PAM4 and J591.

In a particularly preferred embodiment of the invention the cell targeting conjugate is represented by Formula (I), wherein:

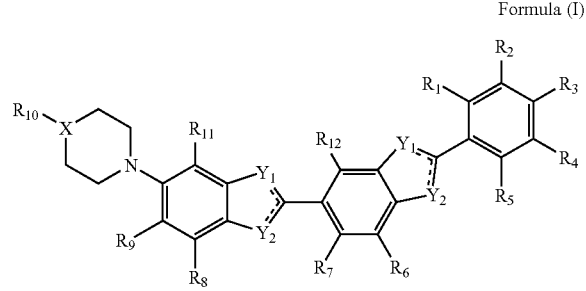

Formula (I)

X is carbon or nitrogen;
Y$_1$ and Y$_2$ are selected from C(R'), nitrogen, N(R'), oxygen and sulfur, wherein R' is hydrogen, optionally substituted alkyl or optionally substituted alkenyl, and wherein Y$_1$ and Y$_2$ are not both either C(R') or nitrogen;
═ is a double bond unless the attached Y$_1$ or Y$_2$ is N(R'), oxygen or sulfur in which case it is a single bond;
R$_1$ to R$_{12}$ are selected from hydrogen, halogen, hydroxy, amino, optionally substituted alkyl, optionally substituted alkenyl, a moiety including a target cell specific protein or peptide, an Auger electron-emitting moiety, a gamma-emitting moiety, a positron-emitting moiety, a photoactive moiety and a cellular uptake inhibiting group, and wherein two of R$_1$ to R$_5$ may together form optionally substituted cycloalkyl, cycloalkenyl or aryl;
wherein at least one of R$_1$ to R$_{12}$ comprises a target cell specific protein or peptide, and wherein at least one other of R$_1$ to R$_{12}$ comprises an Auger electron-emitting moiety, a gamma-emitting moiety, a positron-emitting moiety and/or a photoactive moiety;

and salts thereof, pharmaceutically acceptable derivatives thereof, pro-drugs thereof and/or tautomers thereof.

In another embodiment of the invention the cell targeting conjugate is administered to an ex-vivo population of cells.

In a further embodiment of the invention the cell targeting conjugate is administered to a mammalian patient.

Preferably the target cells are tumour cells.

According to another embodiment of the present invention there is provided a compound according to Formula (I) wherein:

X is carbon or nitrogen;
Y$_1$ and Y$_2$ are selected from C(R'), nitrogen, N(R'), oxygen and sulfur, wherein R' is hydrogen, optionally substituted alkyl or optionally substituted alkenyl, and wherein Y$_1$ and Y$_2$ are not both either C(R') or nitrogen;
═ is a double bond unless the attached Y$_1$ or Y$_2$ is N(R'), oxygen or sulfur in which case it is a single bond;
R$_1$ to R$_{12}$ are selected from hydrogen, halogen, hydroxy, amino, optionally substituted alkyl, optionally substituted alkenyl, a leaving group, an activating group, a chelating group and a cellular uptake inhibiting group, and wherein two of R$_1$ to R$_5$ may together form optionally substituted cycloalkyl, cycloalkenyl or aryl;
wherein at least one of R$_1$ to R$_{12}$ comprises a carbonyl, carboxylic acid or amino group, and wherein at least one other of R$_1$ to R$_{12}$ comprises a leaving group, an activating group or a chelating group;

and salts thereof, pharmaceutically acceptable derivatives thereof, pro-drugs thereof and/or tautomers thereof.

According to another embodiment of the present invention there is provided a compound according to Formula (I) wherein:

X is carbon or nitrogen;
Y$_1$ and Y$_2$ are selected from C(R'), nitrogen, N(R'), oxygen and sulfur, wherein R' is hydrogen, optionally substituted alkyl or optionally substituted alkenyl, and wherein Y$_1$ and Y$_2$ are not both either C(R') or nitrogen;
═ is a double bond unless the attached Y$_1$ or Y$_2$ is N(R'), oxygen or sulfur in which case it is a single bond;
R$_1$ to R$_{12}$ are selected from hydrogen, halogen, hydroxy, amino, optionally substituted alkyl, optionally substituted alkenyl, an Auger electron-emitting moiety, a gamma-emitting moiety, a positron-emitting moiety, a photoactive moiety and a cellular uptake inhibiting group, and wherein two of R$_1$ to R$_5$ may together form optionally substituted cycloalkyl, cycloalkenyl or aryl;
wherein at least one of R$_1$ to R$_{12}$ comprises a carbonyl, carboxylic acid or amino group, and wherein at least one other of R$_1$ to R$_{12}$ comprises an Auger electron-emitting moiety, a gamma-emitting moiety, a positron-emitting moiety or a photoactive moiety;

and salts thereof, pharmaceutically acceptable derivatives thereof, pro-drugs thereof and/or tautomers thereof.

BRIEF DESCRIPTION OF THE FIGURES

The present invention will be described further and by way of example only, with reference to the figures, wherein.

DETAILED DESCRIPTION OF THE INVENTION

Figure 1:
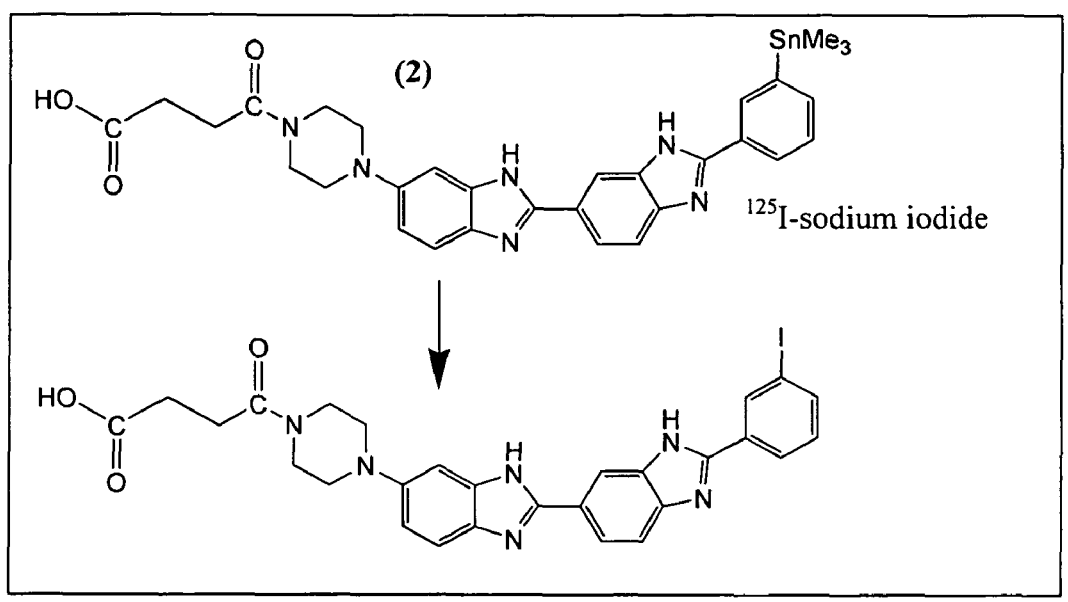
FIG. 1 shows a diagrammatic representation of the iodod-estannylation reaction, specifically where 3-trimethylstannyl-1-{5'-[5"-(4'"-(1""-oxy-4""-carboxybut-1-yl)piperazin-1'"-yl)benzimidazol-2"-yl]benzimidazol-2'-yl}benzene (2) is iodinated.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that that prior art forms part of the common general knowledge in Australia.

In its broadest aspect the present invention relates to cell targeting conjugates comprising a DNA ligand incorporating an effective Auger electron-emitting and/or gamma-emitting and/or positron-emitting atom or photoactive moiety and a target cell specific protein or peptide that is capable of internalisation by target cells, and which is covalently conjugated to the DNA ligand via a linker that is degradable within the target cells. The invention also relates methods of eliminating and imaging target cells using the conjugates, to synthesis of the conjugates and to intermediate compounds in synthesis of a specific class of conjugates.

In considering the design of cytotoxic drugs, DNA is an obvious target. Some DNA binding drugs or ligands form covalent adducts with the DNA molecule, and thus interfere with transcription or DNA replication. However non-covalent association of drugs with DNA, can also have inhibiting effects with cytotoxic consequences.

Non-covalent binding DNA ligands fall generally into two classes; the intercalating agents or drugs and the minor groove binding agents or drugs. The early examples of DNA intercalating drugs were aminoacridines, but anthracyclines, particularly doxorubicin have found more extensive clinical application. Other examples of intercalating agents, that are often characterised by having a region of planar shape able to slide between base pairs of the DNA double helix, include acridine and derivatives thereof, diacridine and derivatives thereof, bis-anthracyclines, diaminoacridines, phenanthridines, ethidium bromide and derivatives thereof, diquinolines, nitracrine, phenanthridium, daunomycin, mepacrine, acridine orange, methidium spermine and quinazoline derivatives.

A quite different mode of DNA binding is one in which the minor groove of the DNA double helix is the receptor for the drug molecule. The best-known example of these DNA minor groove binding ligands is the bibenzimidazole, Hoechst 33342. This drug is a member of a collection of analogues (also including Hoechst 33258) synthesised by the Hoechst Company in the 1970's principally as part of a programme to develop anti-helminthic agents, although its anti-tumoux activity has also been investigated. However the most widespread use of the drug is as a fluorescent stain of DNA, in various cytological applications. Other DNA minor groove binding ligands that may be utilised in the invention include the following:

Lexitropsins such as netropsin and distamycin analogues and conjugates, which contain peptide-linked pyrroles (or imidazoles or thiazoles);

Bibenzimidazoles (eg Hoechst 33342) and tribenzimidazoles, and analogues with one or more of the benzimidazole rings replaced by heterocycles such as benzoxazoles, benzthiazoles, and purines;

4',6-amidino-2-phenylindole (DAPI) and analogues thereof;

Berenil (a 1,3 diaryltriazine) and other diarylamidines;

The so-called "SN series" ligands, generally with 5 six-membered rings, some linked directly (eg SN6570 includes a diphenyl), others by peptide (eg SN6113 has four peptide linkages) or other 2-atom linkages (eg SN18071 has two C—C double bonds), some with combinations of 2-atom and single atom linkers (eg SN6053 has two peptide and two NH of links);

Pentamidine analogues (diarylamidines with a 2-6 atom bridge of an alkyl diamine or diether);

CC1065 and its analogues such as CPI 156, adozelesin, bizelesin; and

Naturally-occurring antibiotics such as anthramycin, tomaymycin.

Preferred DNA minor groove binding ligands adopted in the present invention are those that do not demonstrate an innate DNA damaging activity.

An important distinction between minor groove binders and intercalators is binding affinity and kinetics. The association constants for equilibrium binding of the classic aminoacridine DNA intercalators are generally in the range $10^4$-$10^5$ $M^{-1}$ (Kapuscinski & Darzynkiewicz, 1987; Wadkins & Graves, 1989), whereas the affinity of minor groove binders is generally at least two orders of magnitude higher (Breusegem et al., 2001). In general the affinity differences reflect the slower dissociation of the minor groove binders, with dissociation rate constants of 0.01-0.5 $sec^{-1}$ (Breusegem et al., 2001), compared to >10 $sec^{-1}$ for aminoacridines (Denny & Wakelin, 1986). Intercalators such as Actinomycin D and doxorubicin with bulky groups that protrude into the minor or major grooves have intermediate affinity (about $10^6$ $M^{-1}$) and dissociation rates from DNA (Piehler et al., 1997). Importantly, these differences are directly relevant to the affinity and kinetics of binding of the ligands to nuclear DNA in cells.

A particularly preferred class of DNA ligand that may be incorporated within the conjugates of the invention are the bibenzimidazole DNA minor groove binding ligands, which give rise to conjugates defined by Formula (I):

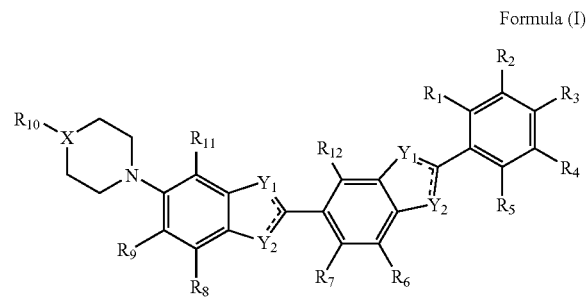

Formula (I)

wherein:

X is carbon or nitrogen;

$Y_1$ and $Y_2$ are selected from C(R'), nitrogen, N(R'), oxygen and sulfur, wherein R' is hydrogen, optionally substituted alkyl or optionally substituted alkenyl, and wherein $Y_1$ and $Y_2$ are not both either C(R') or nitrogen;

═ is a double bond unless the attached $Y_1$ or $Y_2$ is N(R'), oxygen or sulfur in which case it is a single bond;

$R_1$ to $R_{12}$ are selected from hydrogen, halogen, hydroxy, amino, optionally substituted alkyl, optionally substituted alkenyl, a target cell specific protein or peptide, an Auger electron-emitting moiety, a gamma-emitting moiety, a positron-emitting moiety, a photoactive moiety and a cellular uptake inhibiting group, and wherein two of $R_1$ to $R_5$ may together form optionally substituted cycloalkyl, cycloalkenyl or aryl; wherein at least one of $R_1$ to $R_{12}$ comprises a target cell specific protein or peptide, and wherein at least one other of $R_1$ to $R_{12}$ comprises an Auger electron-emitting moiety, a gamma-emitting moiety, a positron-emitting moiety or a photoactive moiety;

and salts thereof, pharmaceutically acceptable derivatives thereof, pro-drugs thereof and/or tautomers thereof.

Particularly preferred DNA minor groove binding ligands include the bibenzimidazole compounds related to Hoechst 33258-4-hydroxy-1-{5'[5'''-(4'''-methylpiperazin-1'''-yl)benzimidazol-2''-yl]benzimidazol-2'-yl}benzene; and Hoechst 33342-4-ethoxy-1-{5'[5'''-(4''''-methylpiperazin-1''''-yl)benzimidazol-2''-yl]benzimidazol-2'-yl}benzene.

Figure 2:
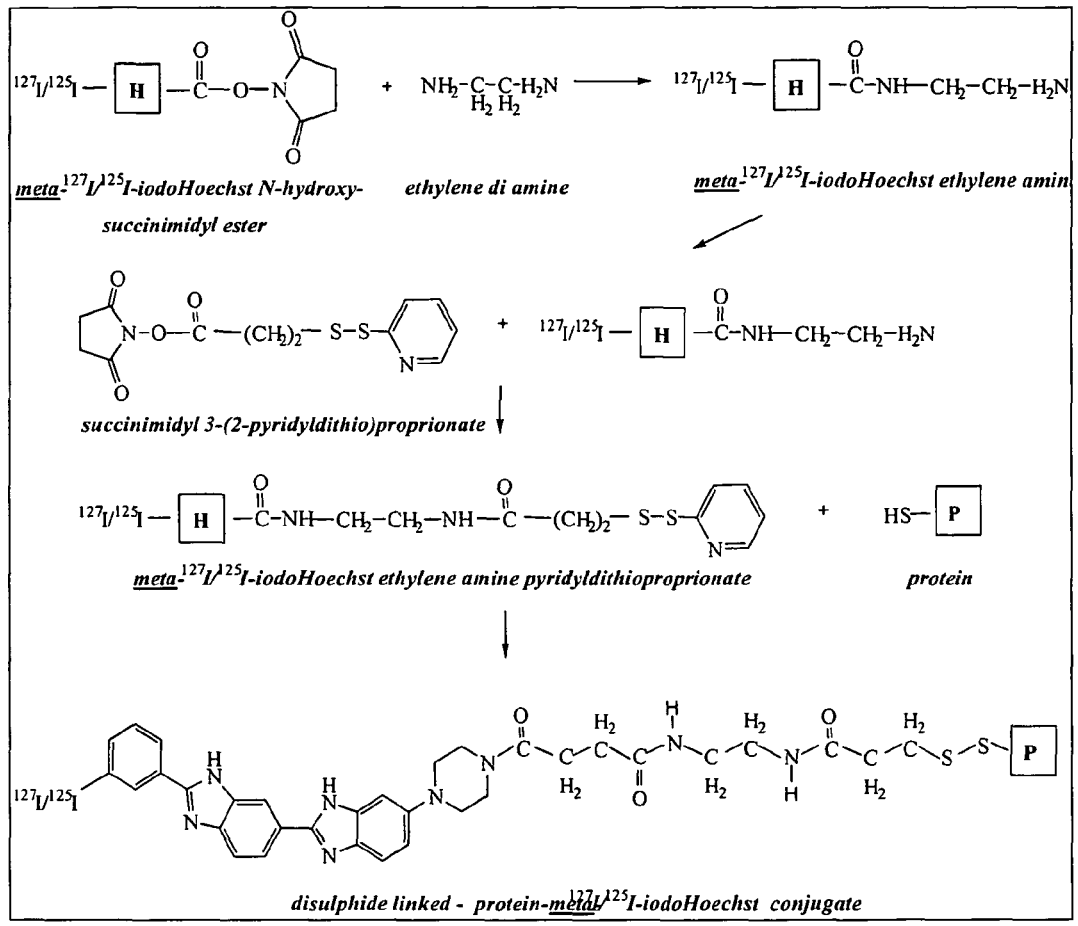
FIG. 2 shows a diagrammatic representation of the conjugation of meta-$^{127}$I/$^{125}$I-iodoHoechst to proteins via a disulphide linkage.
Figure 3:
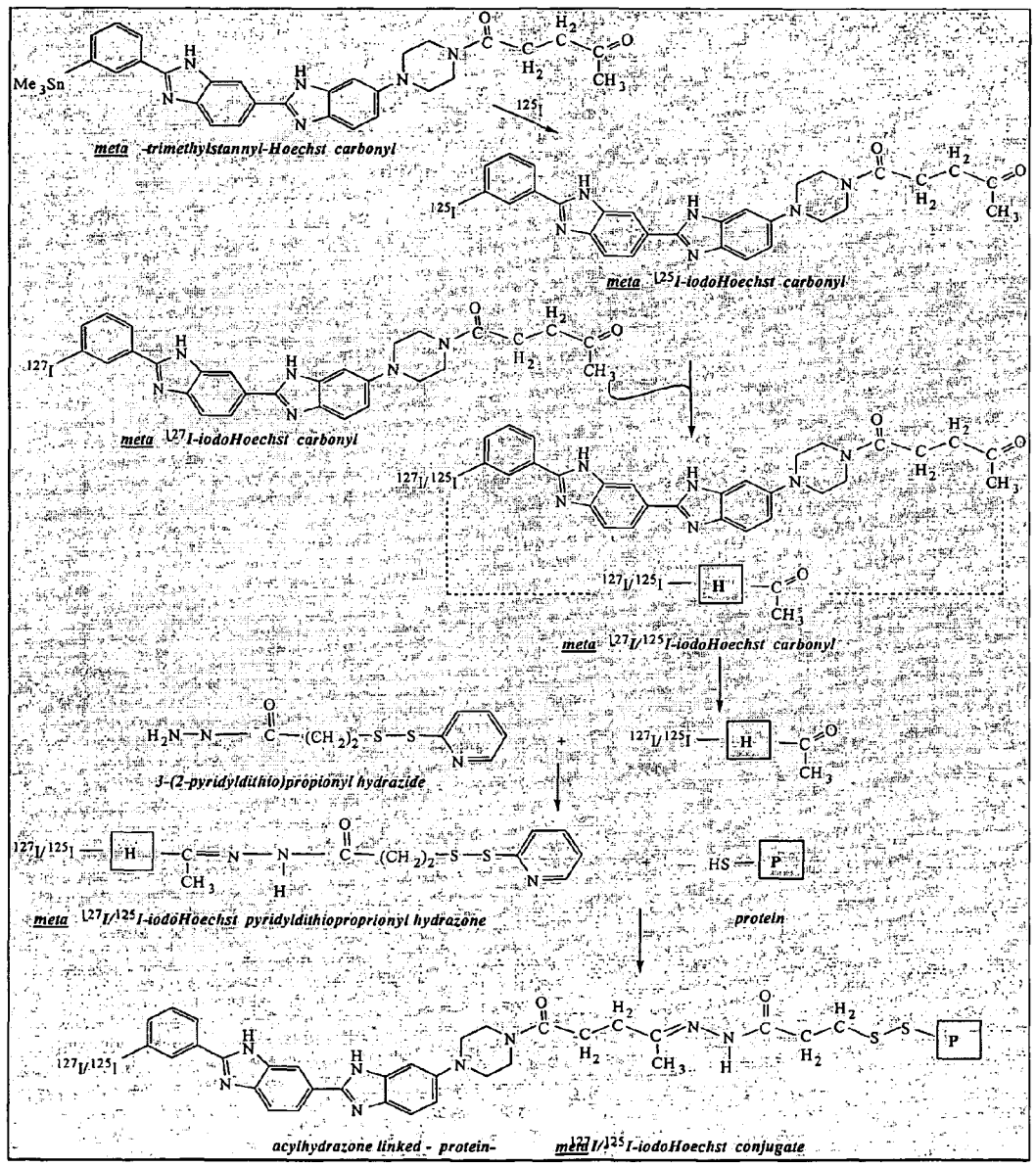
FIG. 3 shows a diagrammatic representation of the conjugation of meta-$^{127}$I/$^{125}$I-iodoHoechst to proteins via an acylhydrazone linkage.
Figure 4:
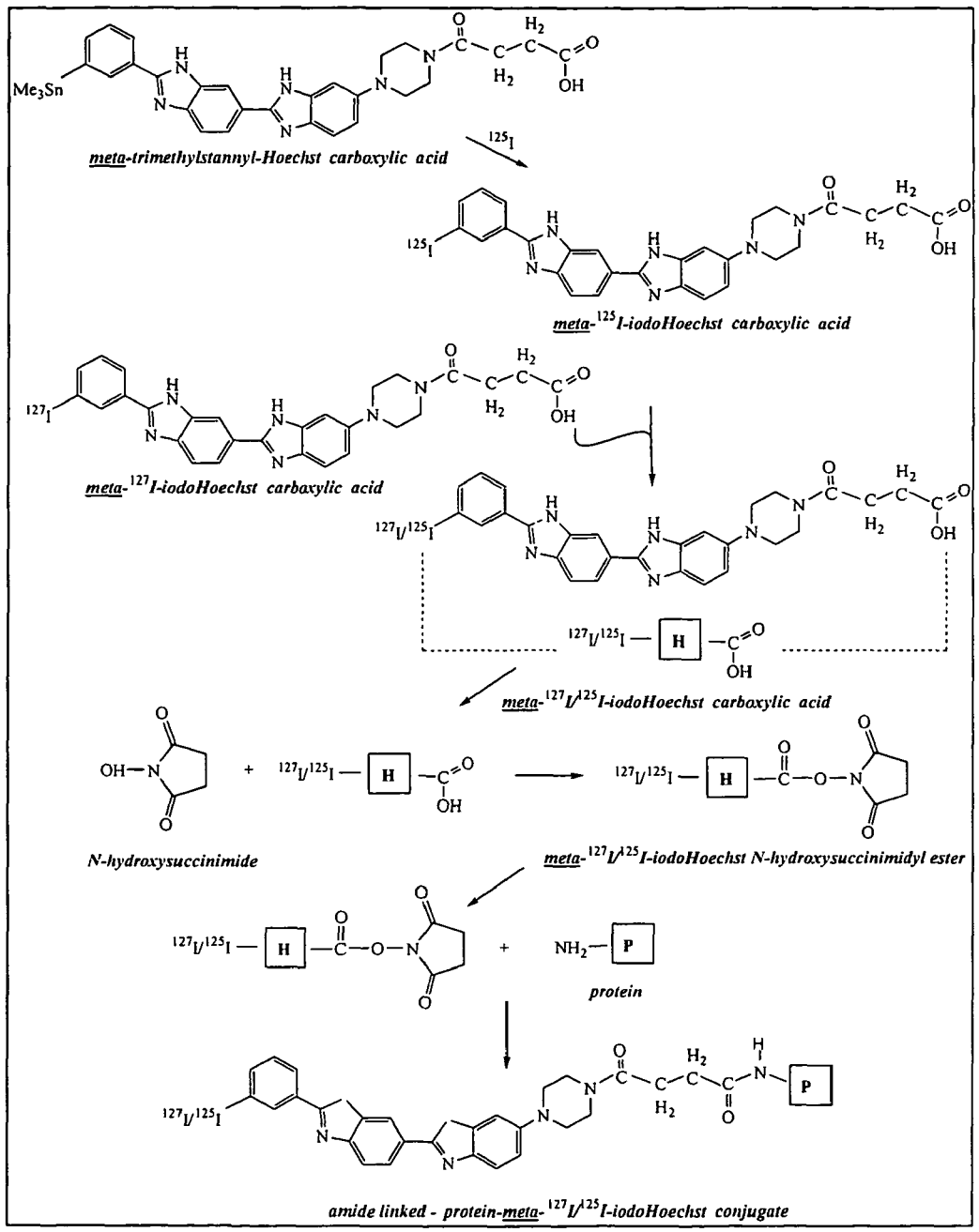
FIG. 4 shows a diagrammatic representation of the conjugation of meta-$^{127}$I/$^{125}$I-iodoHoechst to proteins via an amide linkage.

Examples of particularly preferred conjugates of the invention, which utilise bibenzimidazole structures as the DNA ligand component include conjugates exemplified in FIGS. 2-4.

As used herein, the term alkyl refers to straight chain, branched or cyclic fully saturated hydrocarbon residues, preferably straight chain or branched alkyl. Examples of straight chain and branched alkyl include $C_{1-20}$ alkyl such as methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Preferably the alkyl group is $C_1$-$C_{10}$ alkyl. Other examples of alkyl include $C_{21-25}$ alkyl, $C_{26-30}$ alkyl, $C_{31-35}$ alkyl, $C_{36-40}$ alkyl, $C_{41-46}$ alkyl, $C_{50-55}$ alkyl and $C_{56-60}$ alkyl. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein the term "alkenyl" denotes groups formed from straight chain, branched or cyclic hydrocarbon residues containing at least one carbon-carbon double bond including ethylenically mono-, di- or poly-unsaturated alkyl or cycloalkyl groups as previously defined. Examples of alkenyl include $C_{1-20}$ alkenyl such as vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. Preferably the alkenyl group is $C_2$-$C_{10}$ alkenyl. Other examples of alkenyl groups include $C_{10}$-$C_{15}$ alkenyl, $C_{16}$-$C_{20}$ alkenyl, $C_{21}$-$C_{25}$ alkenyl, $C_{26}$-$C_{30}$ alkenyl, $C_{31}$-$C_{35}$ alkenyl, $C_{36}$-$C_{40}$ alkenyl, $C_{41}$-$C_{45}$ alkenyl, $C_{46}$-$C_{50}$ alkenyl, $C_{51}$-$C_{55}$ alkenyl, $C_{56}$-$C_{60}$ alkenyl, $C_{61-65}$ alkenyl, $C_{66-70}$ alkenyl and $C_{71-80}$ alkenyl. Each of these may contain one or more alkyl or alkenyl branches.

Particular examples of alkenyl include:
isoprenoid chains of formula (a):

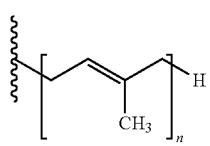

(a)

where n = 1-20

(poly)alkenyl chains of formula (b), (c), (d), (e) or (f):

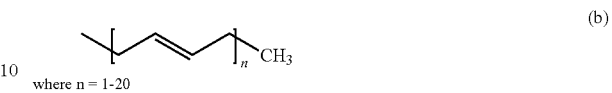

(b)

where n = 1-20

(c)

where n = 1-20

(d)

where n = 1-20

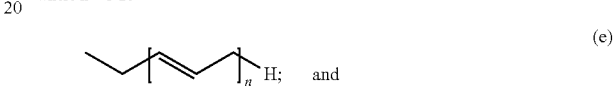

(e)

where n = 1-20

(f)

wherein n = 1-20

By the term "optionally substituted" in the context of optionally substituted alkyl, alkenyl or aryl it is intended to mean that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

A "leaving group" may be utilised in order to incorporate by substitution a desired group such as a radioactive nuclide or photoactive moiety at a desired location within compounds of the invention. For example, the leaving group may comprise a good electrofugal leaving group such as: —SnR$_3$, —GeR$_3$, —SiR$_3$, and borate complexes of the general structure —B(OR)$_3^-$, (where R is alkyl). It may be appropriate to utilise an activating group in conjunction with the leaving group.

By the term "activating group" it is intended to encompass chemical groups that may be used to activate electrophilic substitution at aromatic carbons located ortho- or para- to the activating group. Activating groups may for example comprise electron donating substituents such as —OH, —NH$_2$, —NHR and —NR$_2$ (where R=alkyl).

By the term "chelating group" it is intended to encompass compounds that are able to form complexes with metal ions. Examples of suitable chelating groups include the following:
EDTA (ethylene diamine tetraacetic acid);
DTPA (diethylenetriamine pentaacetic acid);

DOTA (1,4,7,10-tetraazacyclododecane-1,4,7,10-tetraacetic acid);

Macrocycles containing O (ie crown ethers), or N (lactams), or S or mixtures of O and N and/or S, and/or P, as the metal coordinating atoms, either in planar or 3-dimensional (cryptands) structures;

Naturally-occurring metal chelators, (eg peptides, such as Deferoxamine), or cyclic antibiotics such as valinomycin, or porphyrins.

"Cellular uptake inhibiting groups" include bulky, charged groups such as metal chelating agents (eg DPTA), with or without a chelated metal ion.

The salts of the compound of formula (I) are preferably pharmaceutically acceptable, but it will be appreciated that non-pharmaceutically acceptable salts also fall within the scope of the present invention, since these are useful as intermediates in the preparation of pharmaceutically acceptable salts, or may be utilised in ex vivo applications. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids.

By "pharmaceutically acceptable derivative" is meant any pharmaceutically acceptable salt, hydrate, solvate or any other compound which, upon administration to the subject, is capable of providing (directly or indirectly) a compound of formula (I) or an active metabolite or residue thereof.

The term "pro-drug" is used herein in its broadest sense to include those compounds that are converted in vivo to compounds of formula (I).

The term "tautomer" is used herein in its broadest sense to include compounds of formula (I) which are capable of existing in a state of equilibrium between two isomeric forms. Such compounds may differ in the bond connecting two atoms or groups and the position of these atoms or groups in the compound, The compounds of the invention may be electrically neutral or may be polycations with associated anions for electrical neutrality. Suitable associated anions include sulphate, tartrate, citrate, chloride, nitrate, nitrite, phosphate, perchlorate, halosulfonate or trihalomethylsulfonate, for example.

An important means of communication between cells and their environment involves receptors on the cell surface that recognise specific ligands. It is by the exploitation of such specific ligands ("target cell specific proteins or peptides") that cell targeting of the conjugates of the invention can be achieved. The binding of the ligand to its receptor can initiate a signalling cascade which may, for example, result in transcription of particular genes. A case in point is binding of epidermal growth factor (EGF) to its receptor (Jorissen et al., 2003). The EGF receptor protein (EGFR) is anchored in the phospholipid cell membrane and also has intra-cellular transmembrane and extra-cellular domains, the latter including the binding site for EGF. The intra-cellular domain includes a protein kinase activity, which is activated upon EGF binding, these events are the first in a cascade which eventually results in stimulation of cell division. In the case of the EGF system, the ligand receptor complex is internalised and degraded after initiation of the signalling process.

Although internalisation is not a universal feature of such receptor ligand complexes, in some systems internalisation is an essential part of the ligand-receptor function. Such is the case for the transferrin (TF) system, in which internalisation of the TF-TF receptor (TFR) complex is an innate part of the mechanism by which iron (attached to the TF molecule protein) is transported into the cell (Klausner et al., 1983). Given the essential role of iron in energy transfer and growth, TFR synthesis is elevated in actively growing cells, including some tumour cells (Faulk et al., 1980). Similarly, up regulation of EGFR density is a feature common to many tumour cells (Arteaga, 2003). The conjugates of the invention can therefore be designed to specifically target particular cell types or cells undergoing a particular growth or division phase by incorporating within the conjugates of a cell targeting protein or peptide that binds to cell surface receptors up regulated in the particular population of cells of interest. To allow ultimate association of the DNA ligand component of the inventive conjugates with cellular DNA, preferably nuclear DNA, it is important for the cell targeting protein or peptide adopted to undergo internalisation in the target cells of interest, preferably with specificity relative to other non-target cell populations. Examples of cell targeting proteins or peptides that may be incorporated in the conjugates of the invention (including reference to the cells/antigens they target) are provided in Table 1. It is to be understood that this list is referred to by way of example only and that other ligands, the receptors for which are up regulated in a population of cells of interest, whether or not presently known, are also encompassed by the present invention.

TABLE 1

Examples of antibodies/peptides directed against cell-surface antigens for targeted therapy of common cancers

| Cancer | Antigen | Antibody/Peptide |
|---|---|---|
| bladder | A33 | anti-A33 |
|  | MUC-1 | C595 |
| breast | Her-2 | 4D5, trastuzumab (Herceptin) |
|  | EGF | egf/R3 and humanized h-R3, |
|  | MUC-1 | C225 (Erbitux) BrE-3 |
| colorectal | Ep-CAM antigen (1-A7) anti-CEA | murine A7 C50, humanized MN-14 |
|  | A33 | anti-A33 |
|  | EGF | C225 (Erbitux) |
| endometrial | adenocarcinoma antigen | MSN-1 |
| head and neck; | EGF | C225 (Erbitux) |
|  | CD44v6 | bivatuzumab, U36 |
|  | squamous cell antigen | KIS1 |
| leukemia |  |  |
| AML | CD33 | HuM195 |
| CML | CD45 | anti-CD45 |
| CLL | CD19 | anti-CD19 |
| HCL | CD7 | TXU(anti-CD7)-pokeweed |
|  | CD33 | antiviral |
|  | CD23 | protein |
|  | HLA-DR | HuM195, M195 |
|  | CD52 | anti-CD23 |
|  |  | apolizumab (HuID10) |
|  |  | Campath-1H |
| lung (SCLC) | CD56 | N901 |
| melanoma | melanoma associated antigen | Ep2 |
| neuroendocrine | somatostatin receptor | somatostatin analogues (octreotide) |
| non-Hodgkin's lymphoma | CD20 CD22 | tositumomab (Bexxar), ibritumomab tiuxetan (Zevalin) HB22.7 |

TABLE 1-continued

Examples of antibodies/peptides directed against cell-surface antigens for targeted therapy of common cancers

| Cancer | Antigen | Antibody/Peptide |
|---|---|---|
| ovarian | CD40 | anti-CD40 |
| | Her-2 | trastuzumab (Herceptin) |
| | CA-125 antigen | OC125 |
| pancreatic | MUC-1 | PAM4 |
| prostate | prostate specific membrane antigen | J591 |

It is important to note the connection between receptor-mediated endocytosis and the anti-tumour antibodies used in radio immunotherapy. In some cases antibodies to the extracellular domain of receptor proteins can act in the same way as the natural ligands for the receptors, certainly in terms of binding to the receptors in the cell surface, and sometimes (eg. for the TF and EGF systems) the antibody-receptor complexes are internalised. More generally, the members of the large collection of anti-tumour antibodies, which have been raised empirically, include antibodies to cell surface receptors.

The cell targeting protein or peptide may, as long as it retains its ligand binding and cellular internalisation characteristics, comprise a complete ligand or a functionally equivalent analogue, variant or fragment thereof. By the phrase "functionally equivalent" it is intended to convey that the variant, analogue or fragment is also effective in binding to the cell surface receptor on the target cells and giving rise to internalisation of the ligand-receptor complex. Preferably, a given quantity of the analogue, variant or fragment is at least 10%, preferably at least 30%, more preferably at least 50, 60, 80, 90, 95 or 99% as effective as an equivalent amount of the native ligand from which the analogue, variant or fragment is derived. Determination of the relative efficacy of the analogue, variant or fragment can readily be carried out by utilising a prescribed amount of the analogue, variant or fragment in the cell elimination or imaging methods of the invention and then comparing the level of cell-kill or imaging efficiency against the same amount of native ligand from which the analogue, fragment or variant is derived.

Analogues and variants are intended to encompass proteins having amino acid sequence differing from the protein from which they are derived by virtue of the addition, deletion or substitution of one or more amino acids to result in an amino acid sequence that is preferably at least 60%, more preferably at least 80%, particularly preferably at least 85, 90, 95, 98, 99 or 99.9% identical to the amino acid sequence of the original protein. The analogues or variants specifically include polymorphic variants and interspecies homologues.

By reference to "fragments" it is intended to encompass fragments of a protein that are of at least 5, preferably at least 10, more preferably at least 20 and most preferably at least 30, 40 or 50 amino acids in length and which are of course functionally equivalent to the protein of which they are a fragment.

Throughout this specification the terms "polypeptide", "peptide" and "protein" are used interchangeably to refer to a polymer of amino acid residues. The terms apply equally to amino acid polymers in which one or more amino acid residues is an artificial chemical mimetic of a corresponding naturally occurring amino acid, as well as to both naturally and non-naturally occurring amino acid polymers.

The term "amino acid" refers to naturally occurring and synthetic amino acids as well as amino acid analogues and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. "Amino acid analogues" refers to compounds that have the same basic chemical structure as a naturally occurring amino acid, that is a carbon that is bound to a hydrogen, a carboxyl group, an amino group and an R group, e.g., homoserine, norleucine, methionine sulfoxide and methionine methyl sulphonate. Such analogues have modified R groups (e.g. norleucine) or modified peptide backbones, but retain the same basic chemical structure as a naturally occurring amino acid. Amino acid mimetics refers to chemical compounds that have a structure that is different from the general chemical structure of an amino acid, but retain a function similar to that of a naturally occurring amino acid.

Proteins, peptides and polypeptides of the invention may be isolated and purified from naturally occurring sources or may be synthetically produced by routine chemical or molecular biological techniques, as well understood in the art. The proteins or peptides of the invention may comprise antibodies specific for cell surface receptors or functionally equivalent fragments thereof. Further details of routine techniques for protein, peptide and antibody production and purification are provided in Sambrook & Russell, Molecular Cloning: A laboratory manual, 3rd Edition, 2001, Cold Spring Harbour Laboratory Press, New York, the disclosures of which are included herein in their entirety by way of reference.

In production of the conjugates the cell targeting protein or peptide will be covalently bound to the DNA ligand via a linker degradable within the target cells. Examples of suitable linkers include optionally substituted alkyl or alkenyl including hydrazone, amide and/or disulphide bonds, which when cleaved under appropriate conditions within the target cells allow release of the DNA ligand component of the conjugate from the cell targeting protein or peptide component. For example, hydrazone bonds may be cleaved under low pH conditions, disulphide bonds may be cleaved under reducing conditions and amide bonds may be cleaved by lysosomal enzymes, all of which are of the type that may be encountered with the cytoplasm of target cells. The linker component of the conjugates may include other types of bonds that are degradable within the cytoplasm of target cells, such as:

mercurial groups (—S—Hg—X—Hg—S—, where X is an alkyl or aryl linker, joined to the Hg atoms by C—Hg bonds, perhaps containing oxygen atoms, or similar, within the linker, to improve solubility) cleaved by free thiol, such as mercapto ethanol;

vicinal glycol (—CH(OH)—CH(OH)—) cleaved by oxidation;

azo linkages (—N═N—); cleaved by reduction;

sulphones (—SO$_2$—) cleaved by mild base;

esters (—CO—O—) and thioesters (—CO—S—) cleaved by acid or base;

maleylamide (—NH—CO—C═C(COO—)—X—, where X can be alkyl/aryl) cleaved by acid;

acetals (—O—CHR—O—), ketals (—O—CR$_2$—O—) and orthoesters (—C(OR)—O—C—X—) (where R is alkyl and X is alkyl or aryl) cleaved by mild acid.

The other key component of the conjugates of the invention is the presence on the DNA ligand of a moiety (hereinafter referred to as "the active moiety") (which is preferably an Auger electron-emitting, gamma-emitting, positron emitting and/or a photoactive moiety) that is detectable for imaging purposes and/or may give rise under appropriate conditions to an event such as radiation emission or radical formation, leading to DNA damage and ultimately elimination of the cell concerned (cell death). In having activities of the types mentioned above the active moiety can be considered to be "effective". It should be understood that the active moiety may exhibit more than one of the types of activities referred to above and further that more than one active moiety may be incorporated within the inventive conjugates. Furthermore, particularly for imaging applications of the invention the active moiety may be carried on an optionally substituted alkyl, optionally substituted alkenyl, optionally substituted alkynyl or optionally substituted aryl group which will serve to increase the distance from the active moiety and the DNA binding portion of the ligand. In this way, the active moiety will also be distanced from the DNA when the DNA ligand is to bound to DNA, such that the impact of DNA damaging Auger emissions from the active moiety are minimised. For example, the active moiety may be carried on an optionally substituted cycloalkyl, cycloalkenyl or cycloaryl substituent formed from two of groups $R_1$ to $R_5$ located about the terminal phenyl group of the ligand according to Formula (I). Exemplary structures showing distancing of the active moiety (in these cases "I") are provided in FIG. 17, where the variables $R_1$ to $R_{12}$ are as defined above and where R represents hydrogen, hydroxy, amino, halogen or optionally substituted alkyl, alkenyl or alkynyl.

In the 1920's the French physicist Pierre Auger, while studying photoelectric effect, discovered that very low energy electrons were emitted from atoms as part of the process of filling vacant inner shell orbitals. Such low energy electrons were subsequently referred to as Auger electrons (actually, and as used herein, this is a generic term, referring to three sub-classes, namely Auger, Coster-Kronig and super Coster-Kronig emissions, reflecting differences in the relationship between donor and acceptor orbitals). Many radioactive isotopes have decay schemes involving generation of inner shell vacancies (for example by electron capture or internal conversion), and such isotopes are referred to as Auger electron emitters or Auger emitters. The most studied example is $^{125}$I in which there are two episodes of Auger electron emission, the first following electron capture, and the second after internal conversion. Theoretical calculations indicate that for the average decay event, a total of around 20 Auger electron atoms are emitted, although there is a wide variation between individual decay events (Pomplun et al., 1987). Given the low energy (and consequent short range) of Auger electrons, such decay events are associated with an intense focus of radiochemical damage. This is illustrated by the consequences of decay of $^{125}$I in DNA, including (a) on average, about one DNA double-stranded break per decay; (b) a double-stranded break arising from a series of closely spaced single-stranded breaks, the majority of which occur within a few nucleotide base pairs at the site of decay (Lobachevsky & Martin, 2000a); and (c) resulting DNA damage is highly cytotoxic, with around 50-100 decays correspond to a lethal event. Studies have shown that the DNA damage arises not only from electron irradiation by Auger electrons, but is also from molecular fragmentation arising from the transient positive charge on the daughter atom (Lobachevsky & Martin, 2000b). In short, Auger emitters represent a very efficient means of inducing cell kill, if the decay event is targeted to DNA.

The relatively long half-life of the prototype Auger emitter $^{125}$I (60 days) places some limitations on head clinical utility particularly from the radiation protection standpoint. Shorter-lived Auger emitters such as $^{123}$I (13 hours) and $^{124}$I (4.2 days), $^{111}$In (2.8 days), $^{195m}$Pt (4 days), $^{67}$Ga (3.3 days) may therefore also be utilised. Details (including yields of positron, gamma and Auger emissions) of a representative, but not comprehensive, list of isotopes that may be utilised in the present invention are provided in Table 2. For the gamma emitters, the focus is on those isotopes with gamma emissions suitable for SPECT, namely with photon energies in the optimal range of 100-200 kev.

TABLE 2

Isotopic half-life, positron, gamma and Auger electron yield

| Isotope | Positron yield | Gamma (100-200 kev) most abundant | Auger electron yield | Half-life (T½) |
|---|---|---|---|---|
| 18F | 1 | | | 109.77m |
| 11C | 0.998 | | | 2.385m |
| 13N | 0.998 | | 0.0018 | 9.965m |
| 72As | 0.875 | | | 26.0h |
| 55Co | 0.759 | | | 17.53h |
| 73Se | 0.66 | | 0.081 | 7.15h |
| 66Ga | 0.565 | | | 9.49h |
| 52Fe | 0.56 | 0.992 | 0.683 | 8.275h |
| 76Br | 0.55 | | | 16.2h |
| 48V | 0.501 | | 0.86 | 15.97d |
| 57Ni | 0.429 | 0.162 | 0.835 | 35.65h |
| 52Mn | 0.296 | | 1.46 | 5.59d |
| 83Sr | 0.243 | | 4.33 | 32.4h |
| 82mRb | 0.229 | 0.017 | | 6.2h |
| 124I | 0.228 | | 1.81 | 4.18d |
| 84Rb | 0.209 | | 2.31 | 32.87d |
| 62Zn | 0.0839 | | 4.81 | 9.26h |
| 77Br | 0.074 | 0.012 | 3.76 | 57.04h |
| 48Cr | 0.0145 | 0.96 | 5.41 | 21.56h |
| 126I | 0.0115 | | 1.29 | 13.0d |
| 37Ar | | | 0.97 | 35.02d |
| 51Cr | | | 5.69 | 27.70d |
| 67Ga | | 0.204 | 5.72 | 3.26d |
| 73As | | | 10.8 | 80.3d |
| 72Se | | | 5.62 | 8.40d |
| 97Ru | | 0.0285 | 3.02 | 2.9d |
| 111In | | 0.902 | 3.09 | 2.83d |
| 117mSn | | 0.669 | 2.81 | 13.61d |
| 123I | | 0.833 | 2.99 | 13.2h |
| 125I | | | 4.49 | 60.14d |
| 129mXe | | 0.64 | 4.41 | 8.89d |
| 195mPt | | 0.397 | 4.67 | 4.02d |
| 195mHg | | 0.11 | 4.09 | 41.6h |
| 169Yb | | 0.349 | 5.2 | 32.02d |
| 191Os | | 0.258 | 2.93 | 15.4d |
| 190Ir | | 0.534 | 2.28 | 11.78d |
| 197mHg | | 0.296 | 3.07 | 23.8h |
| 201Tl | | 0.1 | 2.53 | 73.1h |
| 203Pb | | 0.136 | 2.01 | 51.87h |
| 206Bi | | 0.158 | 2.42 | 6.24d |

Figure 17:
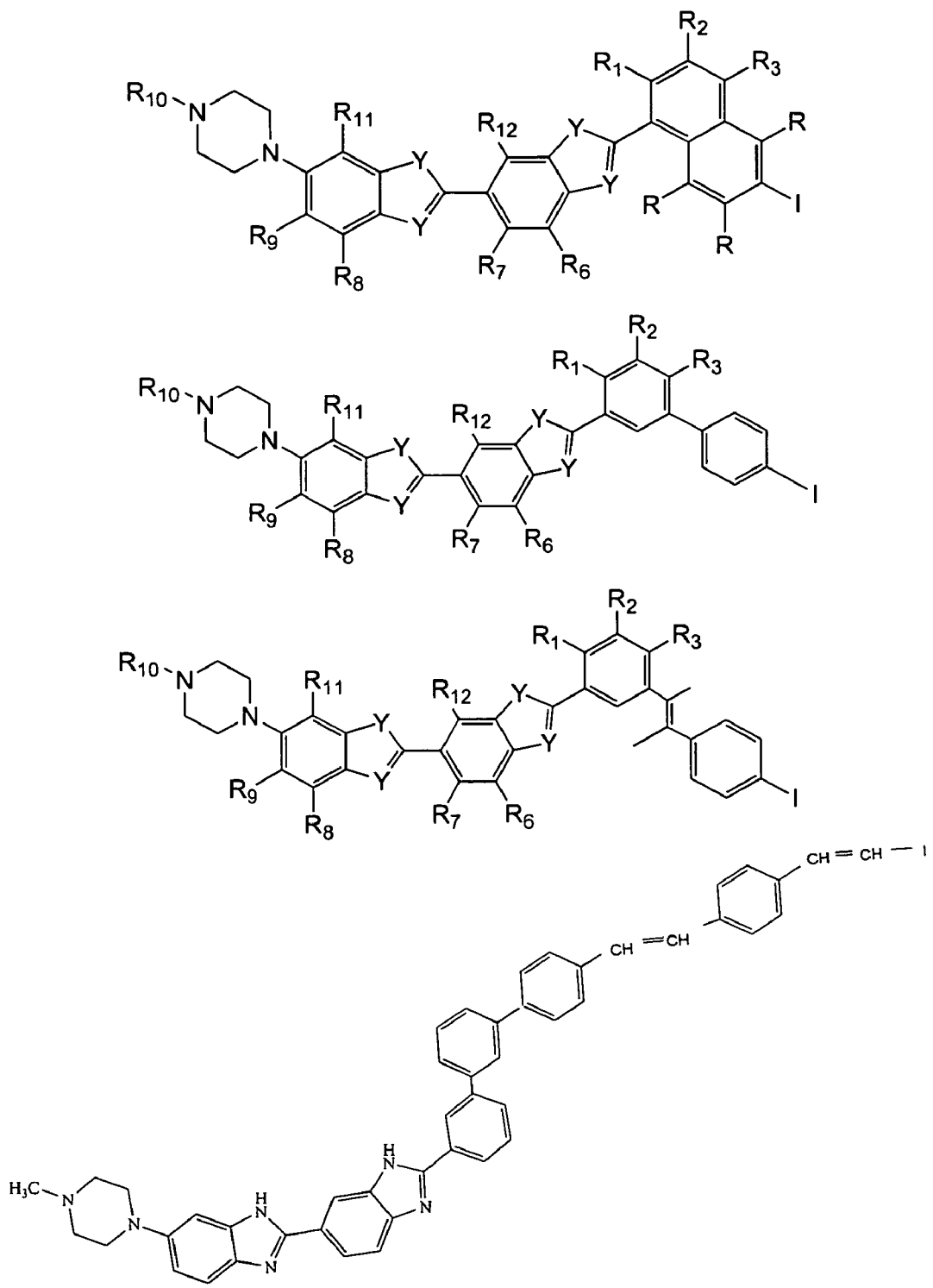
FIG. 17 shows exemplary general structures of compounds of the invention useful for imaging purposes, where the active moiety ("I") is distanced from the DNA minor groove binding portion of the compound.
Figure 17:
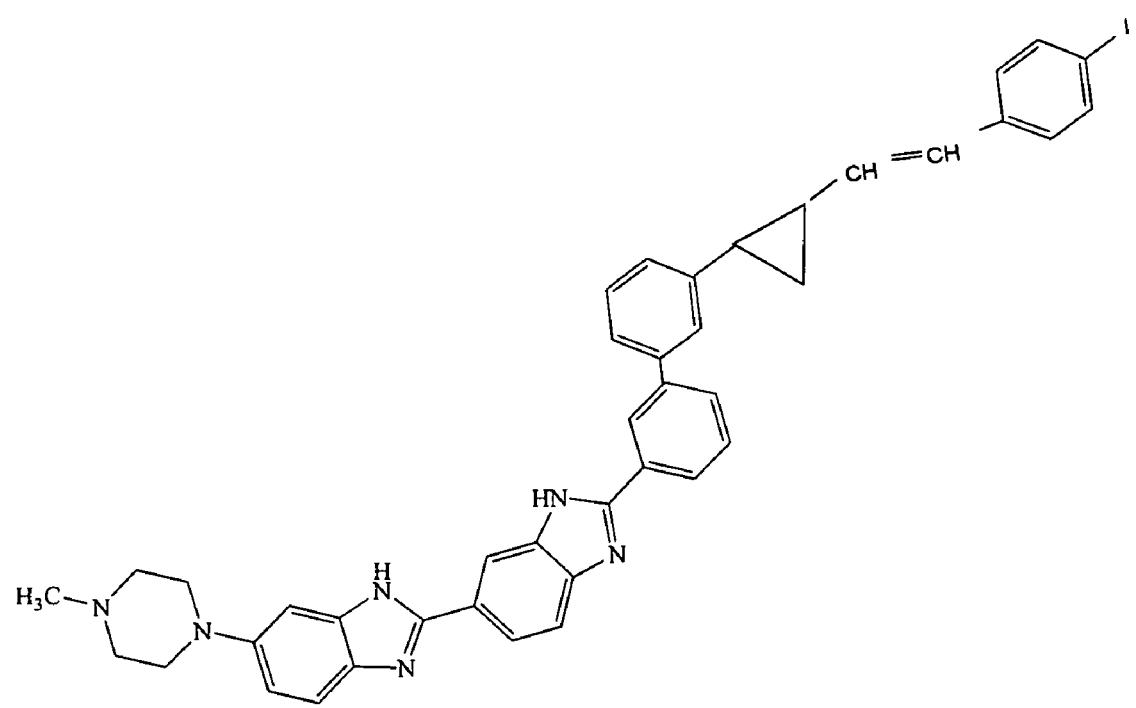

It can be seen from Table 2 (which is derived from Weber D A et al. MIRD: "Radionucleotide Data and Decay Schemes", Soc of Nuclear Med, 1989) that many isotopes have combined emissions, such as Auger electrons and gamma (eg 123I, 67Ga), or Auger electrons and positrons (such as 124I, 83Sr). Both these combinations will be useful in dual imaging/therapy applications. Thus for Auger/gamma, the gamma would be exploited for imaging (for example by SPECT) whereas the intense focus of radiochemical damage from the Auger electron emission would mediate the cytotoxic DNA damage for the therapeutic objective. Similarly, for Auger/positron combination, the positron emission would be exploited for imaging (for example by PET) whereas the intense focus of radiochemical damage from the Auger electron emission would be exploited for the therapeutic objective. For imaging-only applications, in which a non-invasive mode is preferred, the same combined emitters can be usefully employed provided the DNA-damaging effects of the Auger component are minimised by utilising a DNA ligand designed such that the radioactive atom is placed more distant from the DNA molecule in the DNA/ligand complex. For example, distancing of the active moiety can be achieved by including the active moiety within a larger substituent such as optionally substituted alkyl, alkenyl, alkynyl or aryl. Particularly preferred links that can be used to distance the active moiety from the DNA binding portion of the molecule include methyl, acetyl, ethenyl, cycloalkenyl, aryl, alkynyl and dienyl. FIG. 17 shows exemplary general structures of compounds of the invention useful for imaging purposes, where the active moiety ("I") is distanced from the DNA minor groove binding portion of the compound. As can be seen from FIG. 17, distancing of the active moiety can be achieved is by utilising substituents on the terminal phenyl group of the ligand to form a naphthyl group or to produce a tribenzimidazole structure. Table 2 indicates another strategy for imaging-only; namely the use of isotopes (such as $^{72}$As, $^{73}$Se, $^{66}$Ga) with a high positron yield but negligible Auger yield.

The conjugates of the invention may also, as mentioned above, incorporate one or more photoactive moiety, thus allowing them to be utilised in photochemotherapy. Photodynamic therapy (PDT) has its origins in the discovery that certain porphyrin derivatives are preferentially taken up by tumour cells following systemic administration and that they also act as photosensitisers. If porphyrin treated cells are exposed to light (more specifically to that part of the spectrum corresponding to their absorption maximum; namely around 500-600 nanometers), they are killed by doses of light that are otherwise not cytotoxic. Accordingly, the combination of systemic administration of porphyrin derivatives and exposure to light (usually from a laser source) provides a basis for PDT of some forms of cancer (Dolmans et al., 2003). The term photodynamic therapy usually refers to the particular combination of visible light and porphyrins, and is therefore a special case of photochemotherapy. A number of porphyrin derivatives have been used in PDT. For example, Photofrin, a porphyrin derivative, has FDA approval for use in PDT of various forms of cancer. A porphyrin precursor, aminolevulinic acid is preferentially incorporated into porhyrins synthesised de novo in neoplastic lesions, after systemic administration, and this is also an FDA-approved sensitiser for PDT. A further manifestation of PDT is in combination with antibody targeting, using the porphrin-immunoconjugates of internalising antibodies (Vrouenraets et al., 2000) such as anti-EGFR (Soukos et al., 2001).

In general, the porphyrins used in photodynamic therapy are not DNA binding drugs, but instead have been shown to locate into cytoplasmic structures (eg mitochondria). However, the DNA intercalating psoralens are known to sensitise DNA and cells to $UV_A$ irradiation. Indeed, photochemotherapy using psoralen (mainly 8-methoxypsoralen) and $UV_A$ is widely used in dermatology, particularly for the treatment of psoriasis by oral or topical administration of psoralen followed by $UV_A$ irradiation (Honigsmann, 2001; Parrish et al., 1974) and cutaneous T-cell lymphoma (CTCL) by extracorporeal photopheresis (Edelson et al., 1987; Heald et al., 1992).

Iodinated minor groove binding bibenzimidazole ligands are known to efficiently sensitise DNA and cells to $UV_A$ irradiation (Martin et al., 1994; Martin et al., 1990). $UV_A$ corresponds to the part of the UV visible spectrum that coincides with the % max of the bibenzimidazoles, namely 350 nm. $UV_A$ irradiation of the DNA-ligand complex results in dehalogenation with the formation of a ligand radical species, which induces strand breaks in DNA, with cytotoxic consequences (Martin et al., 1990). Photoactive ligands or moieties may therefore be incorporated in the conjugates of the invention to be used in a strategy for specific elimination of target cells (eg. tumour cells), which could be described as DNA-directed photochemotherapy. However, at least when using halogenated bibenzimidazoles (eg iodoHoechst 33258) as the photoactive moiety bearing DNA ligand, and as the activating light is in the $UV_A$ region and is therefore less penetrating than the visible light used in conventional PDT, this strategy has particular utility for elimination of superficial cells, or in ex-vivo PDT (for example for purging stem cell preparations) where a sample including cells to be eliminated is removed from the patient to be treated and then subsequently returned, substantially purged of the target cells.

Examples of other photoactive moieties that may be incorporated within the conjugates of the invention include thiohydroxamic acid (that gives rise to Barton esters) and xanthate esters, as shown below where R represents alkyl and where the representation of the Barton ester depicts the substituent on a phenyl ring of the ligand according to the invention.

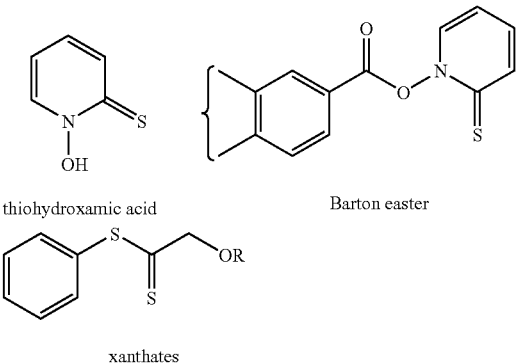

thiohydroxamic acid      Barton easter xanthates

The active moieties of the invention may be bound to the DNA ligand using a variety of chemical approaches, depending upon the nature of the active moiety concerned. However, in the case where the active moiety is a radioactive iodine atom, and where the DNA ligand includes a carboxylic acid or carbonyl moiety useful for conjugation of a target cell specific protein or peptide, then one convenient approach adopted by the present inventors is to employ the iododestannylation reaction for introduction of the radioactive atom. The intermediate compound includes a trialkylstannyl moiety (for example trimethylstannyl) at the site of intended location of the active moiety. For example, the trialkylstannyl moiety can then be substituted with a radioactive atom such as iodine, most preferably $I^{124}$.

Methods according to the invention can be utilised for imaging and therapy of patients suffering from or suspected of suffering from cancers or other cellular abnormalities of a wide variety of types, such as those affecting bladder, breast, prostate, cervix, uterus, ovary, testicle, colorectal, endometrial, brain, throat, lung, skin, lymphatic, kidney, pancreas, neuroendocrine, blood or bone cells or tissue, for example.

The conjugates of the invention may be administered for therapy by any suitable route. It will be understood that the conjugates are preferably administered via a route allowing effective uptake by the target cells of interest. Suitable routes of administration may include oral, rectal, nasal, inhalation of aerosols or particulates, topical (including buccal and sublingual), transdermal, vaginal, intravesical and parenteral (including subcutaneous, intramuscular, intravenous, intrasternal, intrathecal, epidural and intradermal). Preferably, administration of the conjugates will be direct injection into the target cells, such as direct injection into a solid tumour. In other preferred embodiments of the invention, the conjugates are administered via the oral route or by the transdermal route. However it will be appreciated that the preferred route will vary with the condition and age of the subject, the nature of the nature of the target cells intended to be imaged or eliminated, their location within the subject and the judgement of the physician or veterinarian.

As used herein, an "effective amount" refers to an amount of conjugate that provides the desired cell killing or imaging activity when administered according to a suitable dosing regime. For example, dosing may occur at intervals of minutes, hours, days, weeks or months. Suitable dosage amounts and regimes can be determined by the attending physician or veterinarian. For example the conjugates may be administered as a single dose, by infusion over a suitable time period or as multiple doses at separate times, preferably at regular intervals. For example, the conjugates may be administered in amounts of between about 10 µg/kg to about 500 mg/kg, preferably between about 100 µg/kg to about 100 mg/kg. Naturally the administration amounts may be varied if administration is conducted more or less frequently, such as by continuous infusion, by regular dose every few minutes or by administration every 10, 20, 30 or 40 minutes or every 1, 2, 3, 4, 6, 8, 10, 12, 16 or 24 hours, for example.

The present invention also relates to compositions comprising the conjugates, optionally in conjunction with other active agents such as chemotherapeutic agents, analgesic agents, targeted radio- or photo-protective agents or other agents useful to treat symptoms or complications of the disease the patient is suffering from, together with one or more pharmaceutically acceptable additives. The pharmaceutically acceptable additives may be in the form of carriers, diluents, adjuvants and/or excipients and they include all conventional solvents, dispersion agents, fillers, solid carriers, coating agents, antifungal or antibacterial agents, dermal penetration agents, surfactants, isotonic and absorption agents and slow or controlled release matrices. The conjugates may be presented in the form of a kit of components adapted for allowing concurrent, separate or sequential administration. Each carrier, diluent, adjuvant and/or excipient must be "pharmaceutically acceptable" in the sense of being compatible with the other ingredients of the composition and physiologically tolerated by the subject. The compositions may conveniently be presented in unit dosage form and may be prepared by methods well known in the art of pharmacy. Such methods include the step of bringing into association the conjugate with the carrier, which constitutes one or more accessory ingredients. In general, the compositions are prepared by uniformly and intimately bringing into association the conjugate with liquid carriers, diluents, adjuvants and/or excipients or finely divided solid carriers or both, and then if necessary shaping the product.

Compositions of the present invention suitable for oral administration may be presented as discrete units such as capsules, sachets or tablets each containing a predetermined amount of the conjugate; as a powder or granules; as a solution or a suspension in an aqueous phase or non-aqueous liquid; or as an oil-in-water liquid emulsion or a water-in-oil emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (eg. sodium starch glycollate, cross-linked povidone, cross-linked sodium carboxymethyl cellulose) surface-active or dispersing agent. Moulded tablets may be made my moulding in a suitable machine a mixture of the powdered compound moistened with an inert liquid diluent. The tablets may optionally be coated or scored and may be formulated so as to provide slow or controlled release of the conjugate therein using, for example, hydroxypropylmethyl cellulose in varying proportions to provide the desired release profile. Tablets may optionally be provided with an enteric coating, to provide release in parts of the gut other than the stomach.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspended agents and thickening agents. The compositions may be presented in a unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions suitable for topical administration to the skin, ie transdermal administration, may comprise the active agents dissolved or suspended in any suitable carrier or base and may be in the form of lotions, gels, creams, pastes, ointments and the like. Suitable carriers may include mineral oil, propylene glycol, waxes, polyoxyethylene and long chain alcohols. Transdermal devices, such as patches may also be used and may comprise a microporous membrane made from suitable material such as cellulose nitrate/acetate, propylene and polycarbonates. The patches may also contain suitable skin adhesive and backing materials.

The conjugates may also be presented as implants, which may comprise a drug bearing polymeric device wherein the polymer is biocompatible and non-toxic. Suitable polymers may include hydrogels, silicones, polyethylenes and biodegradable polymers.

The conjugates of the invention may be administered in a sustained (ie controlled) or slow release form. A sustained release preparation is one in which the conjugate is slowly released within the body of the subject once administered and maintains the desired concentration over a minimum period of time. The preparation of sustained release formulations is well understood by persons skilled in the art. Dosage forms may include oral forms, implants and transdermal forms. For slow release administration, the conjugates may be suspended as slow release particles or within liposomes, for example.

It should be understood that in addition to the ingredients particularly mentioned above, the compositions of this invention may include other agents conventional in the art, having regard to the type of composition in question. For example, agents suitable for oral administration may include such further agents as binders, sweetners, thickeners, flavouring agents, disintegrating agents, coating agents, preservatives, lubricants and/or time delay agents.

Other details of pharmaceutically acceptable carriers, diluents and excipients and methods of preparing pharmaceutical compositions and formulations are provided in Remmington's Pharmaceutical Sciences 18$^{th}$ Edition, 1990, Mack Publishing Co., Easton, Pa., USA, the disclosure of which is included herein in its entirety by way of reference.

The conjugates for use in the invention may also be presented for use in veterinary compositions. These may be prepared by any suitable means known in the art. Examples of such compositions include those adapted for:

(a) oral administration, eg drenches including aqueous and non-aqueous solutions or suspensions, tablets, boluses, powders, granules, pellets for admixture with feedstuffs, pastes for application to the tongue;
(b) parenteral administration, eg subcutaneous, intramuscular or intravenous injection as a sterile solution or suspension;
(c) topical application, eg creams, ointments, gels, lotions, etc.

In addition to administration of the conjugates of the invention to patients for the purpose of therapeutic treatment (ie. to eliminate specific cells, such as tumour cells) the conjugates may also be utilised in imaging of target cells and in ex vivo purging of target cells from a sample of cells extracted from a patient. These aspects of the invention will be discussed further below.

As conveyed above, the present invention relates to methods of imaging and eliminating target cells within a patient and to ex-vivo purging of target cells obtaining from a patient, where it is intended that the patient is a mammal. In this context the term "mammal" is intended to encompass both humans and other mammals such as laboratory animals including rats, mice, simians and guinea pigs, domestic animals including cats, dogs, rabbits, agricultural animals including cattle, sheep, goats, horses and pigs and captive wild animals such as lions, tigers, elephants and the like.

There are a number of clinical scenarios in which cells (for example within peripheral blood or bone marrow samples) are removed from a patient and fractionated or treated in some way to remove particular components, or are enriched for others, with the altered population subsequently being returned to the patient. For lymphoma patients treated with high dose chemotherapy (HDC) (which is sometimes combined with radiotherapy), the intensity of the treatment is such that there is a high probability that all the haemopoietic stem cells in the patient could be ablated. Accordingly, haemopoietic stem cells (in bone marrow, or "mobilised" into peripheral blood) are removed and stored prior to HDC, and returned to the patient after therapy to "rescue" the haemopoietic system. However an impediment to the success of this strategy is the possibility that the pre-treatment stem cell sample might also contain tumour cells, which can re-colonise in the patient in parallel with growth of the stem cell graft. Thus, various ex vivo treatments have been explored aimed at "purging" any contaminating tumour cells from the stem cell samples Approached such as this are generally referred to as "ex vivo purging". Clearly, such purging treatments require selective removal or killing of tumour cells, in preference to haemopoietic stem cells or other normal cells.

Early purging strategies involved the use of cytotoxic agents such as 4-hydroperoxycyclophosphamide (Roecklein et al., 1998), or photosensitising dyes (Miyagi et al., 2003), with an apparent or empirical selectivity, now surpassed by the specificity of antibody-based approaches.

Although positive selection for cells on the basis of markers associated with normal stem cells (eg. CD34) can achieve a de facto depletion of tumour cells, negative selection against tumour cell markers is the more usual strategy. However both can be used in combination (Mohr et al., 2001). For negative selection, target tumour antigens include CD33 for AML (Duzkale et al., 2003) and B- and T-cell markers such as CD20, sometimes used in a cocktail (Friedberg et al., 2003; Mohr et al., 2001), are used in purging strategies for patients with non-Hodgkins lymphoma. For breast epithelial cancers c-erB2 has been used as a target tumour-specific antigen (Spyridonidis et al., 1998).

The mode of use of antibodies varies considerably in existing purging approaches. In some cases the antibodies are conjugated to magnetic beads (Mohr et al., 2001) or high-density micro particles (Friedberg et al., 2003; Webb et al., 2002) providing a means for physical removal of targeted cells from the stem cell preparation. Another approach is use of immunotoxins to eliminate tumour cells (Duzkale et al., 2003; Spyridonidis et al., 1998), and in some cases the innate toxicity of the antibody per se is sufficient for the antibodies to be used without conjugation. In the present invention, however, the conjugate will comprise an active moiety (as discussed above) to initiate DNA damage and cell death in the selected cells, as well as a cell targeting protein or peptide, such as an antibody or antibody fragment, that binds to receptors up regulated on the surface of the target cells concerned and gives rise to internalisation of the conjugate-receptor complex.

The use of radioisotopes for tumour imaging plays a significant role in radiological detection of tumours, with the other generally available imaging modalities including conventional (X-ray) radiology, Computerised Tomography (CT), ultrasound and Magnetic Resonance Imaging (MRI). The radioisotopes used for imaging are gamma emitters, detected most efficiently with Single Photon Emission Computed Tomography (SPET), which provides an image of the quantitative distribution of the injected isotope in the body. In some special cases the imaging agent is the radionuclide itself. This is enabled through a specific chemical affinity between the radionuclide and the target cells. Thus radioactive iodide ($^{131}$I, and more recently $^{123}$I) is used to image thyroid and thyroid tumours. Similarly, $^{67}$Ga-citrate is used for imaging some tumours via gallium exchanges with iron in transferrin, where increased $^{67}$Ga uptake by tumours reflects up-regulation of TF receptors. More generally, imaging agents are comprised of a gamma-emitting radioisotope conjugated to a tumour protein or molecule with tumour cell affinity, for example MFE23 (a recombinant anti-CEA antibody) labelled with $^{123}$I (Chester et al., 2000). In some cases, imaging is used as a prelude to radioimmunothereapy, to confirm tumour targeting and to obtain data for dosimetry calculations, as exemplified by $^{86}$Y- and $^{90}$Y-trastuzumab (Herceptin) (Palm et al., 2003).

A very important development in radioisotope imaging is Positron Emission Tomography (PET). Positrons undergo an annihilation reaction that produces 2 gamma photons, that emanate from their source at an angle of close to 180° from each other. The simultaneous detection of pairs of gamma photons provides the basis for computing a high resolution image; much better than that from a conventional gamma camera. Most of the currently available positron-emitting isotopes have very short half-lives; for example $^{11}$C (half-life, 20 min), $^{15}$O (2 min) and $^{18}$F (110 min), which means that although they may be used they provide a challenge for timely labelling and purification. Another limitation of the short half-life stems from the kinetics of labelled antibody distribution. At least several hours, and even 1 or 2 days, are required for clearance of the labelled agent from blood, in order to get maximum tumour/blood isotope ratios, and this has prompted interest in longer-lived PET nuclides (Verel et al., 2003b). Nevertheless $^{18}$F-deoxyglucose has proven to be very useful agent for imaging tumours, on the basis of metabolic activity, and $^{18}$F-FLT (fluorodeoxythymidine) on the basis of proliferation rate (Shields et al., 1998). In addition,

[124]I is a positron emitter, which has only become available relatively recently. It has a half-life of 4.2 days and some encouraging results have been reported for imaging tumour angiogenesis with [124]I-antiVEGF (Collingridge et al., 2002). Even more recently, [89]Zr-trastuzumab has been proposed as a PET imaging agent, in conjunction with therapy with $^{90}$Y-trastuzumab (Verel et al., 2003a). Any of the above mentioned radioisotopes, and particularly the gamma- and/or positron emitters can be incorporated within the conjugates of the present invention by the chemical approaches herein discussed to enable use of the conjugates in imaging of tumour or other target cells.

Throughout this specification it is to be understood that the invention has been described by way of example only and that modifications and/or alterations that would be obvious to a person skilled in the art based upon the disclosures herein are also considered to fall within the scope of the present invention.

The invention will now be described further with reference to the following non-limiting examples:

EXAMPLES

Examples 1 to 4

Synthesis of the Bibenzimidazole DNA Ligand Derivatives Used to Prepare the Radioactively Labelled Precursors of the Labelled Conjugates Examples 1 to 4 describe the synthesis of bibenzimidazole ligands, and intermediates required to synthesise those ligands. The ligands are designed so as to contain two quite separate functionalities:

A moiety through which the ligand can be subsequently linked to a protein. In the examples these conjugated groups are either a carboxylic acid moiety (a precursor to an amide link), or a carbonyl moiety (a precursor to a hydrazide linkage). There are other moieties that could be used to similar effect, and A moiety, which will facilitate the introduction of radioactive atom. In the examples described, a tri-alkyl stannyl moiety is used as a precursor to the introduction of a radioactive iodine atom, in the reaction described as iodo-destannylation. Other moieties could be used to similar effect, for example a chelating moiety as a precursor for labelling with a radioactive metal such as [67]Ga.

The use of the described DNA ligand derivatives to prepare radioactive conjugates will be described in later examples.

Example 1

3-Trimethylstannyl-1-{5'-[5''-(piperazin-1'''-yl)benzimidazol-2''-yl]benzimidazol-2'-yl}benzene (1)

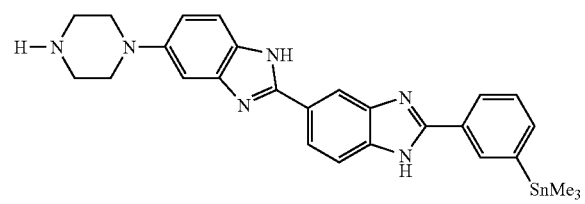

Nitroamine (14) (1.42 g, 4.20 mmol) in 1:4 methanol/ethyl acetate (150 ml) was hydrogenated in the presence of 5% palladium on carbon (0.801 g) at atmospheric pressure for 6 h, after which the suspension was filtered through celite, and concentrated to give the diamine intermediate as a pale orange solid. Sodium metabisulphite (1.21 g, 6.37 mmol) in 1:1 ethanol/water (40 ml) was added to 3-(trimethylstannyl) benzaldehyde (10) (1.70 g, 6.32 mmol) in ethanol (40 ml), and the mixture was heated over a steam bath for 10 min or until homogeneous. The diamine in ethanol (40 ml) was added to the aldehyde/metabisulphite complex, and the stirred mixture was heated at reflux under nitrogen for 20 h after which it was cooled to room temperature. Concentrated ammonia solution (~28%) was added until the pale yellow suspension became basic (pH~10). The suspension was chilled in an ice/water bath for 5.5 h, then left to stand at 4° overnight. The suspension was filtered and washed with water. No residue was collected, but the filtrate became milky. The filtrate was left to stand in an ice bath for 3 h (the side of the flask was scratched to promote crystallization), then at room temperature for 2 days. The resultant fine yellow suspension was filtered, washed with water, then with ether, and was dried at the water pump to give 3-trimethylstannyl-1-{5'-[5''-(piperazin-1'''-yl)benzimidazol-2''-yl]benzindazol-2'-yl}benzene (1) as a pale yellow solid (1.73 g, 74%) m.p. 203° dec.

$^1$H nmr (400 MHz, d-4-MeOH/d1-TFA): δ 0.40 (s, with Sn satellites d J 54.5 Hz, 9H) SnMe$_3$; 3.45 (m, 4H) pip-CH$_2$; 3.56 (m, 4H) pip-CH$_2$; 7.35 (d, J 2.0 Hz) H4''; 7.46 (dd, J 8.8, 2.0 Hz, 1H) H6''; 7.69 (t, J 7.6 Hz, 1H) H5; 7.77 (d, J 8.8 Hz, 1H) H7''; 7.92 (d, J 7.6 Hz, 1H) H6; 8.11 (m, 2H) H4, H7'; 8.23 (dd, J 8.6, 1.7 Hz, 1H) H6'; 8.36 (brs, 1H) H2'; 8.56 (brs, 1H) H4'.

Electrospray mass spect.: m/z 559 (Sn$^{120}$ M$^+$+1, 100%); 557 (Sn$^{118}$ M$^+$+1, ~71%). Found: Sn$^{120}$ M$^+$+1, 559.1627; Sn$^{118}$ M$^+$+1, 557.1616. C$_{27}$H$_{30}$N$_6$Sn$^{120}$ requires M$^+$+1, 559.1632; C$_{27}$H$_{30}$N$_6$Sn$^{118}$ requires M$^+$+1, 557.1626.

Dependant Syntheses for Example 1

3-Iodobenzyl Alcohol (11)

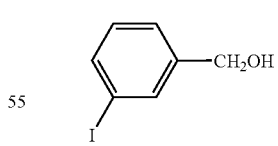

Ethyl chloroformate (1.02 g, 11.1 mmol) in dry tetrahydrofuran (5 ml) was added slowly over 10 min to a stirred solution of 3-iodobenzoic acid (1.98 g, 7.98 mmol) and triethylamine (0.500 g, 11.6 mmol) in dry tetrahydrofuran at −8° (ice/salt/water bath). The yellow mixture soon became cloudy. It was shielded from light and stirred at −8° for 0.5 h, after which it was filtered to remove the triethylammonium chloride precipitate. The filtrate was added slowly to a suspension of sodium borohydride (0.795 g, 21.1 mmol) in water (30 ml) in a three necked flask, equipped with a thermometer, and connected to nitrogen, making sure that the temperature of the mixture is kept below 10° during the addition. Gas evolution (carbon dioxide) was observed. After the addition was completed, the mixture was stirred, shielded from light, at room temperature for 22 h under nitrogen. The resultant cloudy mixture was acidified with aqueous hydrochloric acid (10%) to pH~1. The layers were separated, and the aqueous layer was extracted with ether (×3). The combined ether extract and tetrahydrofuran layer was washed with aqueous sodium hydroxide (×1, 10%) and then with water (×1). Drying with magnesium sulphate, and concentration gave 3-iodobenzyl alcohol (11) a pale yellow oil (1.02 g, 54%).

$^1$H nmr (400 MHz, CDCl$_3$): δ4.66 (s, 2H)CH$_2$; 7.10 (brt, J 7.7 Hz, 1H) H5; 7.32 (brd, J 7.7 Hz, 1H) H6, 7.63 (brd, J 7.7 Hz, 1H) H4; 7.74 (brs, 1H) H2.

3-Iodobenzaldehyde (12)

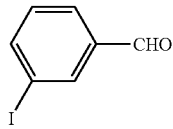

A suspension of pyridinium chlorochromate (2.45 g, 11.4 mmol) and dry celite (~2.00 g) in dry dichloromethane (20 ml) was stirred at room temperature for 15 min. 3-Iodobenzyl alcohol (11) (1.02 g, 4.35 mmol) in dry dichloromethane (5 ml) was added. The suspension was shielded from light and stirred at room temperature for 2 h after which it was diluted with ether, and filtered through celite. The cloudy brown filtrate was concentrated to a red-brown gummy paste which was re-dissolved in dichloromethane and passed through a short silica column, eluting with dichloromethane. This gave a clear, colourless solution which was concentrated to give 3-iodobenzaldehyde (12) as a white solid (0.953 g, 95%).

$^1$H nmr (400 Mz, CDCl$_3$): δ7.29 (t, J 7.8 Hz, 1H) H5; 7.85 (brd, J 7.8 Hz, 1H) H6; 7.96 (brd, J 7.8 Hz, 1H) H4; 8.21 (brs, 1H) H2; 9.93 (s, 1H) CHO.

3-(Trimethylstannyl)benzaldehyde (10)
(Harapanhalli, et al. 1996)

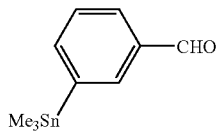

A mixture of 3-iodobenzaldehyde (12) (1.00 g, 4.33 mmol), hexamethylditin (2.18 g, 6.65 mmol) and tetrakis(triphenylphosphine)palladium(0) (0.220 g, 0.19 mmol) in dry dioxane (50 ml) was shielded from light and stirred at reflux under nitrogen for 2 h. The pale yellow suspension soon became dark brown, and eventually became a clear solution with suspended palladium residue. After cooling to room temperature, the suspension was filtered through celite and concentrated to a pale yellow, cloudy oil (2.364 g). This was purified by flash column chromatography (the silica column first having been pre-equilibrated with light petrol) eluting with 9:1 light petrol/ether. The second main fraction (R$_F$~0.5, silica plates, light petrol) containing the product 3-(trimethylstannyl)benzaldehyde (10) was collected and concentrated to a colourless oil (0.891 g, 77%).

$^1$H nmr (300 MHz, CDCl$_3$): δ 0.34 (s, with Sn satellites d, J 54.5 Hz, 9H) SnMe$_3$; 7.50 (t, J 7.5 Hz, 1H) H3; 7.75 (brd, J 7.5 Hz, 1H) H4; 7.80 (dt, J 7.5, 1.5 Hz, 1H) H2; 8.0 (brs, 1H) H6; 10.03 (s, 1H) CHO.

5-(piperazin-1'-yl)-2-nitroaniline (13)

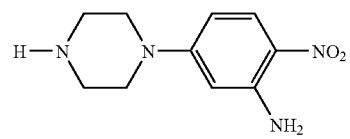

A mixture of 5-chloro-2-nitroaniline (5.10 g, 29.5 mmol), piperazine (12.6 g, 147 mmol) and anhydrous potassium carbonate (4.10 g, 29.7 mmol) in anhydrous N,N-dimethylacetamide (50 ml) was stirred at ~120° for 21 h. After cooling to room temperature, the red-brown mixture was poured into crushed ice. The resultant orange suspension was extracted with dichloromethane (×5). The combined organic extract was re-extracted into aqueous hydrochloric acid (×2, 5%). The combined orange aqueous phase was washed with dichloromethane and collected. Aqueous sodium hydroxide (30%) was added at 0° until pH~10. A yellow precipitate started to form. The suspension was stirred at 0° for 45 min, and then left to stand at room temperature over the weekend before filtration. The crystalline yellow solid residue was washed with water, then with ether, and dried at the water pump. This was followed by further drying under vacuum in a dessicator for 20 h to give 5-(piperazin-1'-yl)-2-nitroaniline (13) (5.43 g, 84%) m.p. 166-9° (lit. 177-8°, lit. 170°).

$^1$H nmr (300 MHz, d4-MeOH/d1-TFA): δ 3.33 (m, 4H) H3', H5'; 3.56 (m, 4H) H2', H6'; 6.27 (d, J 2.7 Hz, 1H) H6; 6.39 (dd, J 9.8, 2.7 Hz, 1H) H4; 7.97 (d, J 9.8 Hz, 1H) H3.

4-[5 (piperazin-1"-yl)benzimidazol-2'-yl]-2-nitroaniline (14)

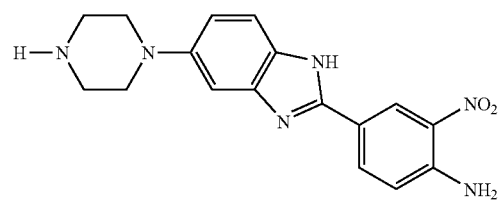

Nitroamine (13) (2.00 g, 9.01 mmol) in 1:4 methanol/ethyl acetate (150 ml) was hydrogenated in the presence of 5% palladium on carbon (0.400 g) at atmospheric pressure for 3.5 h. The suspension was quickly filtered and concentrated to give the diamine intermediate as a yellow solid. This was reacted immediately with (4) (2.24 g, 9.12 mmol) in dry ethanol (40 ml) and glacial acetic acid (20 ml) by heating the stirred suspension at reflux under nitrogen for 18 h. After cooling to room temperature, the orange suspension was concentrated to an orange paste and dissolved in water (~150 ml). Concentrated ammonia solution (~28%) was added until a gummy red precipitate formed. The precipitate became less gummy and more crystalline after standing overnight. The red suspension was filtered, and the red solid was washed with plenty of water. After drying at the water pump for ~3 min, the red solid was transferred to a conical flask, and dissolved in 1:12 glacial acetic acid/methanol (60 ml). The solution was filtered to remove any insoluble impurities. Concentrated ammonia solution (~28%) was added to the red filtrate until it is basic, and became cloudy. Crystallization was promoted by scratching the side of the flask and the suspension was allowed to stand for 2 days before filtration. The residue was washed with water, then with ether, to give product (14) as red microneedles (2.62 g, 86%) m.p. darkened at 190°, melted at 258-64°. Recrystallization from ethanol gave 4-[5'-(piperazin-1"-yl)benzimidazol-2'-yl]-2-nitroaniline (14) as clusters of red microneedles (2.32 g, 76%) m.p. 164° dec.

$^1$H nmr (300 MHz, d4-MeOH/d1-TFA): δ 3.43 (m, 2H) H3", H5"; 3.51 (m, 2H) H2", H6"; 7.24 (d, J 2.5 Hz, 1H) H4'; 7.25 (d, J 9.0 Hz, 1H) H6; 7.37 (dd, J 9.0, 2.5 Hz, 1H) H5; 7.66 (d, J 9.0 Hz, 1H) H7'; 7.97 (dd, J 9.0, 2.5 Hz, 1H) H6'; 8.96 (d, J 2.5 Hz, 1H) H3.

Example 2

3-Trimethylstannyl-1-{5'-[5"-(4'''-(1''''-oxy-4''''-carboxybut-1-yl)piperazin-1'''-yl)benzimidazol-2"-yl]benzimidazol-2'-yl}benzene (2)

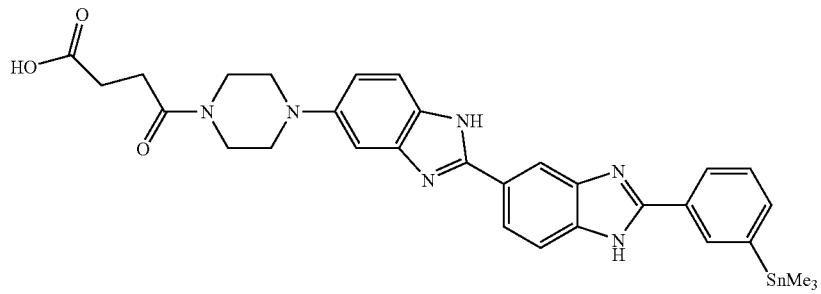

A mixture of compound (1) (0.053 g, 0.094 mmol), potassium carbonate (0.021 g, 0.150 mmol) and succinic anhydride (0.014 g, 0.139 mmol) in dry N,N-dimethylformamide (or N,N-dimethylacetamide) (1 ml) was stirred at room temperature for 4 h after which it was concentrated to a sticky brown solid. This was washed with ether and pumped down to a yellow solid (contains succinic acid and potassium carbonate).

$^1$H mm (400 MHz, d4-MeOH/d1-TFA): δ 0.41 (s, with Sn satellites d J 55.7 Hz, 9H) SnMe$_3$; 2.64 (brt, J~6.3 Hz, 2H) H2''''; 2.74 (brt, J~6.3 Hz, 2H) H3''''; 3.39 (m, 2H) pip-CH$_2$; 3.81 (m, 4H) pip-CH$_2$; 7.26 (d, J 2.1 Hz, 1H) H4"; 7.44 (dd, J 9.0, 2.1 Hz, 1H) H6"; 7.66 (t, J 7.7 Hz, 1H) H5; 7.73 (d, J 9.0 Hz, 1H) H7"; 7.92 (d, J 7.7 Hz, 1H) H6; 8.11 (m, 2H) H4, H7'; 8.24 (dd, J 9.0, 2.1 Hz, 1H) H6'; 8.36 (d, J 2.1 Hz, 1H) H2; 8.57 (brs, 1H) H4'.

Dependant Syntheses for Example 2

Levulinic Anhydride (15)

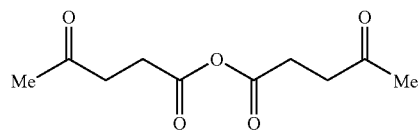

A solution of dicyclohexylcarbodiimide (0.084 g, 0.216 mmol) in dichloromethane (1 ml) was added to a solution of levulinic acid (0.047 g, 0.406 mmol) in dichloromethane (2 ml). A white crystalline solid of dicyclohexylurea formed immediately. The suspension was allowed to stand at room temperature for 30 min, then chilled in an ice bath for 3 h min, and left to stand at 4° overnight before filtration. The colourless filtrate was concentrated to give a colourless oil with a small amount of suspended white solid of dicyclohexylcarbodiimide (DCC) and dicyclohexylurea (DCU). This was used as crude in the preparation of (3).

$^1$H nmr (400 MHz, CDCl$_3$): δ 2.20 (s, 6H) Me×2; 2.72 (t, J 6.2 Hz, 4H)CH$_2$-keto; 2.79 (t, J 6.2 Hz, 4H)CH$_2$-carboxy.

DCC: δ 1.30, 1.73, 1.92, 3.19 (all m, 22H) dicyclohexyl.

DCU: δ 1.30, 1.73, 1.92, 3.19 (all m, 22H) dicyclohexyl; 1.57 (m, 2H) NH.

Levulinic acid: δ 2.20 (s, 6H) Me×2; 2.63 (t, J 6.2 Hz, 4H)CH$_2$-keto; 2.75 (t, J 6.2 Hz, 4H)CH$_2$-carboxy.

Example 3

3-Trimethylstannyl-1-{5'-[5''-(4'''-(1'''',5''''-dioxo-pent-1-yl)piperazin-1'''-yl)benzimidazol-2''-yl]benzimidazol-2'-yl}benzene (3)

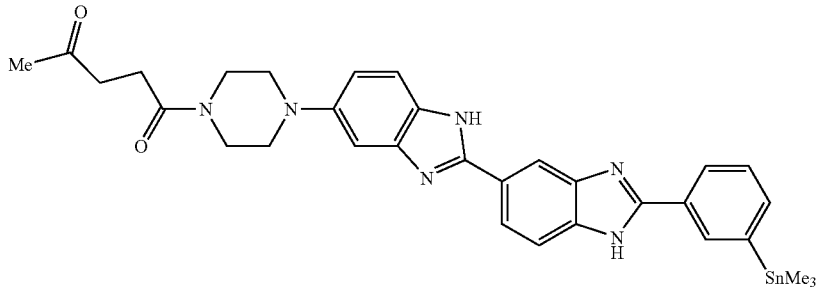

A mixture of compound (1) (0.066 g, 0.118 mmol), potassium carbonate (0.045 g, 0.329 mmol) and levulinic anhydride (15) (0.069 g, 0.203 mmol) in dry N,N-dimethylformamide (2 ml) was stirred at room temperature for 20 h after which it was concentrated to a sticky brown solid. This was washed with ether and plenty of aqueous ammonia solution (28%), and again with ether, and then pumped down to a yellow solid (0.049 g, contains DCU).

$^1$H nmr (400 MHz, d4-MeOH/d1-TFA): δ 0.41 (s, with Sn satellites d J 55.7 Hz, 9H) SnMe$_3$; 2.20 (s, 3H)CH$_3$CO; 2.704 (brt, J~6.0 Hz, 2H) H2''''; 2.82 (brt, J 6.0 Hz, 2H) CH$_2$H3''''; 3.80 (m, 4H) pip-CH$_2$; 7.26 (d, J 1.9 Hz, 1H) H4''; 7.46 (dd, J 9.3, 1.9 Hz, 1H) H6''; 7.70 (t, J 7.6 Hz, 1H) H5; 7.74 (d, J 9.3 Hz, 1H) H7''; 7.95 (brd, J 7.6 Hz, 1H) H6; 8.12 (brd, J 7.6 Hz, 2H) H4; 8.13 (d, J 8.7 Hz, 2H) H7'; 8.26 (dd, J 8.7, 1.5 Hz, 1H) H6'; 8.35 (d, J 1.8 Hz, 1H) H2; 8.57 (d, J 1.5 Hz, 1H) H4'.

Example 4

3-Tributylstannyl-1-{5'-[5''-(piperazin-1'''-yl)benzimidazol-2''-yl]benzimidazol-2'-yl}benzene (4)

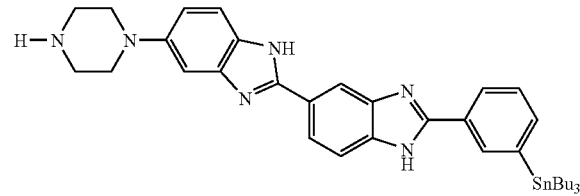

Nitroamine (14) (0.678 g, 2.01 mmol) in 1:4 methanol/ethyl acetate (200 ml) was hydrogenated in the presence of 5% palladium on carbon (0.459 g) at atmospheric pressure for 4 h. The suspension was quickly filtered through celite, and concentrated to give the diamine intermediate as a pale yellow solid. Sodium metabisulphite (1.23 g, 6.96 mmol) in 1:1 ethanol/water (40 ml) was added to 3-tributyltinbenzaldehyde (16) (2.33 g, 5.91 mmol) in ethanol (40 ml) and the mixture was heated over a steam bath for 10 min or until homogeneous. The diamine in ethanol (50 ml) and tetrahydrofuran (20 ml) was added to the aldehyde/metabisulphite complex. The mixture was heated at reflux, with stirring, under nitrogen for 19 h after which it was cooled to room temperature. Concentrated ammonia solution (~28%) was added until the yellow suspension became basic (pH~10). The suspension was chilled in an ice/water bath for 3 h and left to stand at room temperature overnight before it was filtered and washed with water. No product residue was collected. The cloudy filtrate was chilled in ice for 4 h and left to stand at room temperature overnight. A milky liquid remained together with orange oil globules that sank to the bottom of the flask. A small portion was triturated with ethyl acetate, and a yellow precipitate began to form. This was allowed to stand overnight before filtration and washing with ether to give 3-tributylstannyl-1-{5'-[5''-(piperazin-1'''-yl)benzimidazol-2''-yl]benzimidazol-2'-yl}benzene (4) (0.035 g, 3%) m.p. 215-31°.

The remainder of the mixture could not be triturated similarly, and was extracted with n-butanol (×1), and the combined organic extract was washed with water (×1) and concentrated to a brown viscous oil. The oil was acidified with aqueous hydrochloric acid (10%) until a gummy yellow solid formed. This was made alkaline again with aqueous ammonia solution (28%) and concentrated. The gummy solid was triturated with ether and the ether was centrifuged off. The ether washing was repeated four times. The solid was pumped dry, and washed with aqueous ammonia, then again with ether and pumped dry in a dessicator to give a beige solid (0.152 g). Total yield including the initial precipitate was 0.187 g (14%).

¹H nmr (400 MHz, d4-MeOH/d1-TFA): δ 0.92, 1.23, 1.37, 1.61 (m, 27H) SnBu₃; 3.44 (m, 4H) pip-CH₂; 3.55 (m, 4H) pip-CH₂; 7.36 (d, J 2.2 Hz, 1H) H4"; 7.46 (dd, J 9.2, 2.2 Hz, 1H) H6"; 7.70 (t, J 7.1 Hz, 1H) H5; 7.77 (d, J 9.2 Hz, 1H) H7"; 7.90 (brd, J 7.1 Hz, 1H) H6; 8.12 (m, 2H) H4, H7'; 8.27 (dd, J 9.1, 1.4 Hz, 1H) H6'; 8.32 (d, J 1.8 Hz, 1H) H2; 8.62 (d, J 1.4 Hz, 1H) H4'.

Electrospray mass spect.: m/z 243 (Sn¹²⁰ M⁺+1, 100%); 342 (Sn¹¹⁸ M⁺+1, ~75%). Found: Sn¹²⁰ M⁺+1, 685.3047; Sn¹¹⁸ M⁺+1, 683.3037. C₃₆H₄₈N₆Sn requires Sn¹²⁰ M⁺+1, 685.3041; Sn¹¹⁸ M⁺+1, 683.3035.

The main examples contain a moiety, which can be used to form linkage to a protein, namely:
A carboxylic acid moiety, or
A carbonyl moiety.

The ligands include a non-radioactive iodine atom, substituted into either the meta, para or ortho position of the phenyl ring. The latter position provides maximal photosensitiser activity.

Example 5

3-Iodo-1-{5'-[5"-(4'''-(1''''-oxy-4''''-carboxybut-1-yl) piperazin-1'''-yl)benzimidazol-2"-yl]benzimidazol-2'-yl}benzene (5)

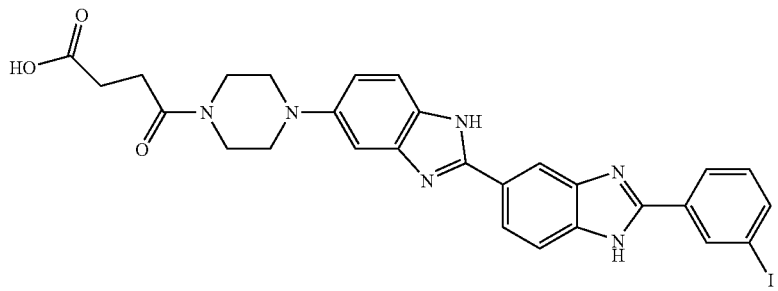

Dependant Syntheses for Example 4

3-(Tributylstannyl)benzaldehyde (16)

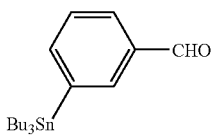

A mixture of 3-iodobenzaldehyde (12) (1.37 g, 5.91 mmol), bis(tributyltin) (5.5 g, 9.49 mmol) and tetrakis(triphenylphosphine)palladium (0) (0.38 g, 0.330 mmol) in dry dioxane (80 ml) was shielded from light and stirred at reflux under nitrogen for 3.5 h. The yellow solution became a black green suspension. After cooling to room temperature, the suspension was filtered through celite and concentrated to a yellow-brown oil. This was purified by flash column chromatography (silica, 9:1 light petrol/ether). The second major band was collected and concentrated to a near colourless oil (4.93 g, >100%).

¹H nmr (400 MHz, CDCl₃): δ 0.91, 1.1, 1.33, 1.50, 1.62 (m, 27H) Bu×3; 7.48 (t, J 7.5 Hz, 1H) H5; 7.72 (brd, J 7.0 Hz, 1H) H4; 7.79 (dt, J 1.4 Hz, 1H) H6; 7.95 (brs, 1H) H2; 10.02 (s, 1H) CHO.

Examples 5 to 9

Synthesis of Derivatives of Iodinated Bibenzimidazole DNA Ligands; Precursors of Conjugates used in DNA-directed Photochemotherapy These examples describe the synthesis of iodinated DNA ligands, and the intermediates required to synthesise same.

A mixture of compound (17) (0.056 g, 0.107 mmol), potassium carbonate (0.029 g, 0.212 mmol) and succinic anhydride (0.021 g, 0.210 mmol) in dry N,N-dimethylformamide (1 ml) was protected from light and stirred at room temperature for 22 h after which it was concentrated to a sticky brown solid. This was washed with ether and pumped down to a brown solid (0.063 g, contains succinic acid and potassium carbonate).

¹H nmr (400 MHz, d4-MeOH/d1-TFA): δ 2.64 (brt, J~6.2 Hz, 2H) H2'''; 2.74 (brt, J~6.2 Hz, 2H) H3''''; 3.38 (m, 2H) pip-CH₂; 3.80 (m, 4H) pip-CH₂; 7.22 (d, J 2.2 Hz, 1H) H4"; 7.41 (dd, J 9.0, 2.2 Hz, 1H) H6"; 7.43 (t, J 8.0 Hz, 1H) H5; 7.70 (d, J 9.0 Hz, 1H) H7"; 7.99 (d, J 8.6 Hz, 1H) H7'; 8.04 (brd, J 8.0 Hz, 1H) H6; 8.10 (dd, J 8.6, 1.8 Hz, 1H) H6'; 8.18 (brd, J 8.0 Hz, 1H) H4; 8.48 (brd, J 1.5 Hz, 1H) H2; 8.58 (brs, 1H) H4'.

Electrospray mass spect.: m/z 621 (M⁺+1, ~8%); m/2z 311 (~26%).

Dependant Syntheses for Example 5

3-Iodo-1-{5'-[5"-(piperazin-4'''-yl)benzimidazol-2"-yl]benzimidazol-2'-yl}benzene (17)

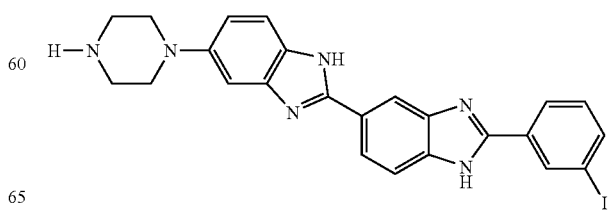

Nitroamine (14) (1.17 g, 3.47 mmol) in 1:4 methanol/ethyl acetate (150 ml) was hydrogenated in the presence of 5% palladium on carbon (0.641 g) at atmospheric pressure for 6 h. The suspension was quickly filtered through celite, and concentrated to give the diamine intermediate as a pale orange solid. Sodium metabisulphite (0.789 g, 6.68 mmol) in 1:1 ethanol/water (40 ml) was added to 4-iodobenzaldehyde (12) (1.50 g, 4.16 mmol) in ethanol (40 ml) and the mixture was shielded from light, and heated over a steam bath for 10 min or until homogeneous. The diamine in ethanol (60 ml) was added to the aldehyde/metabisulphite complex. The mixture was protected from light and heated at reflux, with stirring, under nitrogen for 18 h after which it was cooled to room temperature. Concentrated ammonia solution (~28%) was added until the pale yellow suspension became basic (pH~10). The suspension was stirred in an ice/water bath for 2 h and then left to stand at 4° overnight before filtration. No residue was collected. The filtrate became milky upon washing with water. This was left to stand in an ice bath for 30 min, then left to stand at room temperature overnight. The orange yellow sticky precipitate was with aqueous hydrochloric acid (0.5 M), and re-precipitated with concentrated ammonia solution (~28%) till a loose pale yellow precipitate formed. The suspension was allowed to stand shielded from light at room temperature overnight before filtration. The residue was washed with water, then ether, and dried at the water pump to give 4-iodo-1-{5'-[5''-(4'''-methylpiperazin-1'''-yl)benzimidazol-2''-yl]benzimidazol-2'-yl}benzene (17) as a yellow solid (1.26 g, 70%) m.p. 231-40° dec.

$^1$H nmr (400 MHz, d4-MeOH/d1-TFA): δ 3.45 (m, 4H) pip-CH$_2$; 3.55 (m, 4H) pip-CH$_2$; 7.33 (d, J 2.2 Hz, 1H) H4''; 7.44 (dd, J 9.0, 2.2 Hz, 1H) H6''; 7.46 (t, J 8.4 Hz, 1H) H5; 7.75 (d, J 9.0 Hz, 1H) H7''; 8.03 (d, J 8.6 Hz, 1H) H7'; 8.06 (brd, J 8.4 Hz, 1H) H6; 8.15 (dd, J 8.4, 2.1 Hz, 1H) H6'; 8.18 (brd, J 8.4 Hz, 1H) H4; 8.52 (d, J 1.6 Hz, 1H) H2; 8.59 (brs, 1H) H4'.

Electrospray mass spect.: m/z 521 (M$^+$+1, 100%); m/2z 261 (~83%). Found: M$^+$+1, 521.0942. C$_{24}$H$_{21}$N$_6$ requires M$^+$+1, 521.0950.

Microanalysis found: C, 50.0; H, 4.5; N, 13.9%. C$_{24}$H$_{21}$N$_6$.3H$_2$O requires: C, 50.2; H, 4.7; N, 14.6%.

Example 6

3-Iodo-1-{5'-[5''-(4'''-(1'''',5''''-dioxopent-1-yl)piperazin-1'''-yl)benzimidazol-2''-yl]benzimidazol-2'-yl}benzene (6)

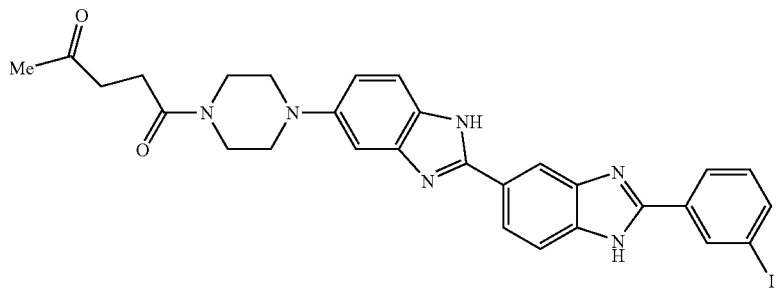

A mixture of compound (17) (0.045 g, 0.087 mmol), potassium carbonate (0.025 g, 0.179 mmol) and levulinic anhydride (15) (0.040 g, 0.187 mmol) in dry N,N-dimethylformamide (4 ml) was protected from light and stirred at room temperature for 21 h after which it was concentrated to a sticky pale brown solid. This was washed with ether and plenty of concentrated ammonia solution (~28%), and then with ether again, and pumped down to a beige solid (0.076 g, contains DCU).

$^1$H nmr (400 MHz, d4-MeOH/d1-TFA): δ 2.20 (s, 3H) MeCO; 2.70 (brt, J~6.2 Hz, 2H) H2''''; 2.82 (brt, J~6.2 Hz, 2H) H3''''; 3.80 (m, 4H) pip-CH$_2$; 7.25 (d, J 1.9 Hz, 1H) H4''; 7.44 (dd, J 8.9, 1.9 Hz, 1H) H6''; 7.48 (t, J 8.0 Hz, 1H) H5; 7.72 (d, J 8.9 Hz, 1H) H7''; 8.05 (d, J 8.6 Hz, 1H) H7'; 8.10 (dd, J 8.0 Hz, 1H) H6; 8.17 (m, 2H) H4, H6'; 8.51 (d, J 0.9 Hz, 1H) H2; 8.59 (brs, 1H) H4'.

Electrospray mass spect.: m/z 619 (M$^+$+1, ~17%).

Example 7

2-Iodo-1-{5'-[5''-(4'''-(1''''-oxy-4''''-carboxybut-1-yl)piperazin-1'''-yl)benzimidazol-2''-yl]benzimidazol-2'-yl}benzene (7)

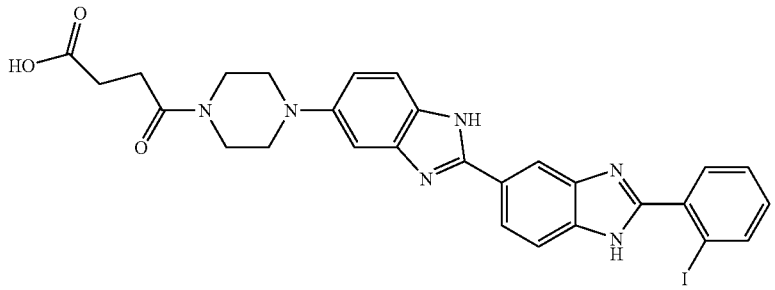

A mixture of compound (18) (0.100 g, 0.190 mmol), and succinic anhydride (0.057 g, 0.570 mmol) in dry N,N-dimethylformamide (2 ml) was protected from light and stirred at room temperature for 22 h after which it was concentrated to a sticky brown solid. This was washed with ether and pumped down to a brown solid (0.064 g, contains succinic acid).

$^1$H nmr (400 MHz, d4-MeOH/d1-TFA): δ 2.65 (m, 2H) H2''''; 2.74 (m, 2H) H3''''; 3.33 (m, 2H) pip-CH$_2$; 3.40 (m, 2H) pip-CH$_2$; 3.81 (m, 4H) pip-CH$_2$; 7.26 (d, J 2.2 Hz, 1H) H4'''; 7.45 (dd, J 9.3, 2.2 Hz, 1H) H6''; 7.48 (td, J 7.8, 1.8 Hz, 1H) H4; 7.70 (brt, J 7.8 Hz, 1H) H5; 7.72 (d, J 9.3 Hz, 1H) H7''; 7.78 (dd, J 7.8, 1.8 Hz, 1H) H6; 8.14 (d, J 8.6 Hz, 1H) H7'; 8.19 (d, J 7.8 Hz, 1H) H3; 8.25 (dd, J 8.6, 1.5 Hz, 1H) H6'; 8.60 (d, J 1.5 Hz, 1H) H4'.

Dependant Syntheses for Example 7

2-Iodo-1-{5'-[5''-(piperazin-1'''-yl)benzimidazol-2''yl]benzimidazol-2'-yl}benzene (18)

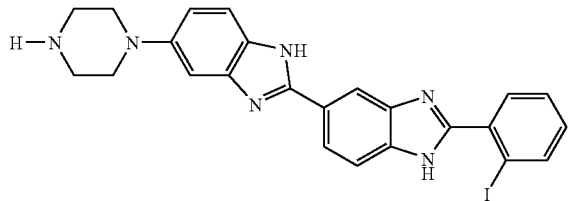

Nitroamine (14) (1.01 g, 3.00 mmol) in 1:4 methanol/ethyl acetate (150 ml) was hydrogenated in the presence of 5% palladium on carbon (0.5 g) at atmospheric pressure for 4 h. The suspension was quickly filtered through celite, and concentrated to give the diamine intermediate as a pale orange solid. Sodium metabisulphite (1.14 g, 6.00 mmol) in 1:1 ethanol/water (50 ml) was added to 2-iodobenzaldehyde (19) (1.39 g, 6.00 mmol) in ethanol (50 ml) and the mixture was shielded from light, and heated over a steam bath for 10 min or until homogeneous. The diamine in ethanol (50 ml) was added to the aldehyde/metabisulphite complex. The mixture was protected from light and heated at reflux, with stirring, under nitrogen for 17 h after which it was cooled to room temperature. The crude product was dissolved in aqueous hydrochloric acid (10%), and re-precipitated with concentrated ammonia solution (~28%) till a loose pale yellow precipitate formed. The suspension was allowed to stand shielded from light at room temperature overnight before filtration. The residue was washed with water, then ether, and dried at the water pump to give 2-iodo-1-{5'-[5''-(4'''-methylpiperazin-1'''-yl)benzimidazol-2''-yl]benzimidazol-2'-yl}benzene (18) as a yellow solid (1.18 g, 76%) m.p. 265-79° dec.

$^1$H nmr (400 MHz, d4-MeOH/d1-TFA): δ 3.45 (m, 4H) pip-CH$_2$; 3.55 (m, 4H) pip-CH$_2$; 7.34 (d, J 2.0 Hz, 1H) H4''; 7.44 (m, 2H) H4, H6''; 7.67 (t, J 7.7 Hz, 1H) H5; 7.75 (m, 2H) H6, H7''; 8.08 (d, J 8.7 Hz, 1H) H7'; 8.16 (d, J 8.1 Hz, 1H) H3; 8.21 (dd, J 8.7, 1.4 Hz, 1H) H6'; 8.59 (brs, 1H) H4'.

Electrospray mass spect.: m/z 521 (M$^+$+1, ~2%); m/2z 261 (100%). Found: M$^+$+1, 521.0928. C$_{24}$H$_{21}$N$_6$I requires M$^+$+1, 521.0950.

2-Iodobenzaldehyde (19)

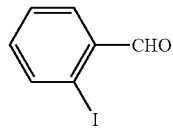

A suspension of pyridinium chlorochromate (8.28 g, 38.4 mmol) and dry celite (5.00 g) in dry dichloromethane was stirred at room temperature for 15 min. 2-Iodobenzyl alcohol (3.03 g, 12.9 mmol) in dry dichloromethane (50 ml) was added. The suspension was shielded from light and stirred at room temperature for 2 h after which it was diluted with ether, and filtered through celite. The cloudy brown filtrate was concentrated to a red-brown gummy solid which was dissolved in dichloromethane and passed through a short silica column, eluting with dichloromethane. The solution was concentrated to give 2-iodobenzaldehyde (19) as a pale yellow oil (2.87 g, 95%).

$^1$H nmr (400 MHz, CDCl$_3$): δ7.29 (Td, J 8.0, 1.8 Hz, 1H) H4, H6; 7.46 (brt, J 8.0 Hz, 1H) H5, 7.88 (dd, J 8.0, 1.8 Hz, 1H) H6; 7.95 (d, J 8.0 Hz, 1H) H3; 10.07 (s, 1H) CHO.

Example 8

2-Iodo-1-{5'-[5'''-(4''''-(1'''',5''''-dioxopent-1-yl)piperazin-1'''-yl)benzimidazol-2''-yl]benzimidazol-2'-yl}benzene (8)

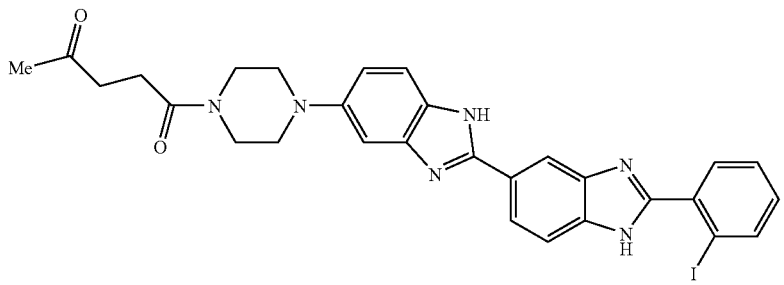

A mixture of compound (18) (0.109 g, 0.209 mmol) and levulinic anhydride (15) (0.124 g, 0.577 mmol) in dry N,N-dimethylformamide (2 ml) was protected from light and stirred at room temperature for 23 h after which it was concentrated to a sticky light brown solid. This was washed with ether and plenty of concentrated ammonia solution (~28%), and then with water and ether again, and pumped down to a yellow solid (0.095 g, contains DCU).

$^1$H nmr (400 MHz, d4-MeOH/d1-TFA): δ 2.65 (m, 2H) H2''''; 2.82 (m, 2H) H3''''; 3.80 (m, 4H) pip-CH$_2$; 7.26 (d, J 2.0 Hz, 1H) H4'''; 7.46 (dd, J 9.2, 2.0 Hz, 1H) H6'; 7.49 (td, J 7.7, 1.6 Hz, 1H) H4; 7.71 (t, J 7.7 Hz, 1H) H5; 7.74 (d, J 9.0 Hz, 1H) H7''; 7.79 (dd, J 7.7, 1.6 Hz, 1H) H6; 8.16 (d, J 8.8 Hz, 1H) H7'; 8.20 (d, J 7.7 Hz, 1H) H3; 8.28 (dd, J 8.8, 1.5 Hz, 1H) H6'; 8.62 (d, J 1.5 Hz, 1H) H4'.

Example 9

Preparation of Radioactively-Labelled Bibenzimidazole DNA Ligand Precursors of Labelled Conjugates

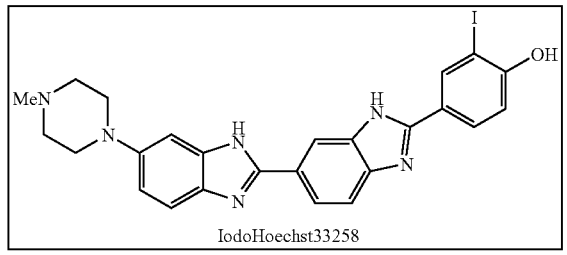

IodoHoechst33258

In general the radioactive iodine is introduced into the DNA ligand by the iododestannylation reaction, and then the ligand is subsequently conjugated to the targeting protein. The conjugation generally involves a two-step process; the first step being activation of the carboxylic acid or carbonyl moiety on the ligand, prior to the actual conjugation reaction.

However in some experiments (for example DNA breakage), the labelled ligand was used in its unconjugated form. For such experiments the DNA ligand did not require a linkage moiety (ie a carbonyl group or carboxylic acid group) and in these cases the radioactive ligand could be conveniently produced by direct iodination of Hoechst 33258, as described in the literature (Martin and Pardee 1985). This produces iodoHoechst 33258, with the indicated molecular structure.

In the iododestannylation reaction for producing a radioactive iodine into the DNA ligand prior to conjugation to the targeting protein, the substrate has a trialkylstannyl moiety, and either carboxylic acid, or a carbonyl moiety. The process is illustrated by the iodination of 3-trimethylstannyl-1-{5'-[5''-(4'''-(1''''-oxy-4''''-carboxybut-1-yl)piperazin-1'''-yl)benzimidazol-2''-yl]benzimidazol-2'-yl}benzene (2) (FIG. 1).

Carrier-free Na$^{125}$I (0.2-3 mCi; 100 mCi/ml; NEN™ Life Science Products) in 2-30 μl 100 mM sodium hydroxide was added to a vial containing 10 μg of the trimethylstannyl precursor in methanol and. An equal volume of 200 mM sodium acetate buffer, pH 5.0 was then added followed by 50 μg/ml lactoperoxidase (2 Units; Sigma Chemical Co.) and ¼ volume of a 0.03% (w/v) aqueous hydrogen peroxide solution. The total volume was 50-100 uL. The sample was vortexed and incubated for 1 hour at room temperature. Two-volumes of 2% tri-n-butylamine in methanol was added to the sample and the meta-$^{125}$I-iodoHoechst analogue was purified using thin layer chromatography (TLC; silica gel 60 aluminium sheets, Merck KGaA, Darmstadt, GER; mobile phase methanol:ethanol:tri-n-butylamine, 200:100:3, R$_f$ meta-$^{125}$I-iodoHoechst 0.21). The radioactive band containing the meta-$^{125}$I-iodoHoechst analogue was excised from the TLC plate and was eluted overnight in 0.2% ammonium acetate in methanol. The sample was lyophilized, re-dissolved in absolute methanol and lyophilized to dryness prior to use. Following optimization, radiochemical yields of 45-55% and overall recovery yields of 30-40% were achieved.

Note: Adjustment of Specific Activity

The product of the above reaction, using carrier-free $^{125}$I-iodide, can be denoted meta-$^{125}$I-iodoHoechst carboxylic acid. Before proceeding with activation of the carboxylic acid and subsequent conjugation to protein, the labelled material was mixed with its non-radioactive counterpart, meta-$^{127}$I-iodoHoechst carboxylic acid to provide preparations at the required specific activity. The target specific activities of meta-$^{127}$I/$^{125}$I-iodoHoechst carboxylic acid were in the range 9-37 Ci/mmole (corresponding approximately to 1 in every 60-250 drug molecules labelled). Similarly, meta-127I-iodoHoechst carbonyl and meta-125I-iodoHoechst carbonyl were mixed to provide preparations with various specific activities. Specific activities of meta-$^{127}$I/$^{125}$I-iodoHoechst carbonyl in the range 7-22 Ci/mmole (approximately 1 every 100-300 drug molecules iodinated), were prepared. Stock solutions of meta-iodoHoechst carboxylic acid and meta-iodoHoechst carbonyl with trace amounts of $^{125}$I-label (<10 mCi/mmole) and without radioactive label were also prepared and were used to optimize the conjugation chemistries and for control studies, respectively.

Examples 10-13

Synthesis of Activated Radioactively-Labelled DNA Ligands for Conjugation to Proteins Example 10

Synthesis of meta-$^{127}$I/$^{125}$I-iodoHoechst-N-hydroxy-succinimidyl-ester

Typically, a 50-100 μL aliquot of 5-10 mM meta-$^{127}$I/$^{125}$I-iodoHoechst carboxylic acid in anhydrous dimethyl sulphoxide (Sigma Chemical Co.) was added to a vial containing a 5-fold molar excess of N-hydroxysuccinimide and N,N'-dicylcohexyl carbodiimide in anhydrous DMSO. The sample was incubated overnight, in the dark at room temperature to yield meta-$^{127}$I/$^{125}$I-iodoHoechst-N-hydroxy-succinimidyl-ester.

This reaction is part of the reaction scheme illustrated in FIG. 1.

Example 11

Synthesis of meta-$^{127}$I/$^{125}$I-iodoHoechst-ethylene amine

An aliquot of meta-$^{127}$I/$^{125}$I-iodoHoechst-N-hydroxy-succinimidyl-ester in 50 mM borate buffer, pH 8.5 containing 3.3% DMSO and 1.7% THF or 5% DMSO was added to a vial containing a 10-20 fold molar excess of ethylene diamine. The mixture was incubated for 2 hours at 5° C. The sample was made up to 20 ml in 13% acetonitrile/dH$_2$O, and excess ethylene diamine was removed by chromatography using a Sep-Pak C$_{18}$ cartridge (Waters Millipore®). The meta-$^{127}$I/$^{125}$I-iodoHoechst-ethylene amine analogue was collected in 2 ml 60% methanol/0.1% TFA and lyophilized to dryness. Reactions were monitored by analytical radio-TLC on silica gel 60 F$_{254}$ aluminium sheets and by HPLC using a linear acetonitrile/0.1% trifluoroacetic acid (TFA) gradient (0.1% aqueous TFA-80% acetonitrile/0.1% TFA; Alltima® C8 Rocket™, 53×7 mm column; flow rate 1 ml/min.). The drugs were monitored for ultraviolet (u.v.) absorbance at 340 nm and for fluorescence (Waters Millipore® 420-AC fluorescence detector), and were found to be >95% pure. The analogues were stored as lyophilized powders in the dark and stock solutions were prepared as required. The chemical yield was estimated to be approximately 60% by measuring the area under the A$_{340\ nm}$ and fluorescence chromatograms obtained by HPLC. Purified samples of meta-$^{127}$I-iodoHoechst-ethylene amine and of low specific activity meta-$^{127}$I/$^{125}$I-iodoHoechst-ethylene amine were analyzed by $^1$H-NMR and by electrospray mass spectrometry. Samples were also analyzed for tin contamination by atomic absorption spectrophotometry.

This reaction is illustrated in the top portion of the reaction scheme shown in FIG. 2.

Example 12

Synthesis of meta-$^{127}$I/$^{125}$I-iodoHoechst-pyridyldithio-proprionate

A 10-fold molar excess of succinimidyl 3-(2-pyridyldithio)proprionate (SPDP), in 50 mM sodium phosphate buffer, pH 7.5 containing 20% (v/v) ethanol was added to the lyophilized meta-$^{127}$I/$^{125}$I-iodoHoechst-ethylene amine. The sample was incubated for 2 hours at 5° C. and made up to 20 mL 13% acetonitrile/dH$_2$O, and unreacted SPDP was removed by chromatography using a Sep-Pak C$_{18}$ cartridge (Waters Millipore®). The meta-$^{127}$I/$^{125}$I-iodoHoechst-pyridyldithio-proprionate analogue was collected in 20 mL 60% methanol/0.1% TFA and lyophilized to dryness. Reactions were monitored by analytical radio-TLC and by HPLC, as described for Example 11. The chemical yield was estimated to be approximately 55% by measuring the area under the A$_{340\ nm}$ and fluorescence chromatograms obtained by HPLC.

Example 13

Synthesis of meta-$^{127}$I/$^{125}$I-iodoHoechst-pyridyldithio-proprionyl hydrazine Typically, a 50-100 μL aliquot of 5-10 mM meta-$^{127}$I/$^{125}$I-iodoHoechst carbonyl, in anhydrous dimethyl sulphoxide (Sigma Chemical Co.) was added to a vial containing a 10-20-fold molar excess of PDP-hydrazide in 100 mM sodium acetate, pH 5.5 containing 20% (v/v) ethanol. The sample was incubated for 2 hours, in the dark at room temperature to yield meta-$^{127}$I/$^{125}$I-iodoHoechst-pyridyldithio-proprionyl hydrazine.

Examples 14-16

Conjugation of Transferrin (or Monoclonal Antibody E4.3) with Meta-$^{127}$I/$^{125}$I-iodoHoechst analogues Example 14

Preparation of the Disulphide Linked Conjugates

For preparation of the disulphide linked conjugates, SPDP or DTT thiolated transferrin or MoAB E4.3 in 100 mM sodium phosphate buffer, pH 7.5 containing 20% (v/v) ethanol was added to the lyophilized meta-$^{127}$I/$^{125}$I-iodoHoechst-pyridyldithio-proprionate to give a 10-20-fold molar excess of bisbenzimidazole to protein. After incubation for 2-3 hours at 5° C. and the conjugates were purified by gel filtration chromatography using a NAP-10 column (Sephadex G-25; Pharmacia Biotech Inc.), that had been equilibrated with 100 mM phosphate buffer, pH 7.5 for meta-$^{127}$I/$^{125}$I-iodoHoechst-MoAB E4.3 conjugates and with 250 mM Tris-HCl, 150 mM NaCl, pH 8.0, 10 μM NHCO$_3$ for meta-$^{127}$I/$^{125}$I-iodoHoechst-transferrin conjugates. Typically, 1 ml of the conjugation reaction mixture, with a protein concentration of 0.5-10 mg/ml, was loaded onto the column and washed with a further 1.2 ml of the corresponding buffer. (Unconjugated bisbenzimidazoles are not eluted from the column under these conditions). The overall process is outlined in FIG. 2 and the syntheses of the principal reactants are described in examples 10, 11 and 12, and the conjugation reaction is described in Example 14

Example 15

Preparation of the Acylhydrazone Conjugates

For preparation of the acylhydrazone conjugates, a 10-20-fold molar excess of meta-$^{127}$I/$^{125}$I-iodoHoechst-pyridyldithio-proprionyl hydrazine was added to SPDP or DTT thiolated transferrin or MoAB E4.3 in 100 mM sodium phosphate buffer, pH 7.5 containing 20% (v/v) ethanol. After incubation for 2-3 hours at 5° C. and the conjugates were purified by gel filtration chromatography, as described for Example 14. The overall process is outlined in FIG. 3 and the syntheses of the principal reactants are described in examples 3 and 13.

Example 16

Preparation of the Amide-Linked Conjugate

For preparation of the amide linked conjugate, a 10-20-fold molar excess of meta-$^{127}$I/$^{125}$I-iodoHoechst-N-hydroxy-succinimidyl-ester was added to transferrin or MoAB E4.3 in 50 mM borate buffer, pH 8.5 containing 5% (v/v) DMSO or in 100 mM phosphate buffer, pH 8.5 containing 5% (v/v) DMSO. After incubation for 2-3 hours at 5° C. and the conjugates were purified by gel filtration chromatography, as described for Example 14. The overall process is outlined in FIG. 4 and the syntheses of the principal reactants are described in examples 2 and 10.

Dependant Procedures for Examples 14-16

Iron Saturation of Transferrin

The meta-$^{127}$I/$^{125}$I-iodoHoechst-transferrin conjugates were saturated with iron as follows. The concentrations of protein and bisbenzimidazole in the conjugates were calculated using absorbance spectrophotometry by approximation from previously determined standard curves for transferrin and MoAB E4.3 at 280 nm and for meta-$^{125}$I-iodoHoechst at 340 nm (Unicam Heλios β UV-Vis spectrophotometer, Thermo-Spectronic, Cambridge, UK). A correction was applied to allow for overlap of bisbenzimidazole absorbance at 280 nm. Although this method may be inexact, because it is not possible to determine precisely if and how the spectral properties of the meta-iodoHoechst moiety are changed following conjugation to the protein it is the most convenient and most frequently used method for estimating drug/protein ratios (Brinkley 1992). A wide range of conjugation numbers (number of iodoHoechst molecules per protein molecule) have been achieved however, the conjugation strategies described in Examples 12-14 were designed to achieve conjugation numbers of 1-3.

Determination of Specific Activities

The specific activities of the conjugates were calculated using the estimates obtained from absorbance spectrophotometry and by measuring aliquots of the conjugates for $^{125}$I-activity in a γ-counter (Perkin Elmer Inc.). A wide range of specific activities have been achieved, however, the conjugation procedures that were optimized to produce high specific activity conjugates (i.e. reactions in which high specific activity meta-$^{127}$I/$^{125}$I-iodoHoechst carboxylic acid and meta-$^{127}$I/$^{125}$I-iodoHoechst carbonyl preparations were used to produce the relevant conjugation precursors), resulted in conjugates with specific activities in the ranges of 12.7-87.5 Ci/mmole protein, 14.5-53.3 Ci/mmole protein and 22.5-98.0 Ci/mmole protein for the disulphide linked, acylhydrazone linked and amide linked meta-$^{125}$I-iodoHoechst-transferrin conjugates, respectively. Specific activities of 24.8 Ci/mmole protein, 15.3 Ci/mmole protein and 21.7 Ci/mmole protein were achieved for the disulphide linked, acylhydrazone linked and amide linked meta-$^{125}$I-iodoHoechst-MoAB E4.3 conjugates, respectively.

Thiolation of Transferrin (or Monoclonal Antibody E4.3)

Typically, thiolation of transferrin and MoAB E4.3 was performed by adding SPDP in absolute ethanol to protein in 100 mM sodium phosphate buffer, pH 7.5 to give a 10-fold molar excess of SPDP to protein (0.5-10 mg/ml). The reaction mixture was incubated for 1 hour at room temperature. Excess unreacted SPDP was removed by gel filtration chromatography using a NAP-5 column that had been equilibrated with 100 mM sodium acetate buffer, pH 4.5. Typically, 800 µl of the reaction mixture was loaded to the column and the protein was eluted in 1 ml of the corresponding buffer. The dithiopyridyl protecting groups were then removed by reduction of the disulphide bond by reaction with a 10-fold molar excess of dithiothreitol (DTT), for 30 minutes at room temperature. Thiolated proteins were purified immediately by gel filtration chromatography using a NAP-5 or NAP-10 column that had been equilibrated with 100 mM sodium phosphate buffer, pH 7.5.

Reactive thiol groups were also introduced into the proteins by reduction with DTT. Typically, DTT was added to protein in 100 mM sodium acetate buffer, pH 4.5 to give a 10-50 fold molar excess of DTT to protein. Thiolated proteins were purified by gel filtration chromatography as described above.

Example 17

Confirmation of Biological Activity of Transferrin-DNA Ligand Conjugates—Comparison of Labelled Conjugates with $^{125}$I-transferrin An important requirement of immunoconjugates is that the protein moieties of the conjugates retain the binding affinity and specificity of the unmodified proteins for their respective cell-surface receptors or antigens. The binding characteristics of the meta-$^{127}$I/$^{125}$I-iodoHoechst-transferrin conjugates were compared to the binding characteristics of $^{125}$I-transferrin to cell-surface transferrin receptors using receptor binding radioassays. For investigation of the binding of $^{125}$I-transferrin and meta-$^{127}$I/$^{125}$I-iodoHoechst-transferrin conjugates, K562 cells were washed three times with 1% BSA/PBS. A 100 µl aliquot of 1% BSA/PBS or 100 µl of 1% BSA/PBS containing unlabelled human diferric transferrin (100-fold molar excess to $^{125}$I-transferrin and meta-$^{127}$I/$^{125}$I-iodoHoechst-transferrin conjugates, for estimation of non-specific binding) was added to cells (5×10$^5$) in 200 µl 1% BSA/PBS. A 200 µl aliquot of $^{125}$I-transferrin or meta-$^{127}$I/$^{125}$I-iodoHoechst-transferrin conjugates was added to appropriate samples. The samples were incubated for 90 minutes at 4° C. and the cell-surface bound and free $^{125}$I-labelled ligands were separated by centrifugation at 10000×g for 3 minutes through a 50% dibutyl pthalate/50% dioctyl phthalate oil-layer (density 1.012 g/l) and the $^{125}$I-activity in the cell pellets was determined in a β-counter.

Figure 5:
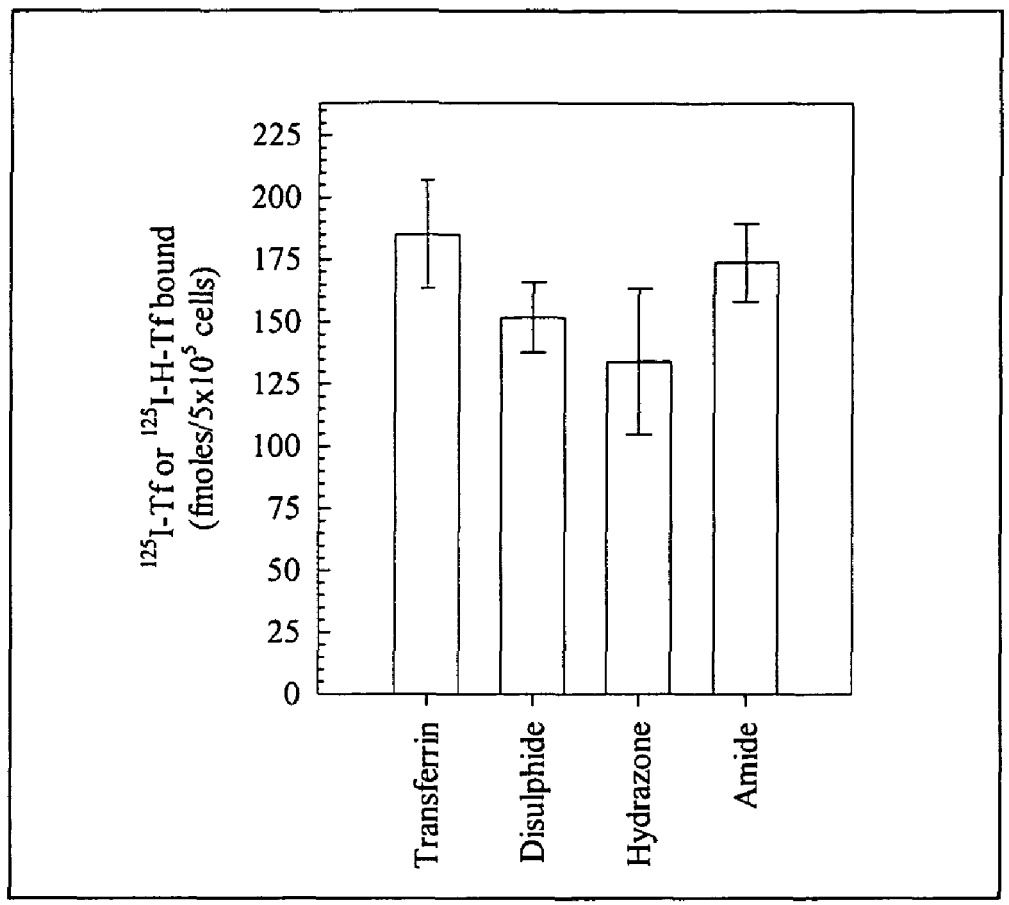
FIG. 5 shows a bar graph of binding (fmoles/5×10$^5$ cells) to cell surface receptors on K562 cells of $^{125}$I-transferrin and meta-$^{127}$I/$^{125}$I-iodoHoechst-transferrin conjugates linked by disulphide, hydrazone or amide linkages. Cells (5×10$^5$) were incubated with 10.3 nM $^{125}$I-transferrin or meta-$^{127}$I/$^{125}$I-iodoHoechst-transferrin conjugates.

The number of binding sites for $^{125}$I-transferrin on K562 cells were calculated to be (1.9±0.4)×105. The results (FIG. 5) indicated that the amide, the disulphide and the acylhydrazone conjugates retained approximately 98%, 88% and 93% of the binding of unconjugated $^{125}$I-transferrin to specific receptors, respectively, indicating that linking 1-3 meta-$^{127}$I/$^{125}$I-iodoHoechst moieties to transferrin does not significantly affect the binding properties of the protein to cell-surface transferrin receptors on K562 cells.

Example 18

Figure 6:
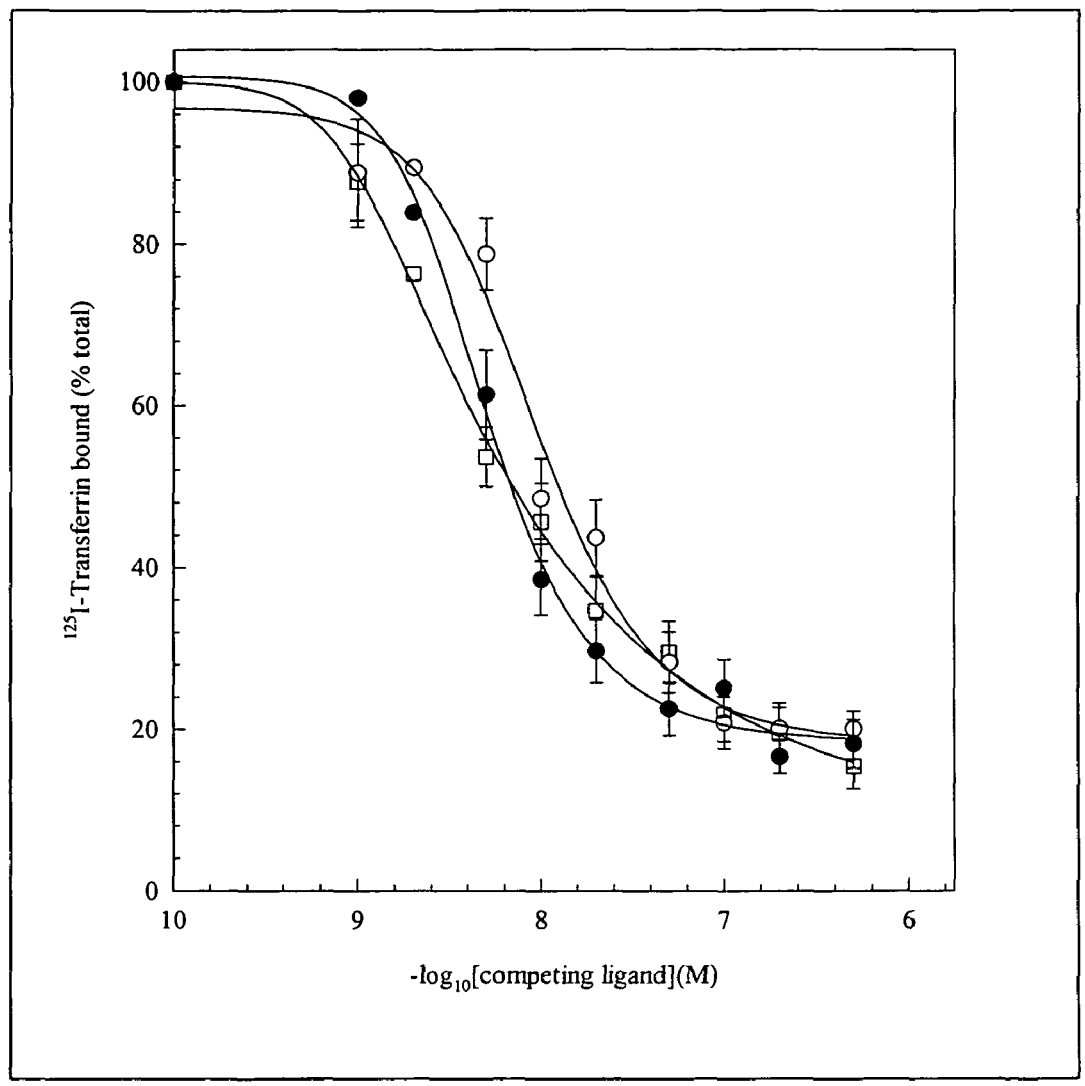
FIG. 6 shows Competition binding curves between meta-iodoHoechst-transferrin conjugates and $^{125}$I-transferrin for specific binding sites in K562 cells. Cells (5×10$^5$) were incubated with 3 nM $^{125}$I-transferrin and a series (1-500 nM) of concentrations of competing ligand (amide [closed circles], disulphide [open circles] or acylhydrazone [open squares] conjugates).

Confirmation of Biological Activity of Transferrin-DNA Ligand Conjugates—Competition by Unlabelled Conjugates for $^{125}$I-Transferrin Binding Sites on K562 Cells The characteristics of binding of the meta-$^{127}$I/$^{125}$I-iodoHoechst-transferrin conjugates to cell-surface transferrin receptors on K562 cells were also analysed by competition binding experiments (competition by unlabelled conjugates for $^{125}$I-transferrin binding sites). K562 cells were washed three times with ice-cold 1% (w/v) bovine serum albumin (BSA) in serum-free RPMI 1640 medium containing 20 mM 4-(-2-hydroxyethyl)-1-piperazineethanesulfonic acid (HEPES), pH 7.4 and 80 I.U./ml gentamicin (RPMI 1640/BSA). Cell pellets (5×10$^5$ per sample) were suspended in 50 μl of assay buffer (200 mM Tris-HCl, 150 mM NaCl, pH 7.4, for estimation of total binding) containing a series of concentrations (0-500 nM) of the meta-$^{127}$I-iodoHoechst-transferrin conjugates (competing ligand; conjugation number 1.2, 1.1 and 2.9 for the disulphide, acylhydrazone and amide linked conjugates, respectively) was added to the K562 cells. This was followed by addition of a 50 μl aliquot of $^{125}$I-diferric transferrin (3 nM final concentration; specific activity 30.5 Ci/mmole). The samples were incubated at 0° C. for 90 minutes and the cell-surface bound and free $^{125}$I-diferric transferrin was separated by centrifugation at 10000×g for 3 minutes through a mineral oil-layer as described above. Following excision of the tips of the tubes or removal of the supernatant and most of the mineral oil, the $^{125}$I-activity in the cell-pellets was counted in a β-counter. To correct for non-specific binding, assays were performed in parallel in the presence of a 50-fold molar excess of unlabelled diferric transferrin. Specific $^{125}$I-diferric transferrin binding was represented by the difference of the total and non-specific binding. Control assays, in which the unconjugated meta-$^{127}$I-iodoHoechst analogue, at an equivalent concentration to the concentration of bisbenzimidazole moiety in the meta-$^{127}$I-iodoHoechst-transferrin conjugates was used as the competing ligand, were also performed. Assays were conducted in triplicate and generally differed from each other by less than ±10%. The results are shown in FIG. 6.

The data derived from the competition binding studies were analyzed using a one-site competition model. The equilibrium inhibition constants were estimated to be 4.8±1.3, 3.9±0.9 and 3.1±1.1 nM for the disulphide, the acylhydrazone and the amide linked meta-$^{127}$I/$^{125}$I-iodoHoechst-transferrin conjugates, respectively. These results, as reflected in FIG. 6, indicated that the conjugates compete for $^{125}$I-diferric transferrin binding sites on K562 cells and that the disulphide, acylhydrazone and amide linked conjugates have a similar affinity for the cell-surface transferrin receptors on K562 cells.

Example 19

Transferrin Receptor-Mediated Delivery of an $^{125}$I-Labelled DNA Ligand to K562 Cells—Inhibition by Excess Unlabelled Transferrin Human erythroleukemic, K562 cells were washed three times in RPMI 1640/BSA, resuspended (5×10$^5$ per ml) and incubated with $^{125}$I-transferrin (specific activity, 14.6 Ci/mmole) or with one of the three meta-$^{127}$I/$^{125}$I-iodoHoechst-transferrin conjugates (specific activities 8.5, 6.9 and 2.7 Ci/mmole protein and conjugation number of 2.8, 2.9 and 3.1 for the disulphide, the acylhydrazone and the amide linked conjugates, respectively) at a final protein concentration of 200 nM, at 37° C. At the required time intervals (0-20 hours), the cell-associated and extracellular $^{125}$I-ligands were separated by centrifugation at 400×g for 3 minutes and the cell-associated $^{125}$I-activity and the $^{125}$I-activity in the supernatants were counted in a β-counter (80% counting efficiency; Perkin Elmer Inc.). To elucidate whether the meta-$^{127}$I/$^{125}$I-iodoHoechst-transferrin conjugates were internalized specifically via transferrin receptor mediated endocytosis, assays were performed in parallel in the presence of 100-fold molar excess of unlabelled diferric transferrin.

Figure 7:
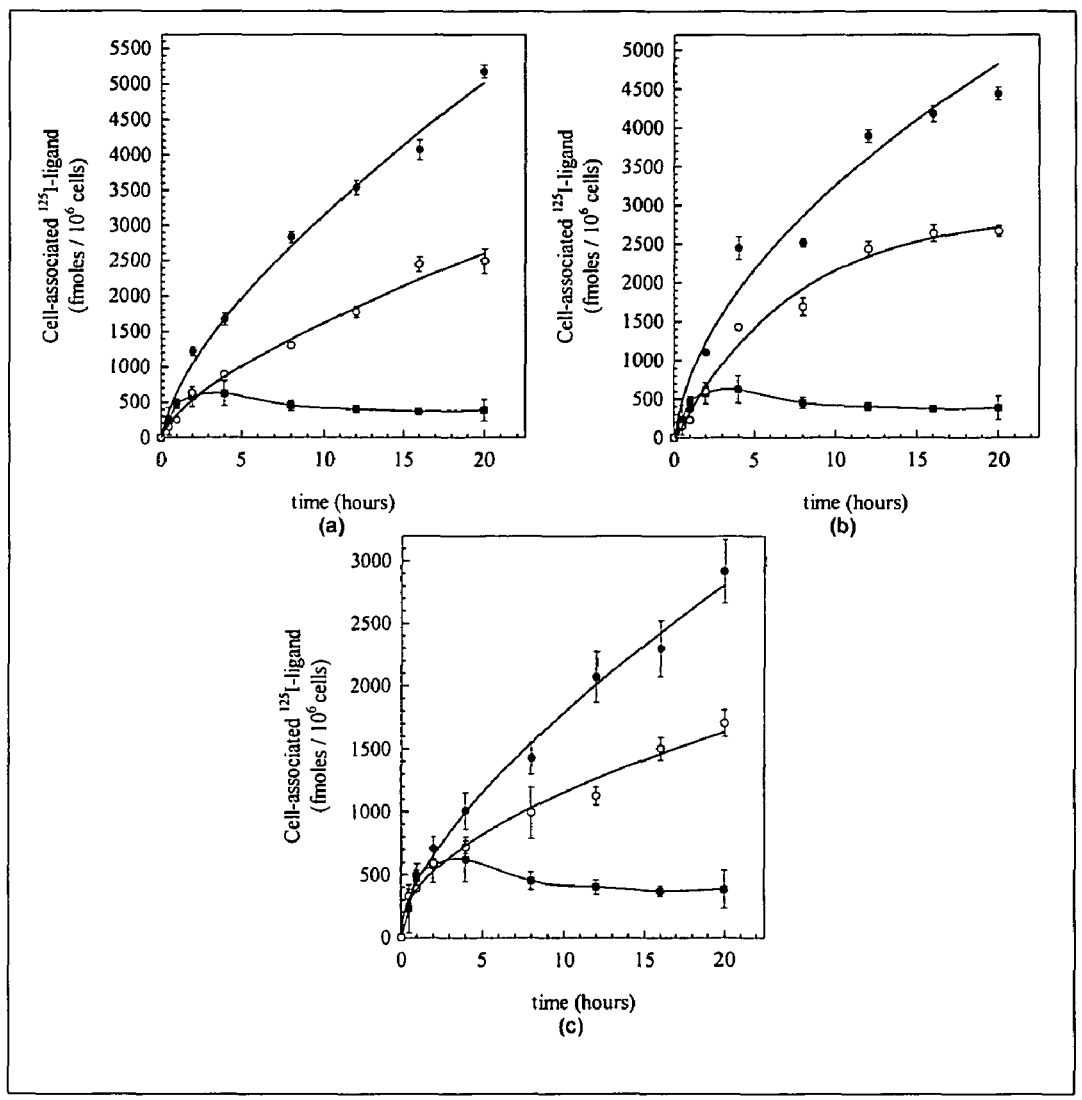
FIG. 7 shows accumulation (fmoles/10$^6$ cells) of $^{125}$I-ligand in K562 cells following incubation with $^{125}$I-transferrin and meta-$^{127}$I/$^{125}$I-iodoHoechst-transferrin conjugates. Cells (5×10$^5$/ml) were incubated with $^{125}$I-transferrin ((a), (b) and (c); closed squares) or with the disulphide (a; closed circles), acylhydrazone (b; closed circles) or amide (c; closed circles) linked conjugates (protein concentration, 200 nM), at 37° C. At the indicated times the cell-associated and extracellular ligands were separated by centrifugation and the cellular $^{125}$I-activity was counted in a γ-counter. In parallel assays, the cells were incubated with the conjugates in the presence of 100-fold molar excess unlabelled transferrin (open circles; (a) disulphide, (b) acylhydrazone, (c) amide conjugates).

The results from the cellular $^{125}$I-activity studies indicated a time-dependent increase in the cell-associated $^{125}$I-activity at a rate of approximately 5.2 fmoles $^{125}$I-ligand/cell/minute for approximately the first 2 hours of incubation with $^{125}$I-diferric transferrin (FIG. 7). The rate of increase of the cell-associated $^{125}$I-activity then decreased to approximately 0.8 fmoles $^{125}$I-ligand/cell/minute and a plateau was almost reached indicating a steady-state between cell-surface binding and internalization and release until incubation with $^{125}$I-diferric transferrin for approximately 4-5 hours. A small decrease, at a rate of approximately 0.2 fmoles $^{125}$I-ligand/cell/minute in cell-associated $^{125}$I-activity was then observed for studies with $^{125}$I-diferric transferrin for the incubation period between 5-20 hours (FIG. 6-7). In contrast, a time-dependent increase in the cell-associated $^{125}$I-activity was observed throughout the incubation period with the meta-$^{127}$I/$^{125}$I-iodoHoechst-transferrin conjugates. The rate of increase for the first 4 hours of incubation was calculated to be approximately 7.2, 10.4 and 3.6 fmoles $^{125}$I-ligand/cell/minute for incubations with the disulphide, the acylhydrazone and the amide linked meta-$^{127}$I/$^{125}$I-iodoHoechst-transferrin conjugates, respectively. The rate of increase of the cell-associated $^{125}$I-activity then decreased to approximately 6.1, 5.7 and 2.6 fmoles $^{125}$I-ligand/cell/minute for the disulphide, acylhydrazone and amide linked meta-$^{127}$I/$^{125}$I-iodoHoechst-transferrin conjugates, respectively, for the incubation period between 4-20 hours.

The results from the cellular $^{125}$I-activity studies also indicated that the accumulation of the cell-associated $^{125}$I-activity following incubation with the meta-$^{127}$I/$^{125}$I-iodoHoechst-transferrin conjugates could be inhibited (approximately 2-fold inhibition) by incubation in the presence of a 100-fold molar excess of unlabelled diferric transferrin. These results provide evidence that the accumulation in the cell-associated $^{125}$I-activity was largely mediated by transferrin receptor endocytosis.

Example 20

Transferrin Receptor-Mediated Delivery of an $^{125}$I-Labelled DNA Ligand to K562 Cells—Metabolic Inhibition of Endocytosis In parallel with the experiment described in Example 19, cultures of K562 cells with one of the three labeled DNA ligand—transferring conjugates were incubated at 0° C., a condition that inhibits receptor-mediated endocytosis. Other assays were performed in parallel at 37° C. in the presence of the metabolic inhibitors d-deoxy-D-glucose (50 mM) and sodium azide (0.1% (w/v)), which are known to inhibit transferrin receptor mediated endocytosis (Ciechanover, et al. 1983).

Figure 8:
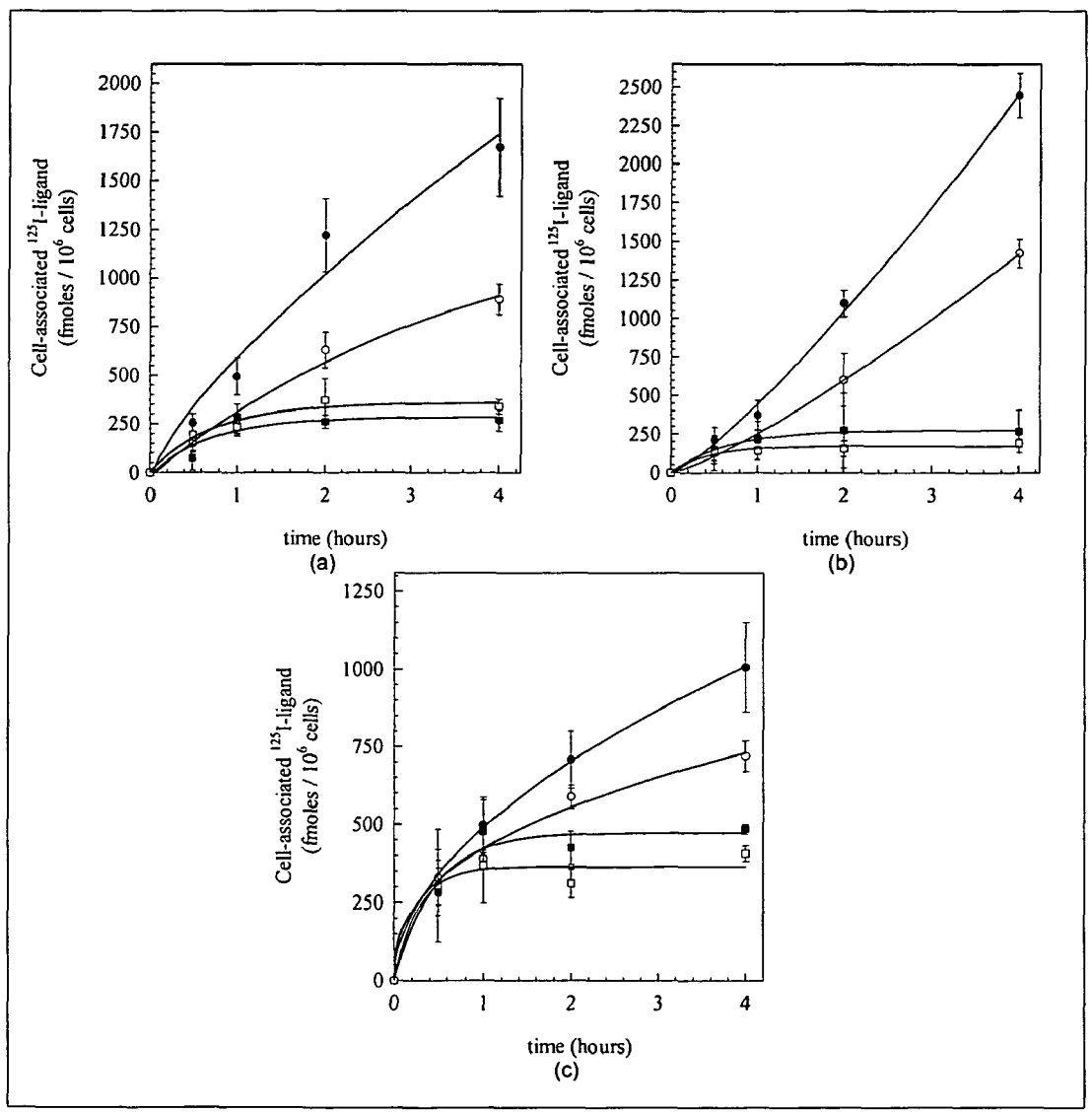
FIG. 8 shows inhibition of accumulation (fmoles/10$^6$ cells) of cellular $^{125}$I-ligand following exposure of K562 cells to meta-$^{127}$I/$^{125}$I-iodoHoechst-transferrin conjugates by incubation at 0° C., in the presence of metabolic inhibitors or in the presence of excess unlabelled transferrin. Cells (5×10$^5$/ml) were incubated with the disulphide (a), acylhydrazone (b) or amide (c) linked conjugates (protein concentration, 200 nM), at 37° C. (closed circles) in the presence of the metabolic inhibitors d-deoxy-D-glucose and sodium azide (at 37° C.; closed squares), in the presence of 100-fold molar excess unlabelled transferrin (at 37° C.; open circles) or at 0° C. (open squares).

The results (FIG. 8) indicated that the cell-associated $^{125}$I-activity following incubation with the meta-$^{127}$I/$^{125}$I-iodoHoechst-transferrin conjugates could be almost completely inhibited by incubation in the presence of the metabolic inhibitors d-deoxy-D-glucose and sodium azide and when incubations were performed at 0° C. These results provide further evidence that the accumulation in the cell-associated $^{125}$I-activity was largely mediated by transferrin receptor endocytosis.

Example 21

Transferrin Receptor-Mediated Delivery of an $^{125}$I-Labelled DNA Ligand to the Nuclei of K562 Cells For the nuclear $^{125}$I-activity accumulation studies, assays were performed in parallel in which the washed cells following incubation with $^{125}$I-transferrin or with the meta-$^{127}$I/$^{125}$I-iodoHoechst-transferrin conjugates, were suspended in ice-cold 10 mM Tris-HCl, pH 7.4, 3 mM CaCl$_2$, 2 mM magnesium acetate (hypotonic buffer). After incubation for 5 minutes at 0° C., an equal volume of hypotonic buffer containing 1% (v/v) Triton X-100 was added while vortexing, and the cells were sheared by passage through a 22-gauge needle. The nuclei were separated from the cytosol by centrifugation at 1000×g for 10 minutes and the nuclear preparations were washed in hypotonic buffer and pipetted to avoid clumping. The concentration of nuclei isolated from each sample was determined by counting with a hemocytometer and the nuclear- and cytoplasm-associated $^{125}$I-activity was determined by β-counting. In parallel assays, the nuclei were washed with 10 mM Tris-HCl, 140 mM NaCl, pH 8.3 (isotonic buffer) by centrifugation at 1000×g for 10 minutes and the nuclear associated $^{125}$I-activity and the $^{125}$I-activity in the supernatants was determined by β-counting.

Figure 9:
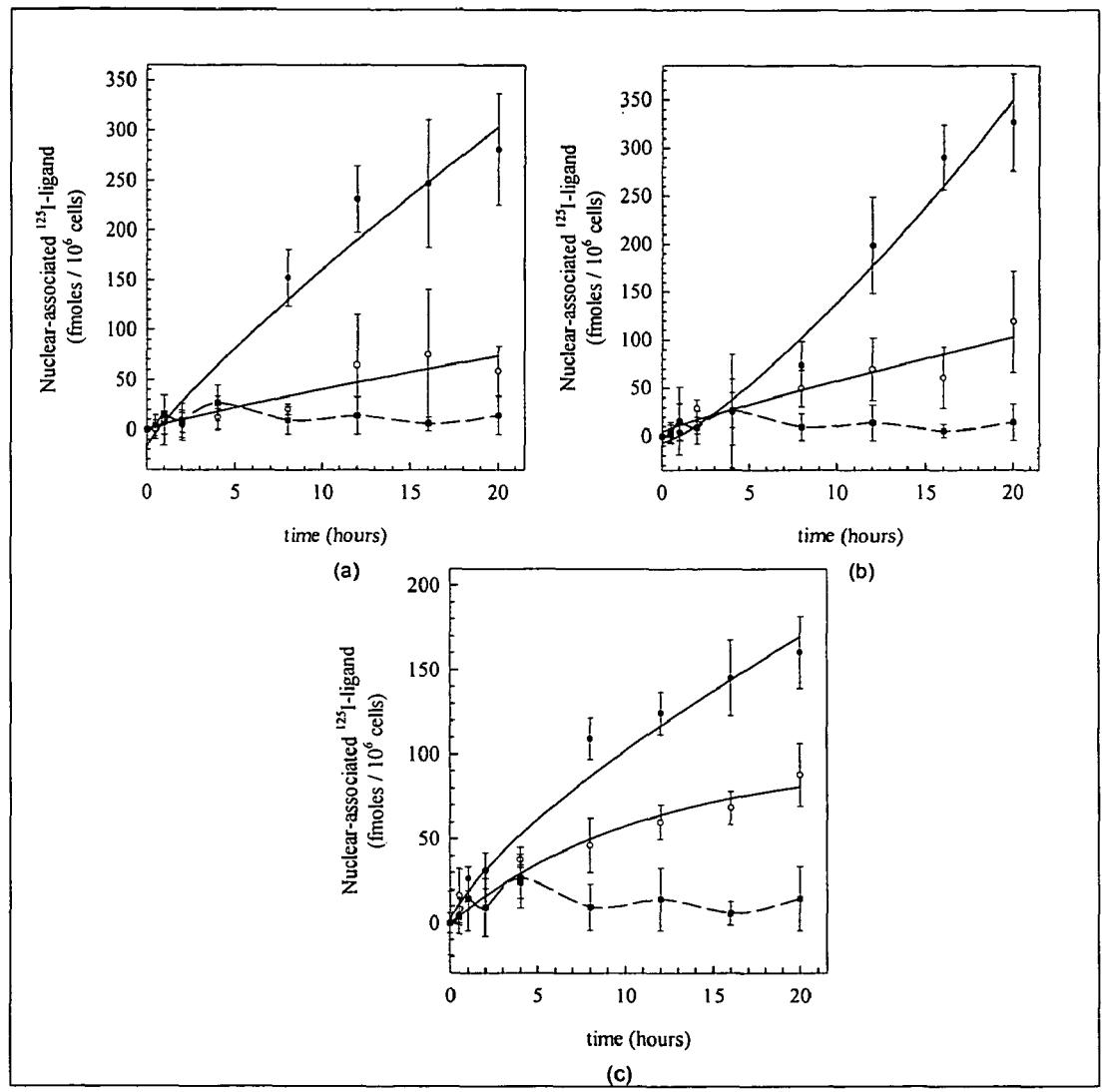
FIG. 9 shows accumulation (fmoles/10$^6$ cells) of $^{125}$I-ligand in K562 nuclei following incubation with meta-$^{127}$I/$^{125}$I-iodoHoechst-transferrin conjugates. Cells (5×10$^5$/ml) were incubated with $^{125}$I-transferrin ((a), (b) and (c); closed squares) or with the disulphide (a; closed circles), acylhydrazone (b; closed circles) or amide (c; closed circles) linked conjugates (protein concentration, 200 nM), at 37° C. At the indicated times the cell-associated and extracellular ligands were separated by centrifugation, the nuclei were isolated using a hypotonic buffer and neutral detergent (Triton X-100) and the nuclear $^{125}$I-activity was counted in a γ-counter. In parallel assays, the cells were incubated with the conjugates in the presence of 100-fold molar excess unlabelled transferrin (open circles; (a) disulphide, (b) acylhydrazone, (c) amide conjugates).

The results from the nuclear $^{125}$I-activity studies also indicated a time-dependent increase in the nuclear-associated $^{125}$I-activity following incubations with the meta-$^{127}$I/$^{125}$I-iodoHoechst-transferrin conjugates (FIG. 9). The rate of increase of the nuclear-associated $^{125}$I-activity was calculated to be 0.21, 0.38 and 0.13 fmole $^{125}$I-ligand/cell/minute for the disulphide, the acylhydrazone and the amide linked meta-$^{127}$I/$^{125}$I-iodoHoechst-transferrin conjugates, respectively. Furthermore, the results indicated that the cell-associated $^{125}$I-activity following incubation with the meta-$^{127}$I/$^{125}$I-iodoHoechst-transferrin conjugates could be inhibited (approximately 2-4-fold inhibition) in the presence of a 100-fold molar excess of unlabelled diferric transferrin, providing evidence that the accumulation in the nuclear-associated $^{125}$I-activity was predominantly mediated by transferrin receptor endocytosis. As expected by considering the transferrin receptor-mediated endocytosis system, accumulation of $^{125}$I-activity in the nuclei was not observed following incubation with $^{125}$I-diferric transferrin.

Example 22

Transferrin Receptor-Mediated Delivery of Ortho-iodoHoechst to the Nuclei of K562 Cells The delivery of ortho-iodoHoechst to K562 nuclei following incubation of cells with the acylhydrazone linked transferrin-ortho-iodoHoechst conjugate was examined by quantitative fluorescence microscopy, after photolytic deiodination. K562 cells in RPMI 1640 containing 3% FBS, 20 mM HEPES and 80 I.U./ml gentamicin were incubated with the acylhydrazone linked conjugate (200 mM, conjugation number 1.5) for 24 hours at 37° C. Following incubation the cells were irradiated with 200 Jm$^{-2}$ UV$_A$ to generate in situ the dehalogenated ligand, which is much more fluorescent than the iodinated ligand. The cells were then washed by centrifugation and the cell-pellet was resuspended in 50 μl PBS without Ca$^{2+}$/Mg$^{2+}$. Aliquots (20 μl) were placed onto microscope slides and were allowed to air-dry. Prior to microscopy a drop of 30% PBS and 100 μM dithiothreitol in Tissuetek was added to the cells. K562 cells were observed using a fluorescence microscope (Zeiss) and a standard Hoechst filter set. Analysis of nuclear fluorescence was performed using a Bio-Rad Molecular Imager® Fx (Bio-Rad Laboratories, Hercules, Calif., USA) and Quantity One™ 4.1.1 software.

Figure 10:
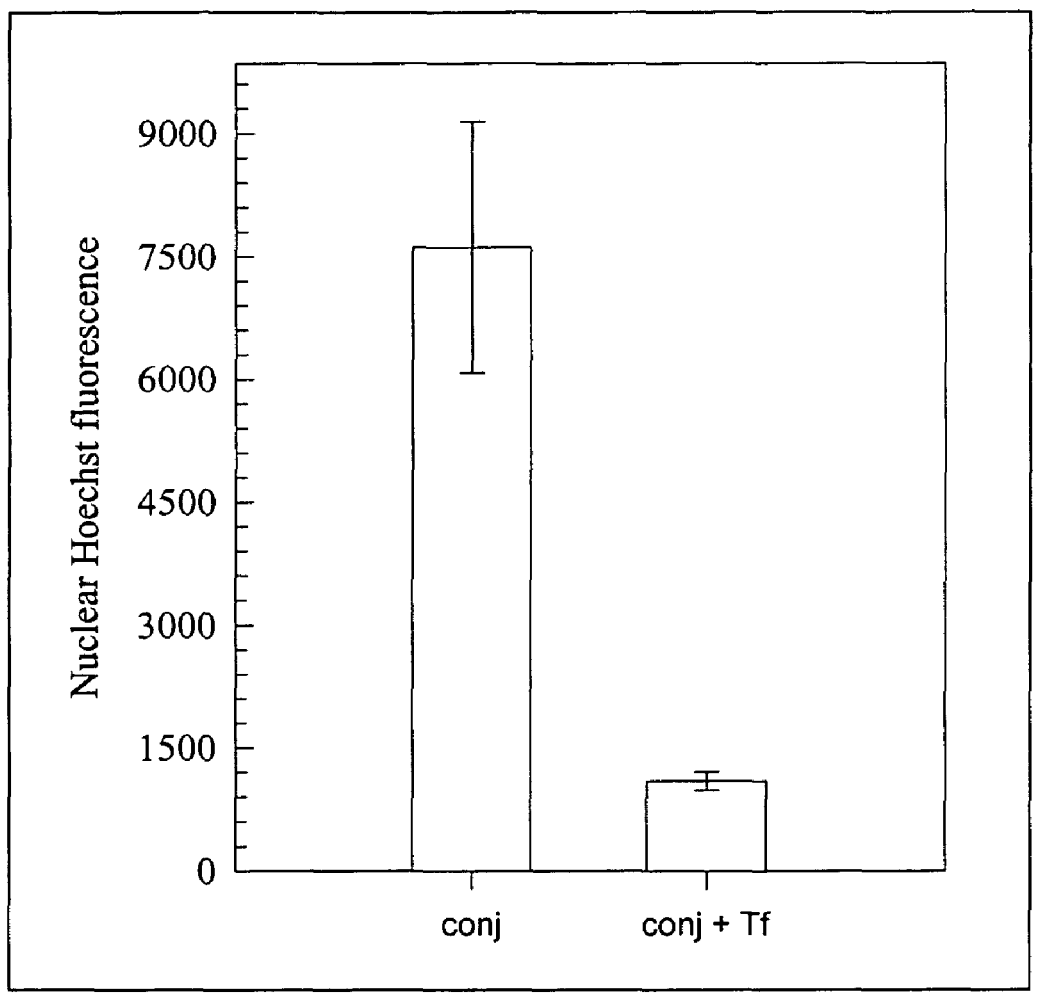
FIG. 10 shows a bar graph of nuclear fluorescence following incubation for 24 hrs at 37° C. with the hydrazone linked transferrin-iodoHoechst conjugate (conj; conjugation no. 1.5) and subsequent dehalogenation by UV-irradiation, and inhibition of increase in nuclear fluorescence by incubation in the presence of 100-fold molar excess transferrin (conj+Tf).

The results (FIG. 10) indicated significant fluorescence in K562 cell nuclei. Importantly, the nuclear fluorescence was largely inhibited by incubation in the presence of 100-fold molar excess unmodified transferrin, consistent with the conclusion that delivery of the sensitising ligand to nuclear DNA is mediated by binding of the ligand-transferrin complex to transferrin receptors. Calculations based on fluorescence intensity suggested that the efficiency of receptor-mediated delivery of ligand to the nucleus was similar to that indicated in example 21.

Example 23

Transferrin Receptor-Mediated Killing of K562 Cells by an $^{125}$I-DNA Ligand

The cytotoxicity $^{125}$I-diferric transferrin and of the meta-$^{127}$I/$^{125}$I in K562 cells was examined using clonogenic survival assays.

K562 cells were washed three times in serum-free RPMI 1640 containing 20 mM HEPES and 80 I.U./ml gentamicin. In the representative experiment, cells (5×10$^5$ per ml) were incubated with a series of radioactive doses of $^{125}$I-diferric transferrin (highest dose 3.8 μCi/ml; specific activity 18.9 Ci/mmole, 200 nM protein concentration) or with a series of radioactive doses of the required meta-$^{127}$I/$^{125}$I-iodoHoechst-transferrin conjugate (highest doses 17.5, 10.1 and 18.3 μCi/ml, specific activities 87.5, 53.3 and 98 Ci/mmole protein for the disulphide, acylhydrazone and amide linked meta-$^{127}$I/$^{125}$I-iodoHoechst-transferrin conjugates, respectively, protein concentration 200 nM, conjugation number 2.8, 2.9 and 3.1 for the disulphide, acylhydrazone and amide linked conjugates, respectively) for 20 hours at 37° C. To ensure that cytotoxicity was mediated by decay of $^{125}$I, control assays were performed in parallel with unlabelled meta-$^{127}$I-iodoHoechst-transferrin conjugates. Furthermore, to determine whether the $^{125}$I-induced cytotoxicity was mediated by transferrin receptor-mediated endocytosis, control assays were performed in parallel in the presence of a 50-fold molar excess of unlabelled diferric transferrin. Following incubation, the cell-pellets were isolated by centrifugation at 400×g for 3 minutes and suspended in the α-modification of Eagle's medium containing 20% (v/v) fetal bovine serum, 20 mM HEPES, 2 mM L-glutamine and 80 I.U./ml gentamicin. An appropriate cell number from each of the samples was then cloned in semi-solid (0.33% (w/v)) noble agar in 6-well microtiter plates.

Figure 11:
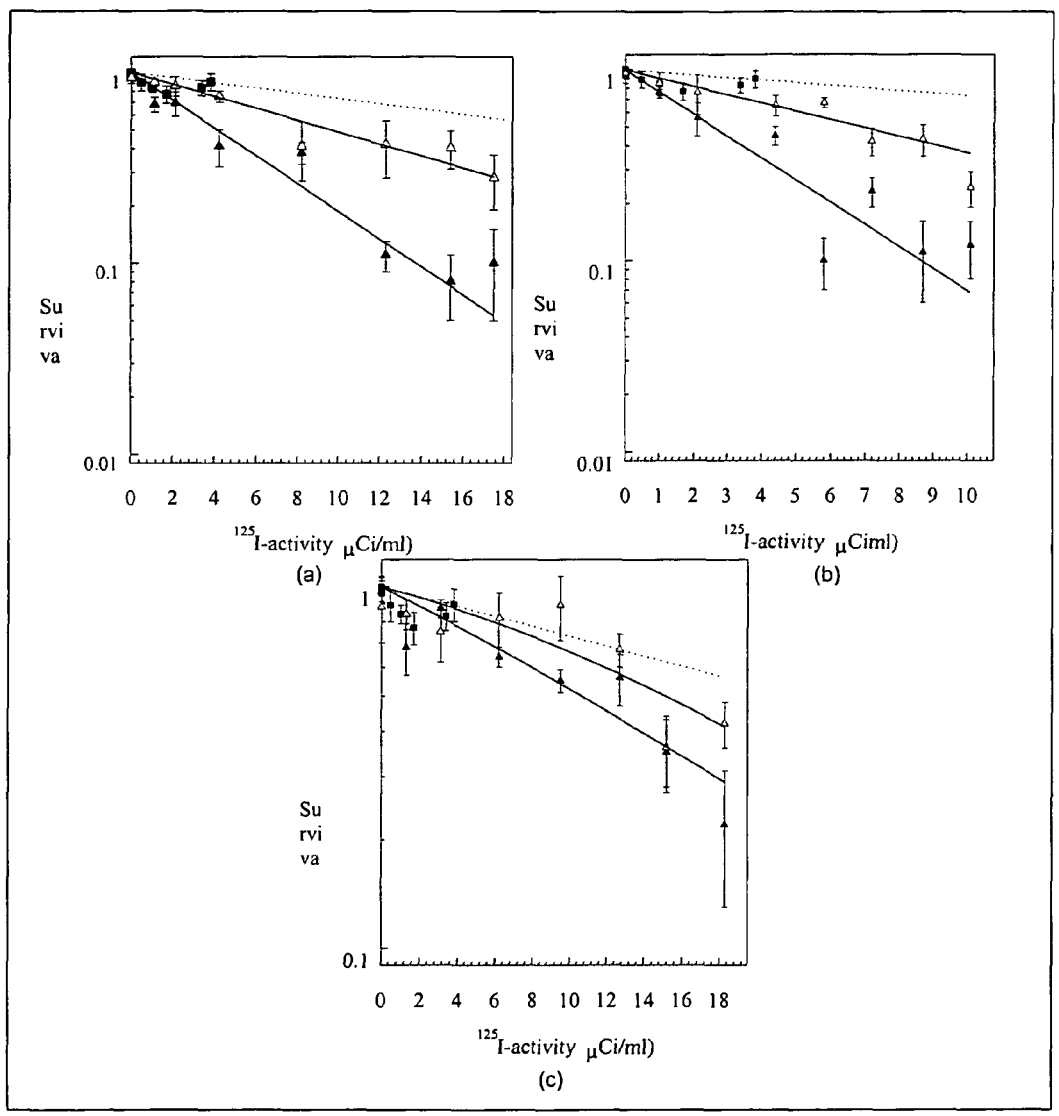
FIG. 11 shows clonogenic survival of K562 cells following incubation with $^{125}$I-transferrin and meta-$^{127}$I/$^{125}$I-iodoHoechst-transferrin conjugates. Cells (5×10$^5$/ml) were incubated with a series of radioactive doses of $^{125}$I-transferrin ((a), (b) and (c); closed squares) or with a series of radioactive doses of the disulphide ((a); closed triangles), acylhydrazone ((b); closed triangles) and amide ((c); closed triangles) linked conjugates for 20 hours at 37° C. In parallel assays, the cells were incubated with the conjugates in the presence of a 50-fold molar excess of unlabelled transferrin (open triangles; (a) disulphide, (b) acylhydrazone, (c) amide conjugates).

The results (FIG. 11) indicated that $^{125}$I-diferric transferrin and the meta-$^{127}$I/$^{125}$I-iodoHoechst-transferrin induced cytotoxicity in K562 cells. The doses required to produce on average one lethal event per cell ($D_{37}$) were calculated to be 31.8 μCi/ml for $^{125}$I-diferric transferrin and 6.0, 3.8 and 8.9 μCi/ml for the disulphide, acylhydrazone and amide linked meta-$^{127}$I/$^{125}$I-iodoHoechst-transferrin conjugates, respectively. Importantly, the results indicated that the cytotoxicity induced by the meta-$^{127}$I/$^{125}$I-iodoHoechst-transferrin conjugated was inhibited approximately 2-3-fold by incubations in the presence of a 50-fold molar excess of unlabelled diferric transferrin. This result provides evidence that the cytotoxicity affected by the meta-$^{127}$I/$^{125}$I-iodoHoechst conjugates was mediated predominantly by transferrin receptor-mediated endocytosis.

Note: Simulation of In Vitro Cytotoxicity

Using an average value of 1.1 Gy for the nuclear absorbed dose required for $D_{37}$, the nuclear absorbed dose accumulated with each transferrin cycle (using appropriate S- and RBE-values) and with the use of the multi-target model for calculating survival, simulated survival curves for various specific activities $^{125}$I-transferrin and of the meta-$^{127}$I/$^{125}$I-iodoHoechst-transferrin conjugates were derived (Karagiannis, 2001). The simulations indicated that approximately 19-21 and 51-54 transferrin cycles would be required for $D_{37}$ and for 6-logs of cell kill (virtually complete cell-kill), respectively, following incubation with $^{125}$I-transferrin. By contrast, approximately 9-11, 7-9 and 15-17 transferrin cycles would be required for $D_{37}$ and 22-24, 19-21 and 30-32 transferrin cycles would be required for 6-logs cell kill following incubation with the disulphide, the acylhydrazone and the amide linked meta-$^{125}$I-iodoHoechst-transferrin conjugates, respectively, for situations where each transferrin molecule would contain three $^{125}$I-atoms (Karagiannis, 2001).

The results from the simulations are in accord with the intracellular accumulation, nuclear localization and cytotoxicity data. Together these data indicate that the acid-labile acylhydrazone linked meta-$^{127}$I/$^{125}$I-iodoHoechst conjugate is more efficient than the disulphide linked conjugate which in turn is more efficient than the amide linked conjugate with respect to receptor-specific intracellular accumulation and nuclear localization of $^{125}$I-ligand and receptor-specific cytotoxicity. Similarly, the experimentally derived and the simulated data support the expectation that more efficient cytotoxicity would be achieved by localizing a proportion of the Auger electron emitting isotope in the nucleus rather than localizing the $^{125}$I exclusively in intra-cytoplasmic vesicles or on the cell-surface.

Example 24

Transferrin Receptor-Mediated Delivery of Ortho-iodoHoechst to K562 Cells and Killing by $UV_A$—Irradiation The cytotoxicity of the transferrin-ortho-iodoHoechst conjugates in K562 cells was examined using clonogenic survival assays. K562 cells in RPMI 1640 containing 3% FBS, 20 mM HEPES and 80 I.U./ml gentamicin were incubated with transferrin-ortho-iodoHoechst conjugates for 24 hours at 37° C. Following incubation the cells were irradiated with various $UV_A$ doses. The cells were then washed by centrifugation and cell-pellets were suspended in the α-modification of Eagle's medium containing 20% (v/v) fetal bovine serum, 20 mM HEPES, 2 mM L-glutamine and 80 I.U./ml gentamicin. An appropriate cell number from each of the samples was then cloned in semi-solid (0.33% (w/v)) noble agar in 6-well microtiter plates.

Figure 12:
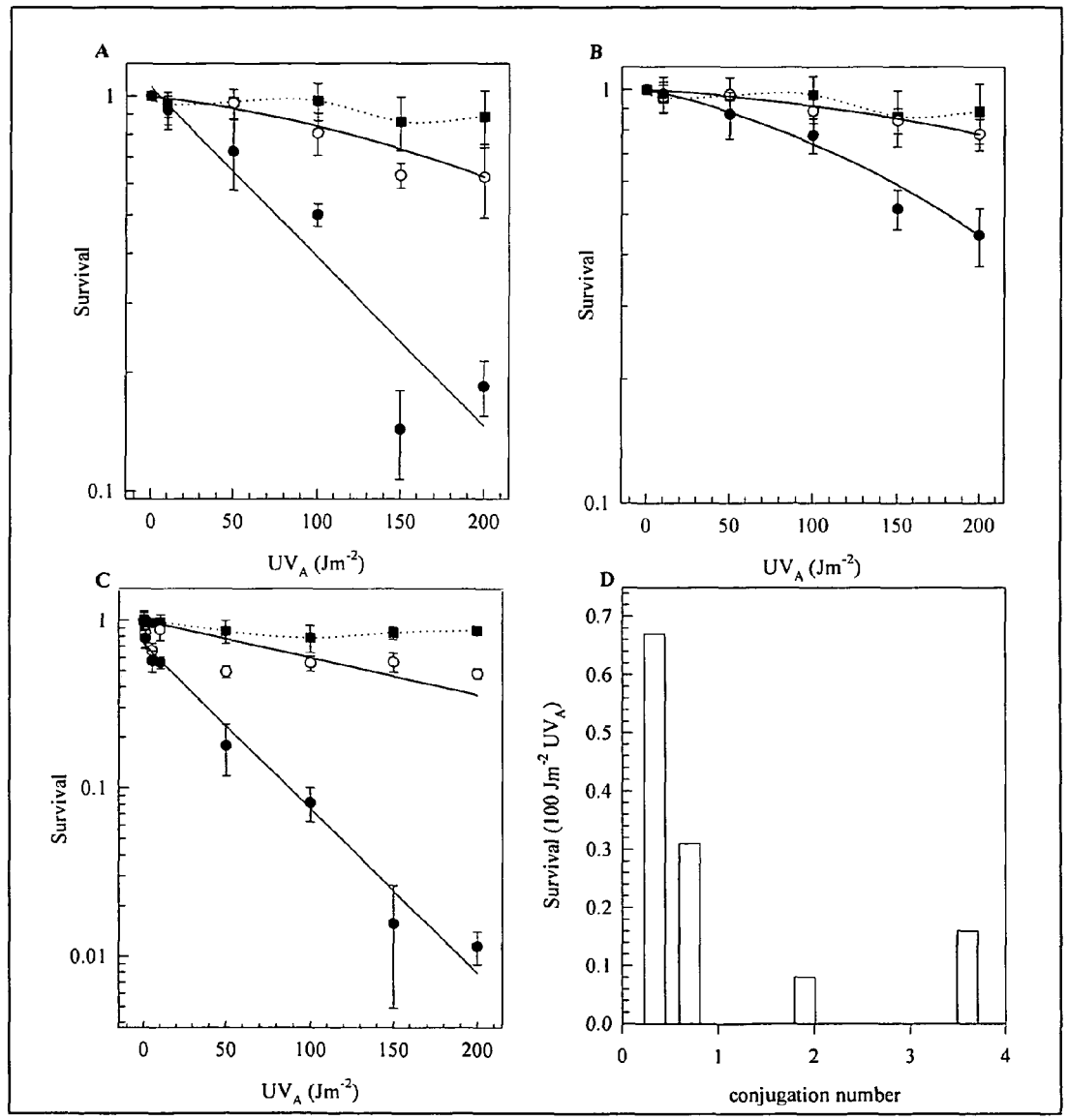
FIG. 12 shows clonogenic survival assays of UVA-induced cell kill of K562 cells treated with transferrin-ortho-iodoHoechst conjugates. Survival of K562 cells following incubation with the disulphide (A; conjugation no. 1.9), amide (B; conjugation no. 1.2) and hydrazone linked conjugates (C; conjugation no. 1.9) for 24 hrs at 37° C. and subsequent UVA irradiation at the indicated doses (closed circles). Cell-death was inhibited by incubation in the presence of 100-fold molar excess transferrin (open circles). The UVA doses used did not reduce the survival of K562 cells (closed squares). The effect of varying the conjugation number of the hydrazone conjugate was investigated (D). The survival following irradiation with 100 Jm-2 UVA is indicated.

Clonogenic survival assays indicated a $UV_A$ dose dependent increase in cell-death in K562 cells incubated with the conjugates (FIG. 12). Cell-killing was largely inhibited by incubation in the presence of 100-fold molar excess of unlabelled transferring, and therefore largely receptor-mediated. It should be noted that the $UV_A$ dose range used in the experiments did not result in cell-death of untreated K562 cells.

Example 25

EGF Receptor-Mediated Delivery of Ortho-iodoHoechst A431 Cells and Killing by $UV_A$—Irradiation A431 cells in AMEM containing 10% FBS, 20 mM HEPES and 80 I.U./ml gentamicin were incubated with the disulphide and acylhydrazone linked MoAB 225-ortho-iodoHoechst conjugates for 24 hours at 37° C. Following incubation the cells were irradiated with various $UV_A$ doses. The cells were then washed, treated with pronase and collected by centrifugation. An appropriate cell number from each of the samples was plated in petri dishes and incubated for 12 days to allow colony formation.

Figure 13:
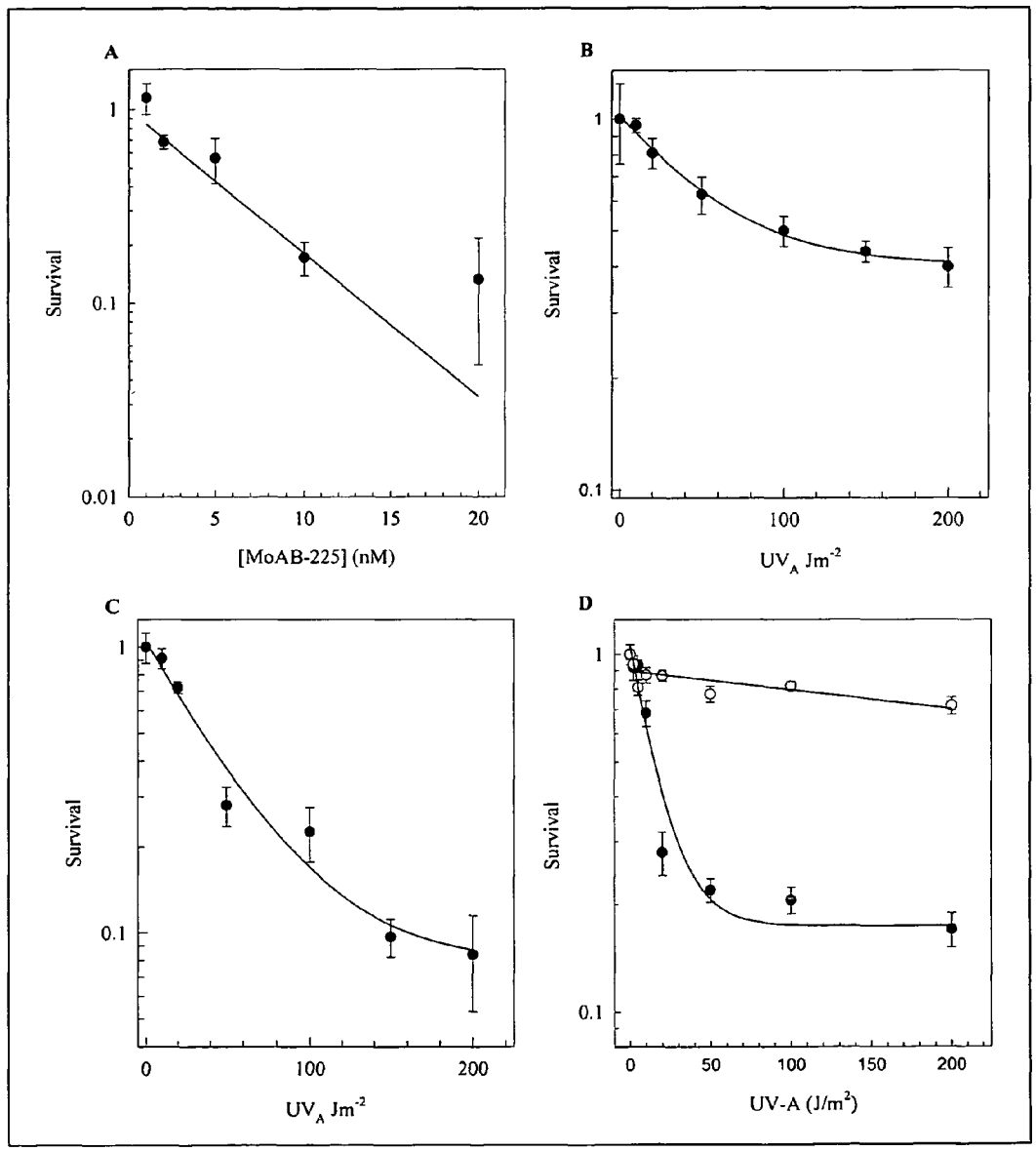
FIG. 13 shows clonogenic survival assays of UVA-induced cell kill of A431 cells treated with MoAB 225-ortho-iodoHoechst conjugates. Toxicity of unconjugated MoAB-225 in A431 cells following 24 hr incubation at 37° C. (A). Survival of A431 cells following incubation with 10 ng/ml disulphide (B) and hydrazone (C) for 24 hrs at 37° C. and subsequent UVA. Sensitisation of A431 cells (closed circles) and CHO-K1 cells (open circles) following incubation with 100 ng/ml (approximately 0.7 nM) hydrazone conjugate (D).

The clonogenic survival assay results (FIG. 13) indicated the disulphide and hydrazone linked conjugates sensitized the A431 cells to $UV_A$. Importantly, the findings indicated that the conjugate did not sensitize human EGF receptor negative CHO-K1 cells to $UV_A$. Thus the $UV_A$-induced cell kill is largely a consequence of receptor-mediated delivery of the photosensitiser to A431 cells.

Example 26

Induction of DNA Double-Stranded Breaks by DNA-Associated Decay of $^{123}$I

The experimental design exploits the plasmid DNA assay system, and agarose gel electrophoresis, as described previously to evaluate DNA breakage by the labelled minor groove binding DNA ligand, $^{125}$I-iodoHoechst 33258 (Lobachevsky, Karagiannis and Martin 2004).

The accumulation of DNA single-stranded breaks and DNA double-stranded breaks is monitored by quantitation of the decline in the fraction of intact supercoiled plasmid (S), and the corresponding increase in the fractions of relaxed (R) and linear (L) species, with the progressive accumulation of decay events. Various assumptions enable the derivation of the relationship between the parameters S, R and L (or their normalised counterparts S', R' and L'), the number of decay events (n), and for example, the yield of double-stranded breaks per decay (d) of isotope in DNA-bound ligand. However determination of d requires a value for the fraction of bound ligand (f), and this has proved a difficulty in the early experiments with $^{123}$I-iodoHoechst 33258. Accordingly, a double isotope strategy was developed, using a mixture of $^{123}$I- and $^{125}$I-iodoHoechst 33258. This approach yields a ratio d values, providing an estimate of the relative efficiency ($^{123}$I relative to $^{125}$I) for double-strand breaks per decay, which is independent of f.

$$\frac{L'}{(1-L')n_{1m}} = d_{a1}\frac{n_1}{n_{1m}} + d_{a2}\frac{n_2}{n_{1m}}$$

The basis of the double isotope method is apparent from the following relationship:

Where $n_1$ is the number of $^{123}$I decays, and $n_{1m}$ is the maximum (ie at time=infinity) number of $^{123}$I decays.

Figure 14:
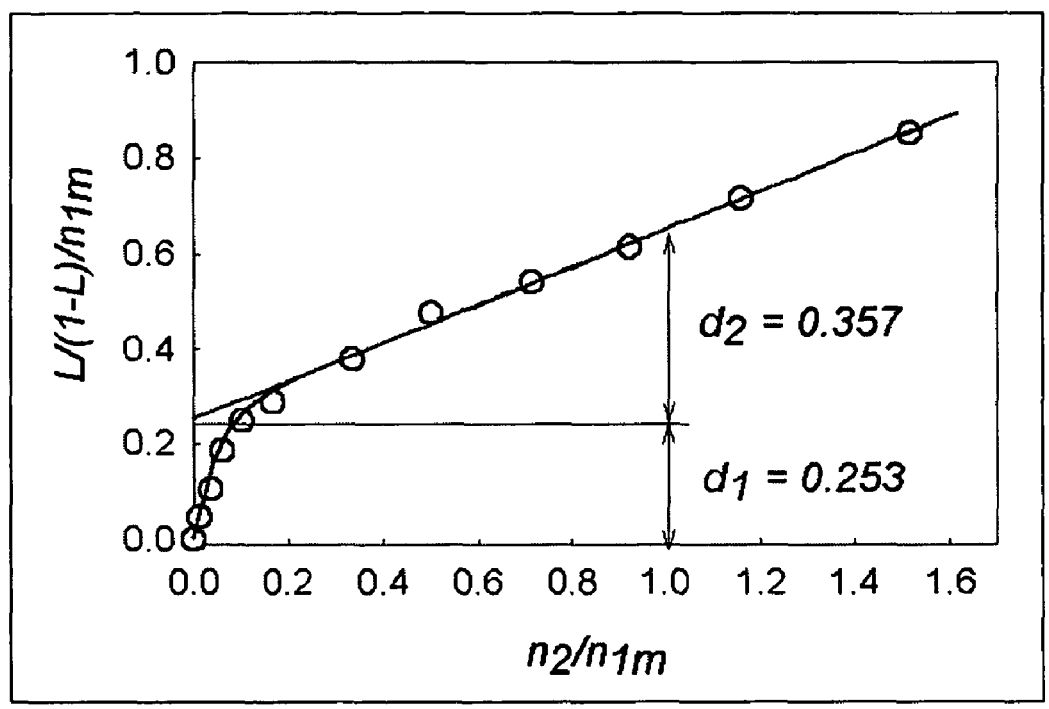
FIG. 14 shows the relative efficacy ($^{123}$I versus $^{125}$I) of DNA double-strand break induction by DNA-associated Auger decays.

A plot of the LHS term of the above equation versus $n_2$ (the number of $^{125}$I decay events in the incubation mixture) yields a two phase curve, the $2^{nd}$ phase of which approaches a straight line (when $n_1=n_{1m}$). The values for the apparent breakage DNA dsb efficiency of $^{123}$I and $^{125}$I decays ($d_{a1}$ and $d_{a2}$, respectively) are obtained from the y intercept and from the gradient of the asymptote of the second phase of the curve, as shown in FIG. 14.

The apparent breakage efficiency is related to the actual efficiency of DNA-bound decay events, d, by the expression:

$$d_a = df + \delta A$$

Where $\delta A$ is the term for the "external" component of damage, arising from decay of non-DNA-bound isotope, which can be ignored because of the particular conditions of the $$\frac{d_{a1}}{d_{a2}} = \frac{d_1 f}{d_2 f} = \frac{d_1}{d_2}$$

experiment, particularly, a low DNA concentration, A. Thus analysis of the data as exemplified in FIG. 14 provides the ratio of breakage efficiencies of $^{123}$I versus $^{125}$I decays. The results of several sets of data exemplified by FIG. 14 are summarised in Table 3 show that the relative double strand breakage efficiency of DNA-associated $^{123}$I decays is about 60% of that of $^{125}$I.

TABLE 3

Summary of Plasmid DNA breakage data for a mixture of $^{123}$I- and $^{125}$I-iodoHoechst 33258.

| Sample | $d_{a1}(^{123}I)$ | $d_{a2}(^{125}I)$ | $d_{a1}(^{123}I)/d_{a2}(^{125}I)$ | $^{125}I/^{123}I$ | Average $d_{a1}(^{123}I)/d_{a2}(^{125}I)$ |
|---|---|---|---|---|---|
| N1.2 | 0.244 | 0.413 | 0.59 | 1.74 | 0.63 ± 0.03 |
| N2.2 | 0.253 | 0.397 | 0.64 | 5.19 | |
| N3.2 | 0.314 | 0.474 | 0.66 | 16.0 | |
| D1.2 | 0.158 | 0.252 | 0.63 | 1.79 | 0.65 ± 0.03 |
| D2.2 | 0.170 | 0.248 | 0.69 | 5.32 | |
| D3.2 | 0.159 | 0.258 | 0.62 | 14.9 | |

Six sets of experimental data exemplified in FIG. 14 are shown. Three sets are from experiments done in aqueous buffer (the "N" series) and the other three sets (D1-D3) are from experiments with DMSO added to 10%.

Example 27

Induction of DNA Double-Stranded Breaks by DNA-Associated Decay of $^{124}$I

Figure 15:
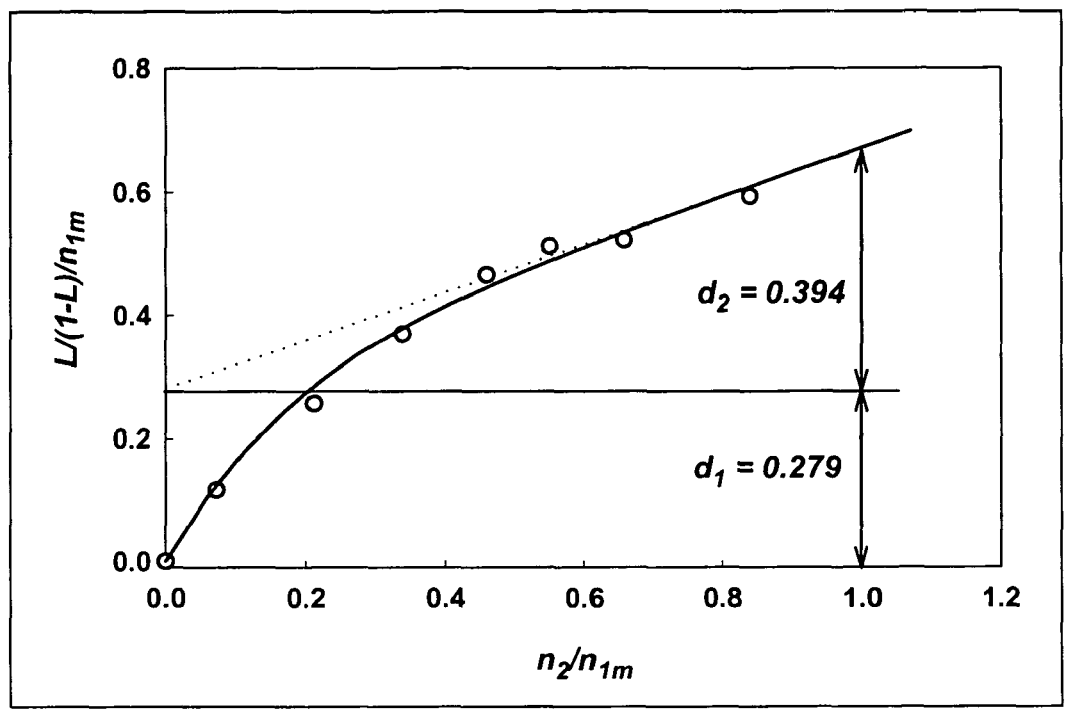
FIG. 15 shows a data plot from one of the $^{124}$I/$^{125}$I-double isotope experiments demonstrating the efficacy of $^{124}$I in initiating DNA double strand breaks.

In experiments exactly analogous to those described in Example 25, induction of DNA double-strand breaks was investigated for $^{124}$I-iodoHoechst 33258. The results of preliminary experiments (to our knowledge the first such experiments done with DNA-associated $^{124}$I) are shown in FIG. 15 and Table 4. The results demonstrate the efficacy of $^{124}$I, an Auger emitter. The DNA-associated decays are at least as efficient as those of the $^{123}$I counterpart.

TABLE 5

DNA-breakage by DNA-bound $^{124}$I-iodoHoechst 33258; relative efficacy.

| Sample | $d_{a1}(^{124}I)$ | $d_{a2}(^{125}I)$ | $d_{a1}(^{124}I)/d_{a2}(^{125}I)$ | $^{124}I/^{125}I$ molar ratio | Average $d_{a1}(^{124}I)/d_{a2}(^{125}I)$ |
|---|---|---|---|---|---|
| A2 | 0.279 ± 0.058 | 0.394 ± 0.101 | 0.71 | 2.4 | 0.76 ± 0.05 |
| A3 | 0.506 ± 0.198 | 0.620 ± 0.062 | 0.82 | 14.3 | |
| B1 | 0.381 ± 0.078 | 0.510 ± 0.063 | 0.75 | 5.4 | |
| B2 | 0.126 ± 0.038 | 0.162 ± 0.025 | 0.76 | 6.4 | |

Example 28

Induction of DNA Double-Stranded Breaks (DSB) by Decay of DNA-Associated Isotope $^{124}$I Plasmid DNA DSB following decay of DNA-associated isotope $^{124}$I was studied in experiments similar to those described in Example 26, except that different DNA ligands were used, namely meta-$^{124}$I-iodo Hoechst and para-$^{124}$I-iodo Hoechst. The results indicated similar probabilities of DSB per decay of $^{124}$I for both ligands. In TE values for DSB/decay are 0.69+/−0.04 and 0.64+/−0.03 for meta- and para-ligands respectively. In TE+DMSO values are 0.52+/−0.03 and 0.51+/−0.06 DSB per decay for meta- and para-ligands respectively. Comparison of these values to those in Table 4 indicate that DNA DSB are induced by decay of $^{124}$I and $^{123}$I with similar efficiencies.

Example 29

K562 Cells Survival Following Incubation with $^{123}$I-iodoHoechst 33258

Figure 16:
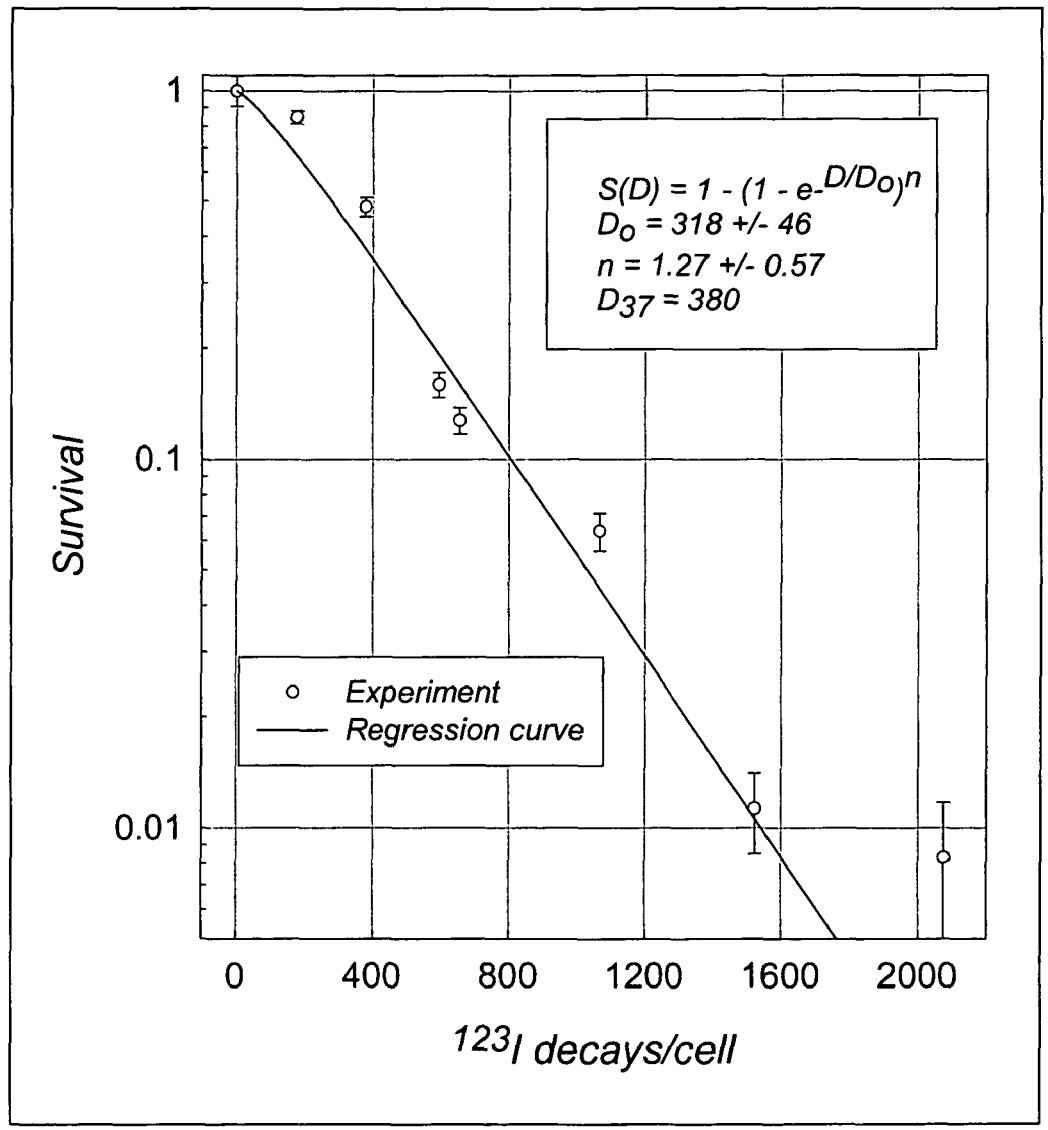
FIG. 16 shows a plot of cell survival of K562 cells (5×10$^5$/ml) in RPMI-1640 medium containing 10% FBS and gentamicin incubated with varying specific activities of $^{127}$I/$^{123}$I-iodoHoechst 33258 (500 nM) for 1 hour at 37° C.

Survival curve studies with K562 cells treated with $^{125}$I-iodoHoechst 33258 previously indicated that a lethal event coincides to about 130 $^{125}$I decays per nucleus (Karagiannis, Lobachevsky and Martin 2000). Now, the results from the analogous experiment with $^{123}$I-iodoHoechst 33258 (FIG. 16) indicates that the cytotoxic efficiency of this ligand approaches that of its $^{125}$I-counterpart. This result, taken together with those in Examples 26 and 27, clearly suggests that cytotoxicity of DNA-associated 124, will also be sufficient to be exploitable in a radioimmunotherapy context.

Cells ($5\times10^5$/ml) in RPMI-1640 medium containing 10% FBS and gentamicin were incubated with varying specific activities of $^{127}$I/$^{123}$I-iodoHoechst 33258 (500 nM) for 1 hour at 37° C. Following incubation the cells were separated from the supernatant by 3 centrifugation (400×g for 3 minutes)-wash cycles. The cell pellets were suspended in RPMI medium and $^{123}$I-decays were accumulated at 5° C. for 24 hours. Following accumulation of decays, the cell-pellets were isolated by centrifugation at 400×g for 3 minutes, suspended in AMEM containing 20% FBS and an appropriate cell number from each of the samples was cloned in semi-solid (0.33% (w/v)) noble agar in 6-well microtiter plates, as discussed above. The results indicated that for $^{123}$I-iodoHoechst 33258 a lethal event for K562 cells required about 230 $^{123}$I-decays per cell (given that 60% of the cellular iodoHoechst 33258 is localised in the nucleus).

REFERENCES

Arteaga, C. L. (2003). ErbB-targeted therapeutic approaches in human cancer. *Exp Cell Res*, 284, 122-30.

Breusegem, S. Y., Sadat-Ebrahimi, S. E., Douglas, K. T., Clegg, R. M. & Loontiens, F. G. (2001). Increased stability and lifetime of the complex formed between DNA and meta-phenyl-substituted Hoechst dyes as studied by fluorescence titrations and stopped-flow kinetics. *J Mol Biol*, 308, 649-63.

Chester, K. A., Mayer, A., Bhatia, J., Robson, L., Spencer, D. I., Cooke, S. P., Flynn, A. A., Sharma, S. K., Boxer, G., Pedley, R. B. & Begent, R. H. (2000). Recombinant anti-carcinoembryonic antigen antibodies for targeting cancer. *Cancer Chemother Pharmacol*, 46 Suppl, S8-12.

Collingridge, D. R., Carroll, V. A., Glaser, M., Aboagye, E. O., Osman, S., Hutchinson, O. C., Barthel, H., Luthra, S. K., Brady, F., Bicknell, R., Price, P. & Harris, A. L. (2002). The development of [(124)I]iodinated-VG76e: a novel tracer for imaging vascular endothelial growth factor in vivo using positron emission tomography. *Cancer Res*, 62, 5912-9.

Denny, W. A. & Wakelin, L. P. (1986). Kinetic and equilibrium studies of the interaction of amsacrine and anilino ring-substituted analogues with DNA. *Cancer Res*, 46, 1717-21.

Dolmans, D. E., Fukumura, D. & Jain, R. K. (2003). Photodynamic therapy for cancer. *Nat Rev Cancer*, 3, 380-7.

Duzkale, H., Pagliaro, L. C., Rosenblum, M. G., Varan, A., Liu, B., Reuben, J., Wierda, W. G., Korbling, M., McManis, J. D., Glassman, A. B., Scheinberg, D. A. & Freireich, E. J. (2003). Bone marrow purging studies in acute myelogenous leukemia using the recombinant anti-CD33 immunotoxin HuM195/rGel. *Biol Blood Marrow Transplant*, 9, 364-72.

Edelson, R., Berger, C., Gasparro, F., Jegasothy, B., Heald, P., Wintroub, B., Vonderheid, E., Knobler, R., Wolff, K., Plewig, G. & et al. (1987). Treatment of cutaneous T-cell lymphoma by extracorporeal photochemotherapy. Preliminary results. *N Engl J Med*, 316, 297-303.

Faulk, W. P., Hsi, B. L. & Stevens, P. J. (1980). Transferrin and transferrin receptors in carcinoma of the breast. *Lancet*, 2, 390-2.

Friedberg, J. W., Kim, H., Li, S., Neuberg, D., Boyd, K., Daley, H., Fisher, D. C., Gribben, J. G., Spitzer, T. & Freedman, A. S. (2003). Ex vivo B cell depletion using the Eligix B Cell SC system and autologous peripheral blood stem cell transplantation in patients with follicular non-Hodgkin's lymphoma. *Bone Marrow Transplant*, 32, 681-6.

Heald, P., Rook, A., Perez, M., Wintroub, B., Knobler, R., Jegasothy, B., Gasparro, F., Berger, C. & Edelson, R. (1992). Treatment of erythrodermic cutaneous T-cell lymphoma with extracorporeal photochemotherapy. *J Am Acad Dermatol*, 27, 427-33.

Honigsmann, H. (2001). Phototherapy for psoriasis. *Clin Exp Dermatol*, 26, 343-50.

Jorissen, R. N., Walker, F., Pouliot, N., Garrett, T. P., Ward, C. W. & Burgess, A. W. (2003). Epidermal growth factor receptor: mechanisms of activation and signalling. *Exp Cell Res*, 284, 31-53.

Kapuscinski, J. & Darzynkiewicz, Z. (1987). Interactions of acridine orange with double stranded nucleic acids. Spectral and affinity studies. *J Biomol Struct Dyn*, 5, 127-43.

Klausner, R. D., Van Renswoude, J., Ashwell, G., Kempf, C., Schechter, A. N., Dean, A. & Bridges, K. R. (1983). Receptor-mediated endocytosis of transferrin in K562 cells. *J Biol Chem*, 258, 4715-24.

Kreitman, R. J. (2001). Toxin-labeled monoclonal antibodies. *Curr Pharm Biotechnol*, 2, 313-25.

Lobachevsky, P. N. & Martin, R. F. (2000a). Iodine-125 decay in a synthetic oligodeoxynucleotide. I. Fragment size distribution and evaluation of breakage probability. *Radiat Res*, 153, 263-70.

Lobachevsky, P. N. & Martin, R. F. (2000b). Iodine-125 decay in a synthetic oligodeoxynucleotide. II. The role of auger electron irradiation compared to charge neutralization in DNA breakage. *Radiat Res*, 153, 271-8.

Martin, R. F., Kelly, D. P., Roberts, M., Green, A., Denison, L., Rose, M., Reum, M. & Pardee, M. (1994). Comparative studies of UV-induced DNA cleavage by structural isomers of an iodinated DNA ligand. *Int J Radiat Oncol Biol Phys*, 29, 549-53.

Martin, R. F., Murray, V., D'Cunha, G., Pardee, M., Kampouris, E., Haigh, A., Kelly, D. P. & Hodgson, G. S. (1990). Radiation sensitization by an iodine-labelled DNA ligand. *Int J Radiat Biol*, 57, 939-46.

Miyagi, K., Sampson, R. W., Sieber-Blum, M. & Sieber, F. (2003). Crystal violet combined with Merocyanine 540 for the ex vivo purging of hematopoietic stem cell grafts. *J Photochem Photobiol B*, 70, 133-44.

Mohr, M., Dalmis, F., Hilgenfeld, E., Oelmann, E., Zuhlsdorf, M., Kratz-Albers, K., Nolte, A., Schmitmann, C., Onaldi-Mohr, D., Cassens, U., Serve, H., Sibrowski, W., Kienast, J. & Berdel, W. E. (2001). Simultaneous immunomagnetic CD34+ cell selection and B-cell depletion in peripheral blood progenitor cell samples of patients suffering from B-cell non-Hodgkin's lymphoma. *Clin Cancer Res*, 7, 51-7.

Palm, S., Enmon, R. M., Jr., Matei, C., Kolbert, K. S., Xu, S., Zanzonico, P. B., Finn, R. L., Koutcher, J. A., Larson, S. M. & Sgouros, G. (2003). Pharmacokinetics and Biodistribution of (86)Y-Trastuzumab for (90)Y dosimetry in an ovarian carcinoma model: correlative MicroPET and MRI. *J Nucl Med*, 44, 1148-55.

Parrish, J. A., Fitzpatrick, T. B., Tanenbaum, L. & Pathak, M. A. (1974). Photochemotherapy of psoriasis with oral methoxsalen and longwave ultraviolet light. *N Engl J Med*, 291, 1207-11.

Piehler, J., Brecht, A., Gauglitz, G., Zerlin, M., Maul, C., Thiericke, R. & Grabley, S. (1997). Label-free monitoring of DNA-ligand interactions. *Anal Biochem*, 249, 94-102.

Pomplun, E., Booz, J. & Charlton, D. E. (1987). A Monte Carlo simulation of Auger cascades. *Radiat Res*, 111, 533-52.

Roecklein, B. A., Reems, J., Rowley, S. & Torok-Storb, B. (1998). Ex vivo expansion of immature 4-hydroperoxycyclophosphamide-resistant progenitor cells from G-CSF-mobilized peripheral blood. *Biol Blood Marrow Transplant*, 4, 61-8.

Shields, A. F., Grierson, J. R., Dohmen, B. M., Machulla, H. J., Stayanoff, J. C., Lawhom-Crews, J. M., Obradovich, J. E., Muzik, O. & Mangner, T. J. (1998). Imaging proliferation in vivo with [F-18]FLT and positron emission tomography. *Nat Med*, 4, 1334-6.

Soukos, N. S., Hamblin, M. R., Keel, S., Fabian, R. L., Deutsch, T. F. & Hasan, T. (2001). Epidermal growth factor receptor-targeted immunophotodiagnosis and photoimmunotherapy of oral precancer in vivo. *Cancer Res*, 61, 4490-6.

Spyridonidis, A., Schmidt, M., Bernhardt, W., Papadimitriou, A., Azemar, M., Wels, W., Groner, B. & Henschler, R. (1998). Purging of mammary carcinoma cells during ex vivo culture of CD34+ hematopoietic progenitor cells with recombinant immunotoxins. *Blood*, 91, 1820-7.

Verel, I., Visser, G. W., Boellaard, R., Boerman, O. C., van Eerd, J., Snow, G. B., Lammertsma, A. A. & van Dongen, G. A. (2003a). Quantitative 89Zr immuno-PET for in vivo scouting of 90Y-labeled monoclonal antibodies in xenograft-bearing nude mice. *J Nucl Med*, 44, 1663-70.

Verel, I., Visser, G. W., Boerman, O. C., van Eerd, J. E., Finn, R., Boellaard, R., Vosjan, M. J., Stigter-van Walsum, M., Snow, G. B. & van Dongen, G. E. (2003b). Long-lived positron emitters zirconium-89 and iodine-124 for scouting of therapeutic radioimmunoconjugates with PET. *Cancer Biother Radiopharm*, 18, 655-61.

Vrouenraets, M. B., Visser, G. W., Loup, C., Meunier, B., Stigter, M., Oppelaar, H., Stewart, F. A., Snow, G. B. & van Dongen, G. A. (2000). Targeting of a hydrophilic photosensitizer by use of internalizing monoclonal antibodies: A new possibility for use in photodynamic therapy. *Int J Cancer*, 88, 108-14.

Wadkins, R. M. & Graves, D. E. (1989). Thermodynamics of the interactions of M-AMSA and o-AMSA with nucleic acids: influence of ionic strength and DNA base composition. *Nucleic Acids Res*, 17, 9933-46.

Brinkley, M., 1992, A brief survey of methods for preparing protein conjugates with dyes, haptens, and cross-linking reagents. Bioconjug Chem, 3, 2-13

Ciechanover, A., Schwartz, A. L., Dautry-Varsat, A. and Lodish, H. F., 1983, Kinetics of internalization and recycling of transferrin and the transferrin receptor in a human hepatoma cell line. Effect of lysosomotropic agents. J Biol Chem, 258, 9681-9689

Karagiannis, T. C., Lobachevsky, P. N. and Martin, R. F., 2000, Cytotoxicity of an 125I-labelled DNA ligand. Acta Oncol, 39, 681-685

Kohgo, Y., Kondo, H., Kato, J., Sasaki, K., Tsushima, N., Nishisato, T., Hirayama, M., Fujikawa, K., Shintani, N., Mogi, Y. and Niitsu, Y, 1990, Kinetics of internalization and cytotoxicity of transferrin-neocarzinostatin conjugate in human leukemia cell line, K562. Jpn. J. Cancer Res., 81, 91-99.

Kassis, A. I., Howell, W., Sastry, K. S. R. and Adelstein, S. J., 1988, Positional effects of Auger decays in mammalian cells in culture. In DNA damage by Auger emitters. Baverstock, K. F. and Charlton, D. E. (eds.), Taylor and Francis, London, UK, p. 1-14.

Goddu, S. M., Rao, D. V. and Howell, R. W., 1994, Multicellular dosimetry for micrometastases: Dependence of self-dose versus cross-dose to cell nuclei on type and energy of radiation and subcellular distribution of radionuclides. J. Nucl. Med., 35, 521-530.

Karagiannis, T. C., 2001, Targeting $^{125}$I-labelled ligands to the DNA of tumor cells, Ph D thesis, submitted to the Department of Pathology, The University of Melbourne in October 2001, passed by the examiners in February 2002 and released for public access in April 2004.

Lobachevsky, P. N. and Martin, R. F., 2004, An Improved Approach to the Analysis of Plasmid DNA Breakage by Decay of DNA-Associated Auger Emitters. Int. J. Radiat. Biol. 80, 861-866.

Lobachevsky, P. N., Karagiannis, T. C. and Martin, R. F., 2004, Plasmid DNA Breakage by Decay of DNA-Associated Auger Emitters: Approaches To Analysis of Experimental Data. Radiat. Res. 162, 84-95.

Martin, R. F. and Pardee, M., 1985, Preparation of carrier free [125I]iodoHoechst 33258. Int J Appl Radiat Isot, 36, 745-747

Webb, I. J., Friedberg, W., Gribben, J. G., Fisher, D. C., Spitzer, T., Neuberg, D., Jallow, H., Kim, H., Houde, H., Monroy, R., Schrmittling, R. & Freedman, A. S. (2002). Effective purging of autologous hematopoietic stem cells using anti-B-cell monoclonal antibody-coated high-density microparticles prior to high-dose therapy for patients with non-Hodgkin's lymphoma. *Biol Blood Marrow Transplant*, 8, 429-34.

The invention claimed is:

1. A cell targeting conjugate comprising the following components that are covalently conjugated via a hydrazone, disulphide or amide bond linker that is degradable within the target cells:
   a DNA minor groove binding ligand incorporating an effective Auger electron-emitting, gamma-emitting or positron-emitting atom or photoactive moiety;
   a target cell specific protein or peptide that is capable of internalisation by target cells;
   wherein the cell targeting conjugate is represented by Formula (I), wherein:

Formula (I)

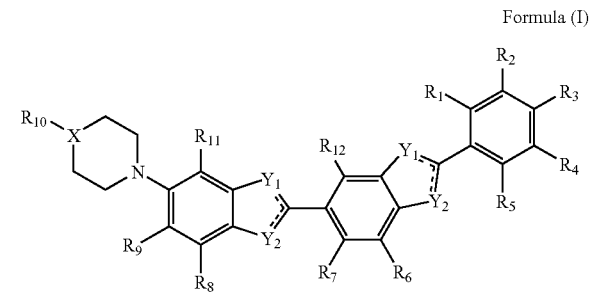

X is carbon or nitrogen;

$Y_1$ and $Y_2$ are selected from C(R'), nitrogen, N(R'), oxygen and sulfur, wherein R' is hydrogen, optionally substituted alkyl or optionally substituted alkenyl, and wherein $Y_1$ and $Y_2$ are not both either C(R') or nitrogen;

═ is a double bond unless the attached $Y_1$ or $Y_2$ is N(R'), oxygen or sulfur in which case it is a single bond;

$R_1$ to $R_{12}$ are selected from hydrogen, halogen, hydroxy, amino, optionally substituted alkyl, optionally substituted alkenyl, a moiety including a target cell specific protein or peptide, an Auger electron-emitting moiety, a gamma-emitting moiety, a positron-emitting moiety and a photoactive moiety, and wherein two of $R_1$ to $R_5$ may together form optionally substituted cycloalkyl, cycloalkenyl or aryl; wherein at least one of $R_1$ to $R_{12}$ comprises a target cell specific protein or peptide, and wherein at least one other of $R_1$ to $R_{12}$ comprises an Auger electron-emitting moiety, a gamma-emitting moiety, a positron-emitting moiety and/or a photoactive moiety;

and salts and/or tautomers thereof.

2. The cell targeting conjugate according to claim 1 wherein the target cell specific protein or peptide is selected from anti-A33, C595, 4D5, trastuzumab, egf/R3, humanized h-R3, C225, BrE-3, murine A7, C50, humanized MN-14, anti-A33, MSN-1, bivatuzumab, U36, KIS1, HuM195, anti-CD45, anti-CD19, TXU(anti-CD7)-pokeweed antiviral protein, M195, anti-CD23, apolizumab (Hu1D10), Campath-1H, N901, Ep2, somatostatin analogues, tositumomab, ibritumomab tiuxetan, HB22.7, anti-CD40, OC125, PAM4 and J591.

3. The cell targeting conjugate according to claim 1 wherein the gamma-emitting or positron-emitting moiety is distanced from a DNA minor groove binding region of the conjugate.

4. A cell targeting conjugate according to claim 3 selected from the following:

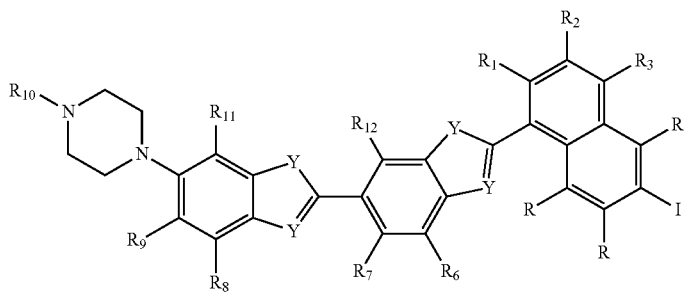

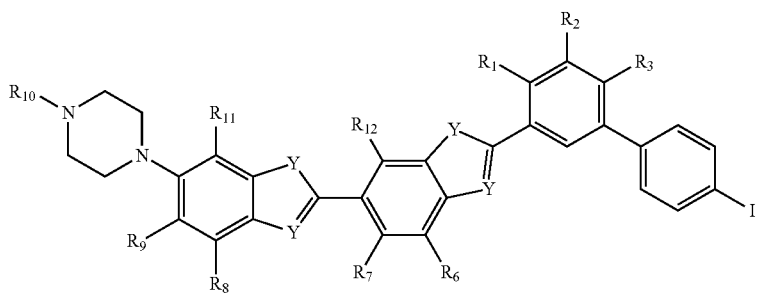

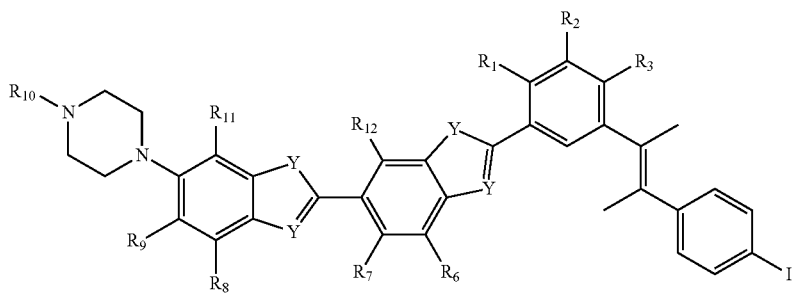

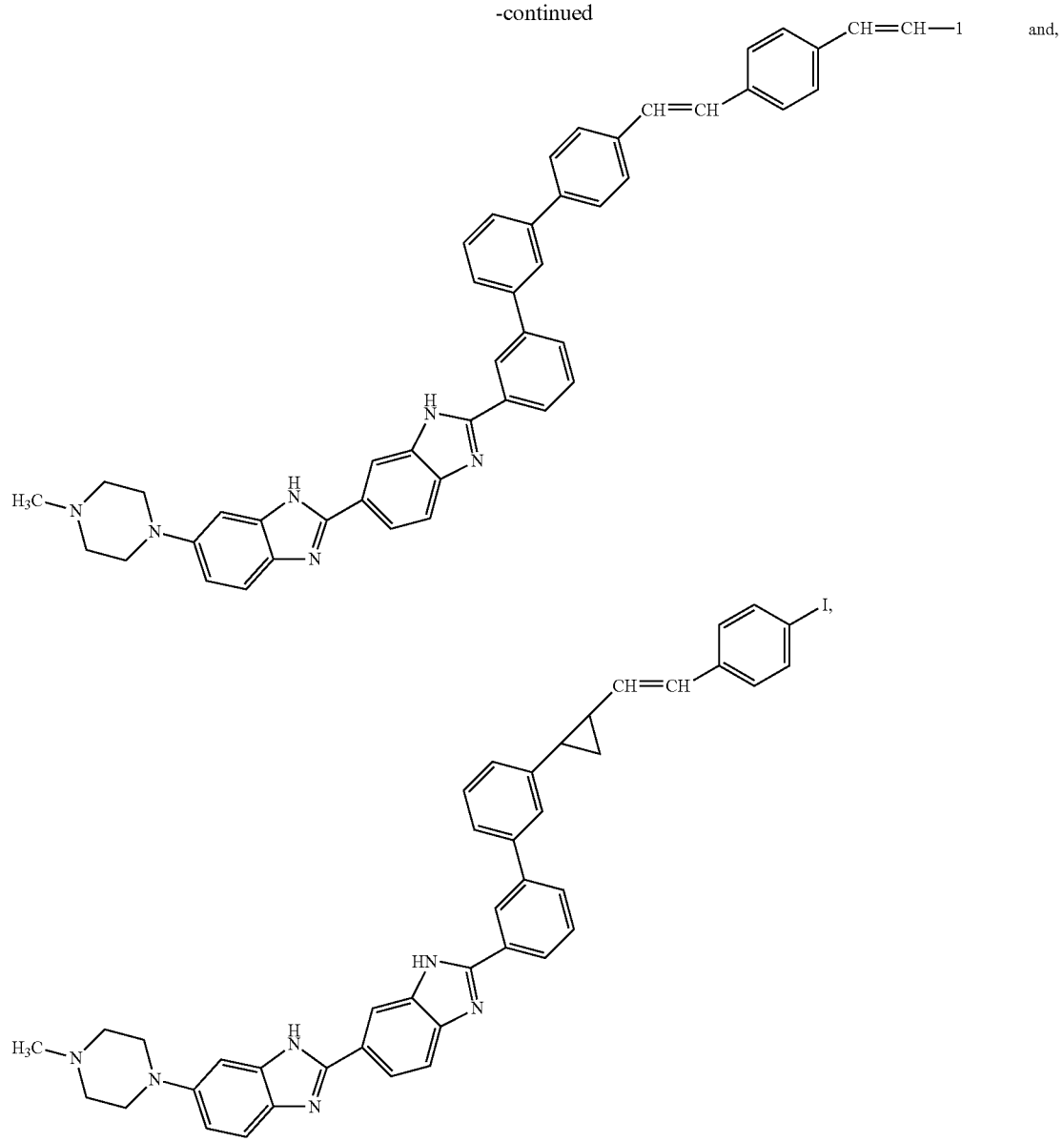
wherein R represents hydrogen, hydroxy, amino, halogen or optionally substituted alkyl, alkenyl or alkynyl, and wherein the gamma-emitting or positron-emitting moiety is iodine (I).
* * * * *